(12) United States Patent
Vijayan et al.

(10) Patent No.: US 11,499,185 B2
(45) Date of Patent: *Nov. 15, 2022

(54) NUCLEIC ACID SEQUENCING METHODS AND SYSTEMS

(71) Applicant: OMNIOME, INC., San Diego, CA (US)

(72) Inventors: Kandaswamy Vijayan, San Diego, CA (US); Eugene Tu, San Diego, CA (US); Mark A. Bernard, Power, CA (US)

(73) Assignee: PACIFIC BIOSCIENCES OF CALIFORNIA, INC., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/046,707

(22) Filed: Jul. 26, 2018

(65) Prior Publication Data

US 2019/0032124 A1    Jan. 31, 2019

Related U.S. Application Data

(63) Continuation of application No. 14/805,381, filed on Jul. 21, 2015, now Pat. No. 10,077,470.

(51) Int. Cl.
   *C12Q 1/68*       (2018.01)
   *C12Q 1/6869*    (2018.01)

(52) U.S. Cl.
   CPC .................................. *C12Q 1/6869* (2013.01)

(58) Field of Classification Search
   None
   See application file for complete search history.

(56) References Cited

U.S. PATENT DOCUMENTS

| | | | |
|---|---|---|---|
| 5,302,509 A | 4/1994 | Cheeseman | |
| 5,614,365 A | 3/1997 | Tabor et al. | |
| 6,485,909 B1 | 11/2002 | Hong et al. | |
| 6,720,177 B2 | 4/2004 | Ghadiri et al. | |
| 6,828,094 B2 | 12/2004 | Kilger et al. | |
| 6,908,736 B1 | 6/2005 | Densham | |
| 7,008,766 B1 | 3/2006 | Densham et al. | |
| 7,223,540 B2 | 5/2007 | Pourmand et al. | |
| 7,264,934 B2 | 9/2007 | Fuller et al. | |
| 7,329,492 B2 | 2/2008 | Hardin et al. | |
| 7,449,297 B2 | 11/2008 | Freije et al. | |
| 7,482,120 B2 | 1/2009 | Buzby et al. | |
| 7,604,963 B2 | 10/2009 | Densham et al. | |
| 7,635,578 B2 | 12/2009 | Li et al. | |
| 7,713,698 B2 | 5/2010 | Li et al. | |
| 7,790,869 B2 | 9/2010 | Li et al. | |
| 7,871,771 B2 | 1/2011 | Fuller et al. | |
| 7,939,264 B1 | 5/2011 | Densham et al. | |
| 8,071,755 B2 | 12/2011 | Efcavitch et al. | |
| 8,088,575 B2 | 1/2012 | Li et al. | |
| 8,133,672 B2 | 3/2012 | Bjornson et al. | |
| 8,236,532 B2 | 8/2012 | Eltoukhy et al. | |
| 8,298,792 B2 | 10/2012 | Meng et al. | |
| 8,399,196 B2 | 3/2013 | Hoser et al. | |
| 8,481,266 B2 | 7/2013 | Shao et al. | |
| 8,535,881 B2 | 9/2013 | Schneider et al. | |
| 8,603,741 B2 | 12/2013 | Emig et al. | |
| 8,632,975 B2 | 1/2014 | Vander Horn et al. | |
| 8,658,365 B2 | 2/2014 | Bjornson et al. | |
| 8,703,461 B2 | 4/2014 | Peris et al. | |
| 8,911,972 B2 | 12/2014 | Chaisson et al. | |
| 8,986,930 B2 | 3/2015 | Fedorov et al. | |
| 9,255,258 B2 | 2/2016 | Luo et al. | |
| 9,279,155 B2 | 3/2016 | Bjornson et al. | |
| 9,279,154 B2 | 6/2016 | Previte et al. | |
| 9,476,094 B2 | 10/2016 | Densham | |
| 10,077,470 B2 * | 9/2018 | Vijayan ................ | C12Q 1/6869 |
| 10,246,744 B2 * | 4/2019 | Vijayan ................ | C12Q 1/6869 |
| 2006/0292583 A1 | 12/2006 | Schneider et al. | |
| 2007/0009925 A1 | 1/2007 | Fang et al. | |
| 2009/0061447 A1 | 3/2009 | Schneider et al. | |
| 2010/0316999 A1 | 12/2010 | Densham et al. | |
| 2010/0317012 A1 | 12/2010 | Ju et al. | |
| 2010/0330570 A1 * | 12/2010 | Vander Horn ........... | C12Q 1/68 435/6.11 |
| 2011/0008794 A1 | 1/2011 | Schneider et al. | |

(Continued)

FOREIGN PATENT DOCUMENTS

| CN | 107849605 | 3/2018 |
|---|---|---|
| EP | 1115848 | 7/2001 |

(Continued)

OTHER PUBLICATIONS

EP15745338.2, "Office Action", dated Jul. 15, 2019, 5 pages.
EP15745338.2, "Office Action", dated Nov. 14, 2018, 4 pages.
EP15745338.2, "Office Action", dated Nov. 21, 2019, 4 pages.
APCH231: Chemical Analysis Complexometric Titrations EDTA, notes compiled by Dr. C. Southway, p. 30-42(http://cheminnerweb.ukzn.ac.za/libraries/apch231_h_govender_s_notes/apch231_edta.sflb.ashx).
"International Search Report and Written Opinion" dated Feb. 9, 2016, issued in International Application No. PCT/US2015/041415, 14 pages.
U.S. Appl. No. 14/805,381, "Final Office Action", dated Dec. 14, 2017, 17 pages.
U.S. Appl. No. 14/805,381, "Non-Final Office Action", dated Aug. 24, 2017, 13 pages.

(Continued)

*Primary Examiner* — Stephanie K Mummert
(74) *Attorney, Agent, or Firm* — Kilpatrick Townsend & Stockton LLP

(57) ABSTRACT

The present disclosure provides compositions, methods and systems for sequencing a template nucleic acid using a polymerase based, nucleic acid binding reaction involving examination of the interaction between a polymerase and template nucleic acid in the presence of one or more unlabeled nucleotides. The methods rely, in part, on identifying a base of a template nucleic acid during nucleic acid synthesis by controlling the sequencing reaction conditions. Template nucleic acid bases may be identified during an examination step followed by an optional incorporation step.

24 Claims, 16 Drawing Sheets

Specification includes a Sequence Listing.

(56) References Cited

U.S. PATENT DOCUMENTS

| | | |
|---|---|---|
| 2011/0237464 A1 | 9/2011 | Cunningham et al. |
| 2013/0165328 A1 | 6/2013 | Previte et al. |
| 2014/0127680 A1 | 5/2014 | Emig et al. |
| 2014/0234940 A1 | 8/2014 | Peris et al. |
| 2016/0010150 A1 | 1/2016 | Emig et al. |
| 2016/0168633 A1 | 6/2016 | Previte et al. |
| 2016/0177384 A1 | 6/2016 | Bjornson et al. |
| 2016/0208318 A1 | 7/2016 | Vander Horn et al. |
| 2017/0022553 A1 | 1/2017 | Vijayan et al. |

FOREIGN PATENT DOCUMENTS

| | | |
|---|---|---|
| EP | 3325642 | 5/2018 |
| JP | 2006308292 | 11/2006 |
| JP | 2008104463 | 5/2008 |
| WO | 1990/013666 | 11/1990 |
| WO | 2001/016375 | 3/2001 |
| WO | 2002004680 | 1/2002 |
| WO | 2005/121363 | 12/2005 |
| WO | 2009/145828 | 12/2009 |
| WO | 2009145820 | 12/2009 |
| WO | 2010/068884 | 6/2010 |
| WO | 2010/111690 | 9/2010 |
| WO | 2011/159942 | 12/2011 |
| WO | 2012/166742 | 12/2012 |
| WO | 2013/096692 | 6/2013 |
| WO | 2017014762 | 1/2017 |

OTHER PUBLICATIONS

U.S. Appl. No. 14/805,381, "Non-Final Office Action", dated Feb. 12, 2018, 20 pages.
U.S. Appl. No. 14/805,381, "Notice of Allowance", dated Jul. 3, 2018, 10 pages.
Agnarsson et al., "On-Chip modulation of evanescent illumination and live-cell imaging with polymer waveguides", Optics Express, Nov. 7, 2011, vol. 19, No. 23, pp. 22929-22935.
Anker et al., "Biosensing with Plasmonic Nanosensors", Nature Materials 7, No. 6, Jun. 2008, pp. 442-453.
Bandwar et al., "Peculiar 2-Aminopurine Fluorescence Monitors the Dynamics of Open Complex Formation by Bacteriophage T7 RNA Polymerase", The Journal of Biological Chemistry, vol. 275, No. 17, Issue of 27, 2001, pp. 14075-14082.
Brockman et al., "A Multistep Chemical Modification Procedure to Create DNA Arrays on Gold Surfaces for the Study of Protein—DNA Interactions with Surface Plasmon Resonance Imaging", Journal of the American Chemical Society 121, Sep. 1999, pp. 8044-8051.
Brown et al., "Pre-Steady-State Kinetic Analysis of Truncated and Full-Length *Saccharomyces cerevisiae* DNA Polymerase Eta", Journal of Nucleic Acids, 2010, Article ID 871939, 11 pages.
Campagnola et al., "High-throughput Screening Identification of Poliovirus RNA-dependent RNA Polymerase Inhibitors", Antiviral Res. Sep. 2011; vol. 91, No. 3, pp. 241-251.
Chan et al., "A general method for discovering inhibitors of protein-DNA interactions using photonic crystal biosensors", ACS Chem Biol, vol. 3, No. 7, Jul. 18, 2008, pp. 437-448.
Chen et al., "The History and Advances of Reversible Terminators Used in New Generations of Sequencing Technology", Genomics Proteomics Bioinformatics, vol. 11, No. 1, Feb. 1, 2013, pp. 34-40.
Chin et al., "The Effect of Divalent Nickel (Ni2+) on in Vivo DNA Replication by DNA Polymerase α1", Cancer Research, May 1, 1994, pp. 2337-2341.
Choi et al., "EML4-ALK Mutations in Lung Cancer that Confer Resistance to ALK Inhibitors", N. Engl. J. Med, vol. 18, 2010, pp. 1734-1739.
Concepcion, "Label-Free Detection of Biomolecular Interactions Using BioLayer Interferometry for Kinetic Characterization", Combinatorial Chemistry and High Throughput Screening, vol. 12, No. 8, 2009, pp. 791-800.

Crumpacker, "Mechanism of action of foscarnet against viral polymerase", American Journal of Medicine, vol. 92, Issue 2, Supplement 1, Feb. 14, 1992, pp. S3-S7.
Datta, "Salt Dependence of DNA binding by Thermus aquaticus and *Escherichia coli* DNA Polymerases", Journal of Biological Chemistry, vol. 278, Issue of Feb. 21, 2003, pp. 5694-5701.
Deredge et al., "The Glutamate Effect on DNA Binding by Pol I DNA Polymerases: Osmotic Stress and the Effective Reversal of Salt Linkage", J. Mol. Biol., vol. 401, 2010, pp. 223-238.
Doublie et al., "An open and closed case for all polymerases", Structure, 7, Feb. 1999, pp. R31-R35.
Dunlap, "Use of 2-Aminopurine and Tryptophan Fluorescence as Probes in Kinetic Analyses of DNA Polymerase Beta", Biochemistry, 41, 2002, pp. 11226-11235.
Dzantiev et al., "A conformational change in *E. coli* DNA polymerase I (Klenow fragment) is induced in the presence of a dNTP complementary to the template base in the active site", Biochemistry, vol. 39, No. 2, 2000, pp. 356-361.
Engtröm, "A label-free continuous total-internal-reflection-fluorescence-based immunosensor", Analytical Biochemistry, 2006, pp. 1-8.
Eriksson et al., "Pyrophosphate analogues as inhibitors of DNA polymerases of cytomegalovirus, herpes simplex virus and cellular origin", Biochimica et Biophysica Acta, vol. 696, No. 2, 1982, pp. 115-123.
Escobedo et al., "Integrated nanohole array surface plasmon resonance sensing device using a dual-wavelength source", Journal of Micromechanics and Microengineering, vol. 21, No. 11, Nov. 1, 2011.
Espinoza-Herrera et al., "Following DNA Chain Extension and Protein Conformational Changes in Crystals of a Y-Family DNA Polymerase via Raman Crystallography", Biochemistry, vol. 52, No. 29, Jul. 23, 2013.
Fang et al., "Genome-wide mapping of methylated adenine residues in pathogenic *Escherichia coli* using single-molecule real-time sequencing", Nature Biotechnology, vol. 30, No. 12, Dec. 2012, pp. 1232-1243.
Favicchio et al., "Fluorescence Spectroscopy and Anisotrophy in the analysis of DNA-Protein Interactions", Methods in Molecular Biology, DNA-Protein Interactions, vol. 543, 2009, pp. 589-611.
Federley, "New insights into the mechanism of dna replication on unmodified and benzo[a]pyrene modified templates using surface plasmon resonance", Wayne State University Dissertations, Paper 235, 2011.
Fuller et al., "The challenges of Sequencing by synthesis", Nature Biotechnology, vol. 27, No. 11, Nov. 2009, pp. 1013-1023.
Gralla et al., "Potassium Glutamate As A Transcriptional Inhibitor During Bacterial Osmoregulation", The EMBO Journal, vol. 25, No. 7, 2006, pp. 1515-1521.
Horn et al., "EML4-ALK: Honing In on a New Target in Non-Small-Cell Lung Cancer", Journal of Clinical Oncology, vol. 27, No. 26, Sep. 10, 2009, pp. 4232-4235.
Hoshino et al., "Effect of Ultrasound on DNA Polymerase Reactions: Monitoring on a 27-MHz Quartz Crystal Microbalance", Biomacromolecules, vol. 7, No. 3, 2006, pp. 682-685.
Hutter et al., "Labeled Nucleoside Triphosphates with Reversibly Terminating Aminoalkoxyl Groups", Nucleosides, Nucleotides and Nucleic Acids, vol. 29, Issue 11-12, 2010, pp. 879-895.
Ion Torrent, "Ion Torrent Amplicon Sequencing", Internet, Available at http://www.iontorrent.com/lib/images/PDFs/amplicon_application_note_040411.pdf, Apr. 4, 2011, pp. 1-5.
Jindal et al., "Suramin affects DNA Synthesis in HeLa Cells by Inhibition of DNA Polymerases", Cancer Research, 50, Dec. 15, 1990, pp. 7754-7757.
Jochmans et al., "Indolopyridones Inhibit Human Immunodeficiency Virus Reverse Transcriptase with a Novel Mechanism of Action", Journal of Virology, vol. 80, No. 24, Dec. 2006, pp. 12283-12292.
Kaplan, "Photolabile chelators for the rapid photorelease of divalent cations", Proc. Natl. Acad. Sci. USA, vol. 85, Sep. 1988, pp. 6571-6575.
Kaushik et al., "Biochemical Analysis of Catalytically Crucial Aspartate Mutants of Human Immunodeficiency Virus Type 1 Reverse Transcriptase", Biochemistry, 35, 1996, pp. 11536-11546.

(56) References Cited

OTHER PUBLICATIONS

Kim, "An FET-type charge sensor for highly sensitive detection of DNA sequence", Biosensors and Bioelectronics, Microsensors and Microsystems, 20, No. 1, Jul. 30, 2004, pp. 69-74.
Klenow et al., "Effect of Monovalent Cations on the Activity of the DNA Polymerase of Escherichia coli B", European J. Biochem., 1969, pp. 133-141.
Kumar et al., "Altered Order of Substrate Binding by DNA Polymerase X from African Swine Fever Virus", Biochemistry, 2008, pp. 7875-7887.
Leinbach et al., "Mechanism of phosphonoacetate inhibition of herpesvirus-induced DNA polymerase", Biochemistry, vol. 15, No. 2, 1976, pp. 426-430.
Lutz et al., "An in vitro screening technique for DNA polymerases that can incorporate modified nucleotides. Pseudothymidine as a substrate for thermostable polymerases", Nucleic Acids Research, vol. 27, No. 13, 1999, pp. 2792-2798.
Maga et al., "HIV-1 RT Inhibitors with a Novel Mechanism of Action: NNRTIs that Compete with the Nucleotide Substrate", Viruses, vol. 2, No. 4, 2010, pp. 880-899.
Maga et al., "Selective Interaction of the Human Immunodeficiency Virus Type 1 Reverse Transcriptase Nonnucleoside Inhibitor Efavirenz and Its Thio-Subsitituted Analog with Different Enzyme-Substrate Complexes", Antimicrobial Agents and Chemotherapy, vol. 44, No. 5, May 2000, pp. 1186-1194.
Mano, "Non-solid oncogenes in solid tumors: EML4-ALK fusion genes in lung cancer", Cancer Sci., vol. 99, 2008, pp. 2349-2355.
Markiewicz et al., "Single-Molecule Microscopy Reveals New Insights into Nucleotide Selection by DNA Polymerase I", Nucleic Acids Research, vol. 40, No. 16, Jun. 4, 2012, pp. 7975-7984.
Masheyekhi et al., "Analysis of Read-Length Limiting Factors in Pyrosequencing Chemistry", Anal Biochem, vol. 363, No. 3, Apr. 15, 2007, pp. 275-287.
Maxwell et al., "DNA Lesion Alters Global Conformational Dynamics of Y-family DNA Polymerase during Catalysis", The Journal of Biological Chemistry, vol. 287, No. 16, Apr. 13, 2012, pp. 13040-13047.
Namasivayam, "Light-Induced Molecular Cutting: Localized Reaction on a Single DNA Molecule", Anal. Chem., vol. 75, 2003, pp. 4118-4194.
Nath et al., "Label free colorimetric biosensing using nanoparticles", Journal of Fluorescence, vol. 14, No. 4, Jul. 2004, pp. 377-389.
Nazirizadeh, "Low-cost label-free biosensors using photonic crystals embedded between crossed polarizers", Optics Express, vol. 18, No. 18, Aug. 30, 2010, pp. 19120-19128.
Nikiforov, "Oligonucleotides labeled with single flurophores as sensors for deoxynucleotide triphosphate binding by DNA polymerases", Analytical Biochemistry 444, 2014, pp. 60-66.
Patel, "Insights into DNA Polymerization Mechanisms from Structure and Function Analysis of HIV-1 Reverse Transcriptase", Biochemistry 34, 1995, pp. 5351-5363.
Peletskaya et al., "Cross-Linking of the Fingers Subdomain of Human Immunodeficiency Virus Type 1 Reverse Transcriptase to Template-Primer", Journal of Virology, vol. 75, No. 19, Oct. 2001, pp. 9435-9445.
Pitta et al., "Synthesis and HIV-1 RT inhibitory action of novel (4/6-substituted benzo[d]thiazol-2-yl) thiazolidin-4-ones. Divergence from the non-competitive inhibition mechanism", J. Enzyme Inhib. Med. Chem., vol. 28, No. 10, 2013, pp. 113-122.
Potapova et al., "Interaction of dNTP, pyrophosphate and their analogs with the dNTP-binding sites of E. coli DNA polymerase I Klenow fragment and human DNA polymerase", FEBS letters, vol. 277, Issues 1-2, Dec. 17, 1990, pp. 194-196.
Puttaswamy, "Optical Method for Measuring Spatial pH Change on Conductive Microelectrodes", KTH, Royal Institute of Technology, Stockholm, Sweden.
Ren et al., "Inhibition of Klenow DNA polymerase and poly(A)-specific ribonuclease by aminoglycosides", RNA, vol. 8, 2002, pp. 1393-1400.
Richard et al., "Thermal stability landscape for Klenow DNA polymerase as a function of pH and salt concentration", Biochemica et Biophysica Acta, vol. 1764, 2006, pp. 1546-1552.
Roettger et al., "Mismatched and Matched dNTP Incorporation by DNA Polymerase β Proceed via Analogues Kinetic Pathways", Biochemistry, vol. 47, Sep. 16, 2008, pp. 9718-9727.
Santoso et al., "Conformational transitions in DNA polymerase I revealed by single-molecule FRET", Proceedings of the National Academy of Sciences, vol. 107, No. 2, Jan. 12, 2010, pp. 715-720.
Schadt et al., "Modeling Kinetic rate variation in third generation DNA sequencing data to detect putative modifications to DNA bases", Genome Research, 2013, pp. 129-141.
Schultz et al., "Single-target molecule detection with nonbleaching multicolor optical immunolabels", PNAS, vol. 96, No. 3, Feb. 1, 2000, pp. 996-1001.
Sen et al., "Intrinsic fluorescence of E. coli RNA polymerase as a probe for its conformational changes during transcription initiation", Biochem Biophys Res Commun, vol. 201, No. 2, Jun. 15, 1994, pp. 820-828.
Soda et al., "Identification of the transforming EML4-ALK fusion gene in non-small-cell lung cancer", Nature, vol. 228, Aug. 2, 2007, pp. 561-566.
Star et al., "Electronic Detection of Specific Protein Binding Using Nanotube FET Devices", Nano Letters 3, No. 4, Apr. 1, 2003, pp. 459-463.
Su, "Surface Plasmon Resonance Spectroscopy and Quartz Crystal Microbalance Study of Streptavidin Film Structure effects on Biotinylated DNA Assembly and Target DNA Hybridization", Langmuir, vol. 21, No. 1, 2005, pp. 348-353.
Tsai, "Dissertation", May 2005, pp. 1-131.
Tsai et al., "Site-specific labeling of T7 DNA polymerase with a conformationally sensitive flurophore and its use in detecting single-nucleotide polymorphisms", Analytical Biochemistry, vol. 384, No. 1, Academic Press Inc., New York, Jan. 1, 2009, pp. 136-144.
Vaidyanathan et al., "Binary and ternary binding affinities between exonuclease-deficient Klenow fragment (Kf-exo(-)) and various arylamine DNA lesions characterized by surface plasmon resonance", Chem Res Toxicol, vol. 25, No. 8, Aug. 20, 2012, pp. 1568-1570.
Vaidyanathan et al., "Binding kinetics of DNA-protein interaction using surface plasmon resonance", Protocol Exchange, May 22, 2013.
Vollmer et al., "Whispering-gallery-mode biosensing: label-free detection down to single molecules", Nature Methods, vol. 5, No. 7, Jul. 2008, pp. 591-596.
Walsh, "Synthetic Nucleotides as Probes of DNA Polymerase Specificity", Journal of Nucleic Acids, vol. 2012, Article ID 530963, 17 pages.
Washington et al., "Human DNA Polymerase Utilizes Different Nucleotide Incorporation Mechanisms Dependent upon the Template Base", Molecular and Cellular Biology, vol. 24, No. 2, Jan. 2004, pp. 936-943.
Xia et al., "DNA Mismatch Synthesis Complexes Provide Insights into Base Selectivity of a B family DNA Polymerase", J Am Chem Soc., vol. 135, No. 1, Jan. 9, 2013, pp. 193-202.
Yuzenkova et al., "Tagetitoxin inhibits transcription by stabilizing pre-translocated state of the elongation complex", Nucleic Acids Research, 2013, pp. 9257-9265.
JP2018-523734, "Office Action", dated Jan. 22, 2019, 20 pages.
AU2015402762, "First Examination Report", dated Sep. 9, 2019, 3 pages.
JP2018-523734, "Notice of Reasons for Rejection", dated Sep. 24, 2019, 10 pages.
CA2,992,980, "Office Action", dated Apr. 6, 2021, 4 pages.
CN201580081843.1, "Office Action", with English Translation, dated Dec. 7, 2020, 25 pages.
CA2,992,980, "Office Action", dated Mar. 3, 2022, 4 pages.

* cited by examiner

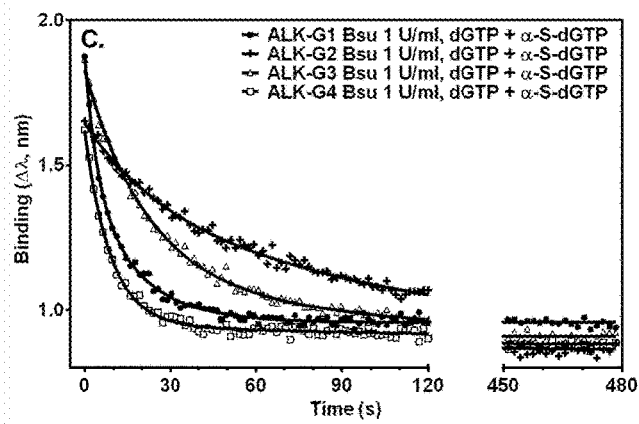
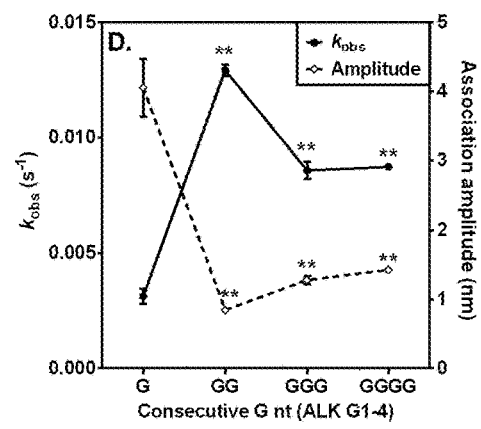
FIG. 18C
FIG. 18D
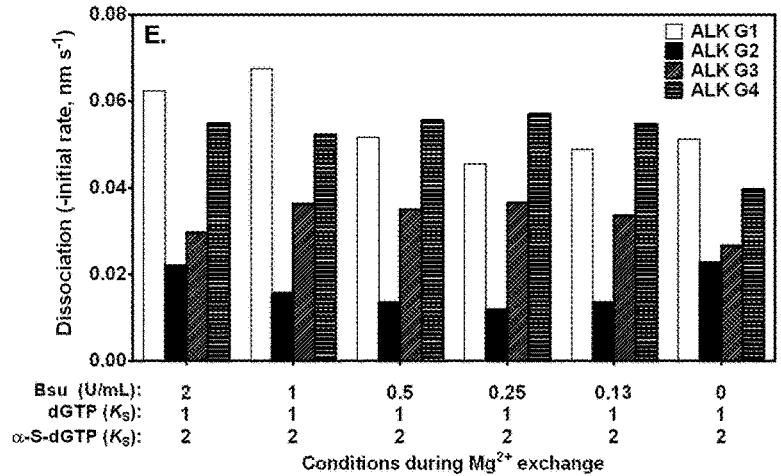
FIG. 18E

SEQUENCE LISTING

```
<160> NUMBER OF SEQ ID NOS: 40

<210> SEQ ID NO 1
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1 cagcagga                                                             8

<210> SEQ ID NO 2
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2 cagcagg                                                              7
```

<210> SEQ ID NO 3
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
ggcaaatcac cagaaggcgg ttcctgaatg aatgggaagc cttcaagaag gtgataagca      60
ggagaaacat acgaaggcgc ataacgatac cactgaccct c                         101

<210> SEQ ID NO 4
<211> LENGTH: 101
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
ggcaaatcac cagaaggcgg ttcctgaatg aatgggaagc cttcaagaag gtgataagca      60
ggagaaacat acgaagcatc ataacgatac cactgaccct c                         101

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gagggtcagt ggtatcgtta tg                                               22

<210> SEQ ID NO 6
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
tgataagcag gagaaacata cgaagcatca taacgatacc actgaccctc                 50

<210> SEQ ID NO 7
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gtgagcctgc aatccctgcc ccggttcatc ctgctggagc tcatggcggg                 50

<210> SEQ ID NO 8
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 8
cccgccatga gctc                                                        14

<210> SEQ ID NO 9
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (51)..(51)
<223> OTHER INFORMATION: Inverted dT

<400> SEQUENCE: 9
gtgagcctgc aatccctgcc ccggttcatc ctgctggagc tcatggcggg t              51

<210> SEQ ID NO 10
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cccgccatga gctc                                                        14

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (17)..(17)
<223> OTHER INFORMATION: 5-nitroindole-2'-deoxyribose

<400> SEQUENCE: 11
agcaggatga accgggncag ggattgcagg ctcac                                 35

<210> SEQ ID NO 12
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (25)..(25)
<223> OTHER INFORMATION: 5-nitroindole-2'-deoxyribose

<400> SEQUENCE: 12 tttttttag caggatgaac cgggncaggg attgcaggct cac                         43

<210> SEQ ID NO 13
<211> LENGTH: 8
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
``` cagcagca                                                              8

<210> SEQ ID NO 14
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
cagtcagtca gtcagtcagt cagtcagtca gtcagtcagt cagtcagtca gtc           53

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
cagcagcatc gcacgcagca tcgcccc                                        27

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
cagcaggatg aaccggggca gggattgcag gctcac                              36

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
cagcagagtg agcgcgcgcg ggg                                            23

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cagcaggatg aaccggggca gggattgcag gctcac                              36

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
cagcagatga cgcagag                                                   17

```
<210> SEQ ID NO 20
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
cagcaggatg aaccggggca gggattgcag gctcac                              36

<210> SEQ ID NO 21
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (51)..(51)
<223> OTHER INFORMATION: Inverted dT

<400> SEQUENCE: 21
gtgagcctgc aatccctgcc ccggttcatc ctgatggagc tcatggcggg t            51

<210> SEQ ID NO 22
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
ggcaaatcac cagaaggcgg ttcctgaatg aatgggaagc cttcaagaag gtgataagca   60
ggagaaacat acgaagcatc ataacgatac cactgaccc                          99

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
catcaggatg aaccggggca gggattgcag gc                                 32

<210> SEQ ID NO 24
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
catcaggatg aaccggggca gggattgcag gctcac                             36

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 25
catcagatga cgcagatgca gc                                          22

<210> SEQ ID NO 26
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cccgccatga gctcca                                                 16

<210> SEQ ID NO 27
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
cccgccatga gctccagca                                              19

<210> SEQ ID NO 28
<211> LENGTH: 34
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (29)..(29)
<223> OTHER INFORMATION: 2'-deoxyinosine

<400> SEQUENCE: 28
cccgccatga gctccagcag gatgaaccng ggca                             34

<210> SEQ ID NO 29
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
cccgccatga gctccagcag gatgaacc                                    28

<210> SEQ ID NO 30
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
cagcagcagc ag                                                     12

<210> SEQ ID NO 31
<211> LENGTH: 10
<212> TYPE: DNA

<213> ORGANISM: Artificial Sequence
<220> FEATURE:
<223> OTHER INFORMATION: Description of Artificial Sequence: Synthetic oligonucleotide

<400> SEQUENCE: 31
cagtcagtca                                                                        10

<210> SEQ ID NO 32
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 32
atgcttcgta tgtttctcct gcttatcacc ttc                                              33

<210> SEQ ID NO 33
<211> LENGTH: 43
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 33
atgctcatgc tcatgctcat gctcatgctc atgctcatgc tca                                   43

<210> SEQ ID NO 34
<211> LENGTH: 12
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 34
catcaggatg aa                                                                     12

<210> SEQ ID NO 35
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 35
ccaaggttcc aaggttccaa ggttccaagg ttcca                                            35

<210> SEQ ID NO 36
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 36
aaggttccaa ggttccaagg ttccaaggtt ccaag                                            35

<210> SEQ ID NO 37
<211> LENGTH: 35
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 37
ggttccaagg ttccaaggtt ccaaggttcc aaggt                                    35

<210> SEQ ID NO 38
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
cagtcagtca gt                                                             12

<210> SEQ ID NO 39
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
accggggcag ggattg                                                         16

<210> SEQ ID NO 40
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gcaggctcac                                                                10
```

NUCLEIC ACID SEQUENCING METHODS AND SYSTEMS

CROSS REFERENCE TO RELATED APPLICATIONS

This application is a continuation of U.S. application Ser. No. 14/805,381, filed Jul. 21, 2015 and entitled "NUCLEIC ACID SEQUENCING METHODS AND SYSTEMS", the entire contents of which are incorporated by reference herein.

SEQUENCE LISTING

The instant application contains a Sequence Listing which has been submitted electronically in ASCII format and is hereby incorporated by reference in its entirety. Said ASCII copy, created on Nov. 23, 2020, is named 097128-1096258-009US2_SL.txt and is 10,231 bytes in size.

BACKGROUND

The determination of nucleic acid sequence information is an important part of biological and medical research. The sequence information is helpful for identifying gene associations with diseases and phenotypes, identifying potential drug targets, and understanding the mechanisms of disease development and progress. Sequence information is an important part of personalized medicine, where it is can be used to optimize the diagnosis, treatment, or prevention of disease in a specific subject.

SUMMARY

Provided herein are methods for sequencing a template nucleic acid molecule. The method generally includes an examination step prior to incorporation of an unlabeled nucleotide. More specifically, the examination step includes providing a template nucleic acid molecule primed with a primer, contacting the primed template nucleic acid molecule with a first reaction mixture that includes a polymerase and at least one unlabeled nucleotide molecule, monitoring the interaction of the polymerase with the primed template nucleic acid molecule in the presence of the unlabeled nucleotide molecule, without chemical incorporation of the nucleotide molecule into the primed template nucleic acid, and identifying a next base in the template nucleic acid based on the monitored interaction of the polymerase with the primed template nucleic acid molecule in the presence of the unlabeled nucleotide molecule.

BRIEF DESCRIPTION OF THE DRAWINGS

FIG. 7A is a graph showing the time course for consecutive cycles of sequencing. FIG. 7A discloses SEQ ID NO: 30. FIG. 7B is a graph showing cycles 1-12 in individual panels after subtracting background from the previous cycle. The expected sequence read was CAGCAGGA (SEQ ID NO:1) and the observed sequence read was CAGCAGG (SEQ ID NO:2).

FIG. 11A: Single-stranded DNA. FIG. 11A discloses SEQ ID NO: 31. FIG. 11B: double-stranded DNA with one base gap. FIG. 11B discloses SEQ ID NO: 31. FIG. 11C: double-stranded DNA with a 5'-oligo-dT flap downstream of a one base pair gap.

FIG. 13 A is a sensorgram demonstrating sequencing in ssDNA mixtures of wild-type and C4493A mutant. FIG. 13B is a graph showing, in ssDNA mixtures, linear quantitation of C4493A mutant shown in Cycle 4 (T), and linear quantitation of wild-type ALK shown in cycle 3 (G). FIG. 13C is a graph showing, in dsDNA-flap mixtures, linear quantitation of C4493A mutant is shown in Cycle 4 (T), and roughly linear quantities of wild-type ALK are shown in cycle 3 (G).

FIG. 14A is a graph showing binding to the primer/template and dissociation in the presence of non-catalytic metals. FIG. 14B is a graph showing binding to the primer/template and dissociation in the presence of catalytic metals.

FIG. 15 discloses SEQ ID NOS 32, 33 and 33, respectively, in order of appearance.

FIG. 16 discloses SEQ ID NOS 34, 39, 35, 36, 40 and 37, respectively, in order of appearance.

FIG. 17A is a sensorgram of sequencing using the Octet QK system. FIG. 17B is a graph showing resolution of two consecutive G peaks is dependent upon the concentrations of dNDP in the Reaction Buffer. FIGS. 17A and 17B both disclose SEQ ID NO: 38.

FIGS. 18A, 18B, 18C, 18D and 18E are graphs showing homopolymer resolution during Bsu Pol I (large fragment) sequencing of human wild-type ALK. FIG. 18A is a sensogram of Ni enhanced binding of polymerase on templates ALK-G1, ALK-G2 and ALK-G3. FIG. 18B is a sensogram of Ni enhanced binding of polymerase on template ALK-G4. FIG. 18C is a sensogram of the incorporation/dissociation time following addition of reaction buffer containing Ni and Mg. FIG. 18D is a graph showing examination phase parameters plotted versus the number of G nucleotides in the primer strand needed to fill the C homopolymer of the template. Control is a single G incorporation (G), and "**" indicates statistically significant results with $p<0.01$. FIG. 18E is a graph showing initial rates observed during the incorporation/dissociation phase plotted for indicated Bsu polymerase concentrations. Control is a single G incorporation (G).

DETAILED DESCRIPTION

Figure 1:
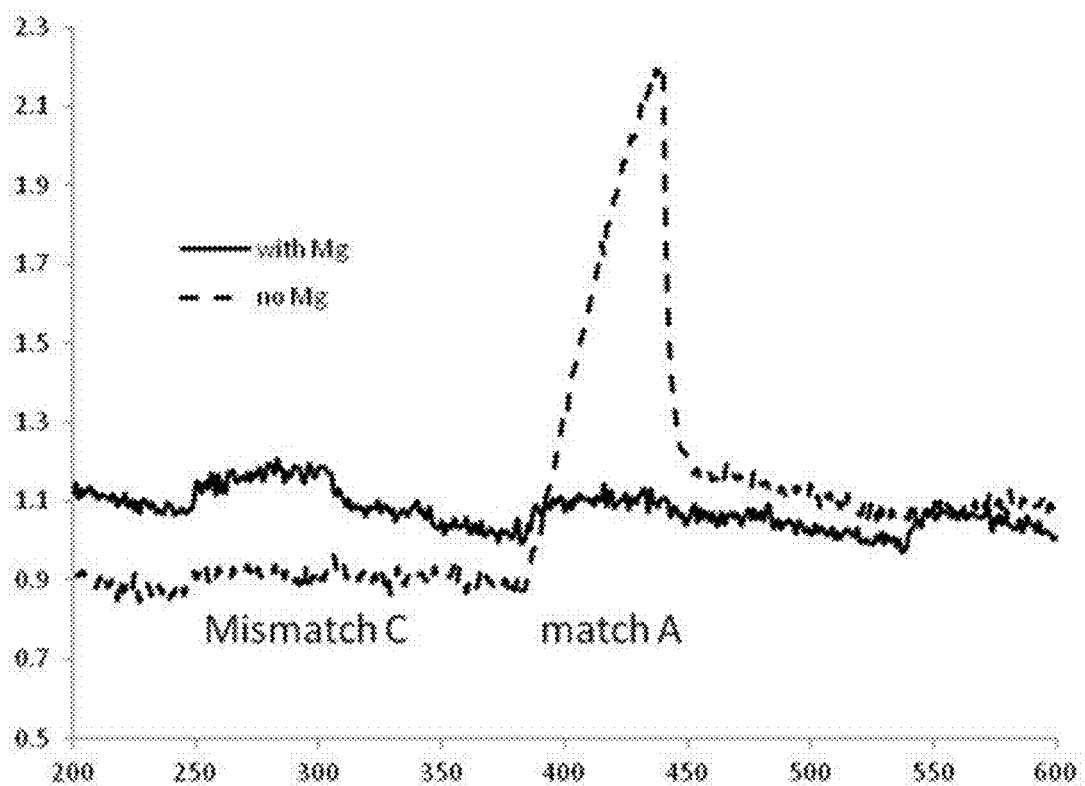
FIG. 1 is a graph showing the results of an experiment using non-labeled optical detection methods where magnesium was present or absent during the binding or examination step.

High-throughput, cost-effective nucleic acid sequencing has potential to usher in a new era of research and personalized medicine. Several commercial sequencing platforms are available, and, although they sequence on the scale of entire genomes, they are still prohibitively expensive for mass-market genetic analysis. By reducing sequencing costs, it will be possible to analyze genetic variation in detail between species and individuals, providing a basis for personalized medicine, as well as identifying links between genotypes and phenotypes. In addition to lower reagent and labor costs, goals for sequencing technologies include expanding throughput and improving accuracy.

Currently, a variety of sequencing technologies utilize a method known as sequencing by synthesis (SBS) or sequencing by incorporation. A common SBS method employs the use an enzyme such as a polymerase to synthesize a DNA strand complementary to a strand of DNA to be sequenced, by providing nucleotides or short oligonucleotides, which are modified with identifying tags, so that the base type of the incorporated nucleotide or oligonucleotide is detected as synthesis proceeds. Detection may be real-time wherein the nucleotides are detected as they are incorporated. Real-time procedures suffer from inaccurate reads of regions containing highly repetitive sequences and homopolymeric regions. Detection may also proceed in iterations of stop and proceed steps, wherein controlled reaction conditions and/or reagents reversibly stop and start the reaction at a given time during synthesis.

There are several systems and instruments that have been developed or are currently being developed to perform sequencing by synthesis methods. The methods use similar reaction approaches, with differences including the use of different identifying tags and/or the manner in which nucleotide incorporation is detected. These sequencing systems generally achieve rather short read lengths on the order of a hundred to a few hundred bases, but overcome this limitation by massive parallelization where many thousands of DNA segments are sequenced simultaneously on the same substrate.

As many sequencing by synthesis technologies are based on fluorescent detection, fluorescent labeling of nucleotides is required, which, along with the illumination and optics, causes the system to be complex and expensive. Fluorescence labeling techniques may be labor intensive and require a technologically intensive labeling process. Also, the quantification accuracy of fluorescence based methods may be poor due to the susceptibility of the fluorescence labels to photo-bleaching and spectral interferences from fluorescent impurities. In addition, some methods require the use of multiple fluorescent labels (i.e., one for each dATP, dCTP, dGTP, dTTP), each detected at a different wavelength, which adds to cost and detection instrumentation. By way of example, sequence by synthesis (SBS) methods often require fluorescently labeled dNTPs for detecting incorporated nucleotides and therefore identifying a template nucleic acid sequence; however, the use of labeled nucleotides has limitations on accuracy, as current SBS reactions using labeled nucleotides become error-prone after a few hundred bases. When an entire genome is to be sequenced, even a 1% error could compromise the significance of the sequencing results. Accuracy may be decreased when a failure to detect a single label results in a deletion error or when the detection of a stray molecule results in an insertion error. Fluorophores which are bleached cause false-negatives. In addition, contamination of labeled dNTPs by unlabeled dNTPs, e.g., impurities or hydrolysis products, can also cause false-negatives. In addition, stray signals from labeled dNTPs non-specifically bound to a structured surface contribute to insertion errors or high signal to noise ratios. The use of modified nucleotides significantly slows down enzyme kinetics, making the sequencing reaction very slow. Another challenge with labeled nucleotides is that the label needs to be removed or deactivated once it is detected, so that the next addition can be observed without background signal. Thus, to obtain long read-lengths, each addition must be followed by virtually 100% chemical, enzymatic or photolytic steps to unblock the substrate or remove the dye for the next addition.

The compositions, systems, and methods provided herein overcome or reduce one or more problems associated with current sequencing by synthesis methods. The provided methods can be carried out in the absence of detectably labeled nucleotides. Optionally, the method is carried out in the absence of any detectable labels, e.g., on the nucleotides, polymerase or templates being sequenced. The methods provided herein employ a sequence by binding reaction, comprising an examination step that identifies the next template base, and an incorporation step that adds one or more complementary nucleotides to the 3' end of the primer. The incorporation step may be concurrent or separate from the examination step. The examination step involves monitoring the interaction between a polymerase and a nucleic acid to be sequenced (template nucleic acid) in the presence of nucleotides. Optionally, the interaction may be in the presence of stabilizers, whereby the polymerase-nucleic acid interaction is stabilized by the stabilizers, in the presence of the next correct nucleotide. The examination step determines template nucleic acid base identity without the need for nucleotide incorporation and/or labeled nucleotides. The examination step may be controlled so that nucleotide incorporation is attenuated or accomplished. If nucleotide incorporation is attenuated, a separate incorporation step may be performed. The separate incorporation step may be accomplished without the need for monitoring, as the base has been identified during the examination step. If nucleotide incorporation proceeds during examination, subsequent nucleotide incorporation may be attenuated by a stabilizer that traps the polymerase on the nucleic acid after incorporation. A reversibly terminated nucleotide may also be used to prevent the addition of subsequent nucleotides. The sequencing by binding method allows for controlled determination of a template nucleic acid base without the need for labeled nucleotides, as the interaction between the polymerase and template nucleic acid can be monitored without a label on the nucleotide. The controlled nucleotide incorporation can also provide accurate sequence information of repetitive and homo-polymeric regions without necessitating the use of a labeled nucleotide. Therefore, in addition to improved accuracy, the compositions, systems, and methods provided herein are time and cost-effective, as they do not require labeled nucleotides necessary for fluorescence based SBS detection. As, further provided herein, template nucleic acid molecules may be sequenced under examination conditions, which do not require the use of template nucleic acid or polymerase attachment to a solid-phase support. The compositions, methods and systems herein provide numerous advantages over previous systems, such as controlled reaction conditions, unambiguous determination of sequence, long read lengths, low overall cost of reagents, and low instrument cost. The present disclosure will employ, unless otherwise indicated, conventional molecular biology and bio-sensor techniques, which are within the skill of the art. Unless defined otherwise, all technical and scientific terms used herein have the same meaning as is commonly understood by one of ordinary skill in the art.

Provided herein is a method for sequencing a template nucleic acid molecule. The method includes: an examination step, the examination step including providing a template nucleic acid molecule primed with a primer; contacting the primed template nucleic acid molecule with a first reaction mixture comprising a polymerase and at least one unlabeled nucleotide molecule; monitoring the interaction of the polymerase with the primed template nucleic acid molecule in the presence of the unlabeled nucleotide molecule and without chemical incorporation of the nucleotide molecule into the primed template nucleic acid; and identifying a next base in the template nucleic acid based on the monitored interaction. Optionally, the primer is an extendible primer. Optionally, the contacting occurs under conditions that stabilize the formation of a ternary complex formed between the polymerase, primed template nucleic acid molecule and nucleotide when the nucleotide is complementary to the next base of the primed template nucleic acid molecule. Optionally, the contacting occurs under conditions that favor formation of the ternary complex over formation of a binary complex that is capable of forming between the polymerase, primed template nucleic acid and nucleotide when the nucleotide is not complementary to the next base of the primed template nucleic acid molecule. Optionally, the identifying comprises identifying the nucleotide that is complementary to the next base of the primed template nucleic acid.

Provided is method for sequencing a template nucleic acid molecule, including an examination step including providing a template nucleic acid molecule primed with a primer; contacting the primed template nucleic acid molecule with a first reaction mixture comprising a polymerase and a first unlabeled nucleotide molecule, wherein the primed template nucleic acid molecule, the polymerase and the first unlabeled nucleotide molecule are capable of forming a ternary complex when the first unlabeled nucleotide molecule is complementary to a next base of the primed template nucleic acid molecule, wherein the primed template nucleic acid molecule and the polymerase are capable of forming a binary complex when the first unlabeled nucleotide molecule is not complementary to a next base of the primed template nucleic acid molecule. The method further includes monitoring the interaction of the polymerase with the primed template nucleic acid molecule in the presence of the first unlabeled nucleotide molecule, and without chemical incorporation of the first unlabeled nucleotide molecule into the primer of the primed template nucleic acid molecule; and identifying the nucleotide that is complementary to the next base of the primed template nucleic acid molecule by the monitored interaction. Optionally, the contacting occurs under conditions that stabilizes formation of the ternary complex and/or destabilizes formation of the binary complex. These steps can be repeated one or more times. For example, the contacting and monitoring steps can be repeated one or more times. Optionally, the contacting and monitoring steps are repeated using the first reaction mixture. Optionally, the contacting and monitoring steps are repeated using a second reaction mixture comprising the polymerase and a second unlabeled nucleotide molecule. Optionally, the contacting and monitoring steps are repeated using a third reaction mixture comprising the polymerase and a third unlabeled nucleotide molecule. Optionally, the contacting and monitoring steps are repeated using a fourth reaction mixture comprising the polymerase and a fourth unlabeled nucleotide molecule. Optionally, contacting occurs under conditions that destabilizes formation of the binary complex.

Also provided is a method for sequencing a template nucleic acid molecule, the method including an examination step including providing a template nucleic acid molecule primed with a primer; contacting the primed template nucleic acid molecule with a reaction mixture comprising an unlabeled polymerase, a first unlabeled nucleotide molecule and a second unlabeled nucleotide molecule, the first and second unlabeled nucleotide molecules being different and present in the reaction mixture at different concentrations, wherein the primed template nucleic acid molecule, the unlabeled polymerase and the first and/or second unlabeled nucleotide molecule are capable of forming a ternary complex when the first and/or second unlabeled nucleotide molecule is complementary to a next base of the primed template nucleic acid molecule, wherein the primed template nucleic acid molecule and the unlabeled polymerase are capable of forming a binary complex when the first and/or second unlabeled nucleotide molecule is not complementary to a next base of the primed template nucleic acid molecule. Optionally, the contacting occurs under conditions that stabilizes formation of the ternary complex. The method also includes monitoring the interaction of the unlabeled polymerase with the primed template nucleic acid molecule in the presence of the first and second unlabeled nucleotide molecules, and without chemical incorporation of the first or second unlabeled nucleotide molecules into the primer of the primed template nucleic acid molecule; and identifying the nucleotide that is complementary to the next base of the primed template nucleic acid molecule by the monitored interaction of step (c). Optionally, the reaction mixture further comprises a third unlabeled nucleotide molecule, wherein the third unlabeled nucleotide molecule is different from the first and second unlabeled nucleotide molecules and present in the reaction mixture at a different concentration than the first and second unlabeled nucleotide molecules. Optionally, the reaction mixture further comprises a fourth unlabeled nucleotide molecule, wherein the fourth unlabeled nucleotide molecule is different from the first, second and third unlabeled nucleotide molecules and present in the reaction mixture at a different concentration than the first, second and third unlabeled nucleotide molecules. Optionally, the first reaction mixture comprises one or more first unlabeled nucleotide molecules capable of incorporation and one or more first unlabeled nucleotide molecules incapable of incorporation into the primer of the primed template nucleic acid molecule. Optionally, the second reaction mixture comprises one or more second unlabeled nucleotide molecules capable of incorporation and one or more second unlabeled nucleotide molecules incapable of incorporation into the primer of the primed template nucleic acid molecule. Optionally, the third reaction mixture comprises one or more third unlabeled nucleotide molecules capable of incorporation and one or more third unlabeled nucleotide molecules incapable of incorporation into the primer of the primed template nucleic acid molecule. Optionally, the fourth reaction mixture comprises one or more fourth unlabeled nucleotide molecules capable of incorporation and one or more fourth unlabeled nucleotide molecules incapable of incorporation into the primer of the primed template nucleic acid molecule.

Optionally, the provided methods further include a wash step. The wash step can occur before or after any other step in the method. Optionally, the wash step is performed prior to the monitoring step and/or prior to the identifying step. Optionally, the wash step removes any binary complexes. Optionally, the wash step occurs under conditions that stabilizes the ternary complex. Optionally, the conditions include a stabilizing agent. Optionally, the stabilizing agent is a non-catalytic metal ion. Optionally, the non-catalytic metal ion is strontium, tin, or nickel. Optionally, the ternary complex has a half-life and wherein the wash step is performed for a duration shorter than the half-life of the ternary complex formed when an unlabeled nucleotide molecule provides a base that is complementary to the next base of the primed template nucleic acid molecule.

Optionally, further comprising a reloading step following step (d), the reloading step comprising contacting the primed template nucleic acid with a reloading mixture comprising the polymerase and the first or optional second, third and fourth unlabeled nucleotide molecule under conditions that stabilize the ternary complex.

Optionally, the herein provided methods further comprise an incorporation step. By way of example, the incorporation step includes incorporating a single unlabeled nucleotide complementary to the next base of the template nucleic acid into the primer of the primed template nucleic acid molecule. Optionally, the incorporation step comprises contacting the primed template nucleic acid molecule, polymerase and nucleotide with an incorporation reaction mixture. The incorporation reaction mixture, optionally, comprises a catalytic metal ion. The provided method may further include preparing the primed template nucleic acid molecule for a next examination step after the incorporation step. Optionally, the preparing includes subjecting the primed template nucleic acid or the nucleic acid/polymerase complex to one or more wash steps; a temperature change; a mechanical vibration; a pH change; or an optical stimulation. Optionally, the wash step comprises contacting the primed template nucleic acid or the primed template nucleic acid/polymerase complex with one of more buffers, detergents, protein denaturants, proteases, oxidizing agents, reducing agents, or other agents capable of releasing internal crosslinks within a polymerase or crosslinks between a polymerase and nucleic acid. Optionally, the method further comprises repeating the examination step and the incorporation step to sequence a template nucleic acid molecule. The examination step may be repeated one or more times prior to performing the incorporation step. Optionally, two consecutive examination steps comprise reaction mixtures with different unlabeled nucleotide molecules. Optionally, prior to incorporating the single unlabeled nucleotide into the primed template nucleic acid molecule, the first reaction mixture is replaced with a second reaction mixture comprising a polymerase and 1, 2, 3, or 4 types of unlabeled nucleotide molecules. Optionally, the nucleotide molecules are selected from dATP, dTTP, dCTP, and dGTP.

In the provided sequencing methods, the at least one unlabeled nucleotide comprises a 3' hydroxyl group, which can be, for example, a free 3' hydroxyl group. Optionally, the 3' hydroxyl group of the at least one unlabeled nucleotide molecule is modified to comprise a 3' terminator moiety. The 3' terminator moiety may be a reversible terminator or may be an irreversible terminator. Optionally, the reversible terminator of the at least one unlabeled nucleotide molecule is replaced or removed after the examination step.

In the sequencing methods provided herein, the polymerase interacts with the primed template nucleic acid molecule in the presence of the at least one unlabeled nucleotide molecule to form a closed-complex. Optionally, the unlabeled nucleotide molecule is a nucleotide complementary to a base of the template nucleic acid molecule that is downstream of a 3' end of the primer in the primed template nucleic acid molecule. Optionally, the unlabeled nucleotide molecule is a next correct nucleotide; wherein the next correct nucleotide is a nucleotide complementary to a base of the template nucleic acid molecule that is downstream of a 3' end of the primer in the primed template nucleic acid molecule and the closed-complex is a ternary closed-complex comprising the primed template nucleic acid molecule, the polymerase, and the next correct nucleotide. Optionally, the formation of a ternary closed-complex is favored over the formation of a binary complex between the primed template nucleic acid and the polymerase. The formation of the ternary closed-complex may be favored over the formation of the binary complex when the first reaction mixture comprises a high concentration of salt. Optionally, the first reaction mixture comprises 50 to 1500 mM of salt. The formation of the ternary closed-complex may be favored over the formation of the binary complex when the first reaction mixture comprises a buffer having a high pH. Optionally, the pH is from 7.4 to 9.0. For certain polymerases extracted from extremophile environments, the formation of the ternary closed-complex may be favored over the formation of binary complex when the first reaction mixture comprises a buffer having low pH. Optionally, the pH is from 4.0-7.0. The reaction temperature and/or organic and inorganic additives may also be used to modulate the affinity between the polymerase and primed template nucleic acid molecules.

In the sequencing methods provided herein, the first reaction mixture can include 1, 2, 3, or 4 types of unlabeled nucleotide molecules. Optionally, the nucleotides are selected from dATP, dTTP, dCTP, and dGTP. Optionally, the reaction mixture comprises one or more triphosphate nucleotides and one or more diphosphate nucleotides. Optionally, a closed-complex is formed between the primed template nucleic acid, the polymerase, and any one of the four unlabeled nucleotide molecules so that four types of closed-complexes may be formed. A closed-complex comprising the polymerase, primed template nucleic acid and a nucleotide can be referred to herein as a ternary closed-complex or a ternary complex. Ternary complex and ternary closed-complex are used herein interchangeably.

Monitoring the interaction of the polymerase with the primed template nucleic acid molecule in the presence of an unlabeled nucleotide molecule can include measuring association kinetics for the interaction between the primed template nucleic acid, the polymerase, and any one of the four unlabeled nucleotide molecules. Monitoring the interaction of the polymerase with the primed template nucleic acid molecule in the presence of an unlabeled nucleotide molecule can include measuring equilibrium binding constants between the polymerase and primed template nucleic acid molecule, i.e., equilibrium binding constants of polymerase to the template nucleic acid in the presence of any one of the four unlabeled nucleotides. Thus, for example, the monitoring comprises measuring the equilibrium binding constant of the polymerase to the primed template nucleic acid in the presence of any one of the four unlabeled nucleotides. Monitoring the interaction of the polymerase with the primed template nucleic acid molecule in the presence of an unlabeled nucleotide molecule includes measuring dissociation kinetics of the polymerase from the primed template nucleic acid in the presence of any one of the four unlabeled nucleotides. Optionally, monitoring the interaction of the polymerase with the primed template nucleic acid molecule in the presence of an unlabeled nucleotide molecule includes measuring dissociation kinetics of the dissociation of the closed-complex, i.e., dissociation of the primed template nucleic acid, the polymerase, and any one of the four unlabeled nucleotide molecules. Optionally, the measured association kinetics are different depending on the identity of the unlabeled nucleotide molecule. Optionally, the polymerase has a different affinity for each of the four types of unlabeled nucleotide molecules. Optionally, the polymerase has a different dissociation constant for each of the four types of unlabeled nucleotide molecules in each type of closed-complex. Association, equilibrium and dissociation kinetics are known and can be readily determined by one in the art. See, for example, Markiewicz et al., *Nucleic Acids Research* 40(16):7975-84 (2012); Xia et al., *J. Am. Chem. Soc.* 135(1):193-202 (2013); Brown et al., *J. Nucleic Acids*, Article ID 871939, 11 pages (2010); Washington, et al., *Mol. Cell. Biol.* 24(2):936-43 (2004); Walsh and Beuning, *J. Nucleic Acids*, Article ID 530963, 17 pages (2012); and Roettger, et al., *Biochemistry* 47(37):9718-9727 (2008), which are incorporated by reference herein in their entireties. Thus, the monitoring step can include monitoring the steady state interaction of the polymerase with the primed template nucleic acid molecule in the presence of the first unlabeled nucleotide molecule, without chemical incorporation of the first unlabeled nucleotide molecule into the primer of the primed template nucleic acid molecule. Optionally, the monitoring includes monitoring dissociation of the polymerase with the primed template nucleic acid molecule in the presence of the first unlabeled nucleotide molecule, without chemical incorporation of the first unlabeled nucleotide molecule into the primer of the primed template nucleic acid molecule. Optionally, the monitoring includes monitoring association of the polymerase with the primed template nucleic acid molecule in the presence of the first unlabeled nucleotide molecule, without chemical incorporation of the first unlabeled nucleotide molecule into the primer of the primed template nucleic acid molecule.

In the sequencing methods provided herein, the absence of a catalytic metal ion in the reaction mixture or the absence of a catalytic metal ion in the active site of the polymerase prevents the chemical incorporation of the nucleotide molecule to the primed template nucleic acid. Optionally, the chelation of a catalytic metal ion in the first reaction mixture prevents the chemical incorporation of the nucleotide molecule to the primed template nucleic acid. Optionally, the non-catalytic metal ion acts as a stabilizer for the ternary closed complex in the presence of the next correct nucleotide. Optionally, the substitution of a catalytic metal ion in the first reaction mixture with a non-catalytic metal ion prevents the chemical incorporation of the nucleotide molecule to the primed template nucleic acid. Optionally, the catalytic metal ion is magnesium. The metal ion mechanisms of polymerases postulates that, a low concentration of metal ions may be needed to stabilize the polymerase-nucleotide-DNA binding interaction. See, for instance, Section 27.2.2, Berg J M, Tymoczko J L, Stryer L, *Biochemistry 5th Edition*, WH Freeman Press, 2002. As used herein, catalytic metal ions refer to metal ions required for phosphodiester bond formation between the 3'OH of a nucleic acid (e.g., primer) and phosphate of incoming nucleotide. The concentrations of metal ion(s) refer to the quantity of metal ion(s) required for the phosphodiester bond formation between the 3'OH of a nucleic acid (e.g., primer) and phosphate of incoming nucleotide. Optionally, a low concentration of a catalytic ion in the first reaction mixture prevents the chemical incorporation of the nucleotide molecule to the primed template nucleic acid. Optionally, a low concentration is from about 1 μM to about 100 μM. Optionally, a low concentration is from about 0.5 μM to about 5 μM. Optionally, the first reaction mixture comprises cobalt and the incorporating comprises contacting with an incorporation reaction mixture comprising a higher concentration of cobalt as compared to the concentration of cobalt in the first reaction mixture.

Optionally, the provided reaction mixtures including the incorporation reaction mixtures include at least one unlabeled nucleotide molecule is a non-incorporable nucleotide or a nucleotide incapable of incorporation into the nucleic acid strand. In other words, the provided reaction mixtures can include one or more unlabeled nucleotide molecules incapable of incorporation into the primer of the primed template nucleic acid molecule. Such nucleotides incapable of incorporation include, for example, diphosphate nucleotides. For example, the nucleotide may contain modifications to the triphosphate group that make the nucleotide non-incorporable. Examples of non-incorporable nucleotides may be found in U.S. Pat. No. 7,482,120, which is incorporated by reference herein in its entirety. Optionally, the primer may not contain a free hydroxyl group at its 3' end, which is incapable of incorporating a nucleotide, and, thus making any nucleotide non-incorporable.

In the sequencing methods provided herein, the addition of a polymerase inhibitor to the first reaction mixture can be used, if desired, to trap the polymerase on the nucleic acid upon binding the next correct nucleotide. Optionally, the polymerase inhibitor is a pyrophosphate analog. Optionally, the polymerase inhibitor is an allosteric inhibitor. Optionally, the polymerase inhibitor competes with a catalytic-ion binding site in the polymerase. Optionally, the polymerase inhibitor is a reverse transcriptase inhibitor. The polymerase inhibitor may be a HIV-1 reverse transcriptase inhibitor or a HIV-2 reverse transcriptase inhibitor. The HIV-1 reverse transcriptase inhibitor may be a (4/6-halogen/MeO/EtO-substituted benzo[d]thiazol-2-yl)thiazolidin-4-one.

Optionally, the template nucleic acid is immobilized to a surface. The surface may be a planar substrate, a hydrogel, a nanohole array, a microparticle, or a nanoparticle. Optionally, the first reaction mixture comprises a plurality of clonally amplified template nucleic acid molecules. Optionally, the first reaction mixture comprises a plurality of distinguishable template nucleic acids.

As used herein, a nucleic acid is a polynucleotide, such as DNA, RNA, or any combination thereof, that can be acted upon by a polymerizing enzyme during nucleic acid synthesis. RNA may include coding RNA, e.g., a messenger RNA (mRNA). Optionally, the RNA is a non-coding RNA. Optionally, the non-coding RNA is a transfer RNA (tRNA), ribosomal RNA (rRNA), snoRNA, microRNA, siRNA, snRNA, exRNA, piRNA and long ncRNA. A nucleic acid may be single stranded or double stranded. Optionally, double stranded nucleic acids are advantageous as they minimize secondary structures that may hinder nucleic acid synthesis. A double stranded nucleic acid may possess a single-stranded nick or a gap. Sequencing can initiate from free 3'-hydroxyl ends by using polymerases with 5'-3' exonuclease activity (nick translation) or strand displacement activity. Optionally, different polymerases may be used for nick translation or strand displacement and sequencing by binding. Optionally, the double stranded nucleic acid may possess a single stranded nick or gap where the 5' end of the nick or gap is a single stranded flap. A nucleic acid may represent a single, plural or clonally amplified population of nucleic acid molecules.

A template nucleic acid is a nucleic acid to be sequenced using any sequencing method disclosed herein. A template nucleic acid may be primed with a primer, wherein the primer is an oligonucleotide that has a 5' end and a 3' end with a sequence that is complementary to at least a portion of the template nucleic acid. The primed template nucleic acid comprises the complementary primer bound to the template nucleic acid. Optionally, the template nucleic acid refers to the primed template nucleic acid, especially when referring to a complex between the template nucleic acid, polymerase and a nucleotide. The template nucleic acid nucleotide located immediately downstream of the 3' end of the primer bound to the template nucleic acid is referred to as the next template nucleotide or next base. A nucleotide complementary to the next base is referred to as the next correct nucleotide. A nucleotide which is not complementary to the next base is referred to as an incorrect nucleotide.

Optionally, the template is a double stranded nucleic acid molecule. Thus, also provided is a method for sequencing a double stranded nucleic acid molecule including an examination step including providing a double stranded nucleic acid molecule comprising a first template nucleic acid strand and a second nucleic acid strand comprising a nick or a gap; contacting the double stranded nucleic acid molecule with a first reaction mixture comprising a polymerase and at least one unlabeled nucleotide molecule under conditions that stabilize the formation of a ternary complex formed between the polymerase, double stranded nucleic acid molecule and nucleotide when the nucleotide is complementary to the next base of the first template nucleic acid strand; monitoring the interaction of the polymerase with the first template nucleic acid strand in the presence of the unlabeled nucleotide molecule without incorporation of the nucleotide molecule into the second strand; and identifying a next base in the template nucleic acid strand based on the monitored interaction. Optionally, the polymerase has strand-displacement activity. Optionally, the second strand of the double stranded nucleic acid molecule comprises a flap.

As used herein, a nucleotide refers to, a ribonucleotide, deoxyribonucleotide, nucleoside, modified nucleotide, or any monomer component that comprises the template nucleic acid or the nucleic acid being synthesized as part of the sequencing process. A nucleotide comprises a nitrogenous base, a five-carbon sugar (ribose or deoxyribose), and at least one phosphate group. Optionally, the phosphate group is modified with a moiety. The moiety may include a detectable label. Optionally, the 3' OH group of the nucleotide is modified with a moiety. The moiety may be a 3' reversible or irreversible terminator. A nucleotide may be adenine, cytosine, guanine, thymine, or uracil. Optionally, a nucleotide has an inosine, xanthanine, hypoxanthanine, isocytosine, isoguanine, nitropyrrole (including 3-nitropyrrole) or nitroindole (including 5-nitroindole) base. Nucleotides may include, but are not limited to, ATP, UTP, CTP, GTP, ADP, UDP, CDP, GDP, AMP, UMP, CMP, GMP, dATP, dTTP, dCTP, dGTP, dADP, dTDP, dCDP, dGDP, dAMP, dTMP, dCMP, and dGMP. Nucleotides may also contain terminating inhibitors of DNA polymerase, dideoxynucleotides or 2',3' dideoxynucleotides, which are abbreviated as ddNTPs (ddGTP, ddATP, ddTTP and ddCTP).

As used herein, a polymerase is a generic term for a nucleic acid synthesizing enzyme, including but not limited to, DNA polymerase, RNA polymerase, reverse transcriptase, primase and transferase. Typically, the polymerase comprises one or more active sites at which nucleotide binding and/or catalysis of nucleotide polymerization may occur. The polymerase may catalyze the polymerization of nucleotides to the 3' end of a primer bound to its complementary nucleic acid strand. For example, a polymerase catalyzes the addition of a next correct nucleotide to the 3' OH group of the primer via a phosphodiester bond, thereby chemically incorporating the nucleotide to the primer. Optionally, the polymerase used in the provided methods is a processive polymerase. Optionally, the polymerase used in the provided methods is a distributive polymerase.

Polymerases may include naturally-occurring polymerases and any modified variations thereof, including, but not limited to, mutants, recombinants, fusions, genetic modifications, chemical modifications, synthetics, and analogs. Naturally-occurring polymerases and modified variations thereof are not limited to polymerases that retain the ability to catalyze a polymerization reaction. Optionally, the naturally-occurring and/or modified variations thereof retain the ability to catalyze a polymerization reaction. Optionally, the naturally-occurring and/or modified variations have special properties that enhance their ability to sequence DNA, including enhanced binding affinity to nucleic acids, reduced binding affinity to nucleic acids, enhanced catalysis rates, reduced catalysis rates etc. Mutant polymerases include polymerases wherein one or more amino acids are replaced with other amino acids (naturally or non-naturally occurring), and insertions or deletions of one or more amino acids. Modified polymerases include polymerases that contain an external tag, which can be used to monitor the presence and interactions of the polymerase. Optionally, intrinsic signals from the polymerase can be used to monitor their presence and interactions. Thus, the provided methods can include monitoring the interaction of the polymerase, nucleotide and template nucleic acid through detection of an intrinsic signal from the polymerase. Optionally, the intrinsic signal is a light scattering signal. For example, intrinsic signals include native fluorescence of certain amino acids such as tryptophan, wherein changes in intrinsic signals from the polymerase may indicate the formation of a closed complex. Thus, in the provided methods, the polymerase is an unlabeled polymerase and monitoring is performed in the absence of a detectable label associated with the polymerase. Some modified polymerases or naturally occurring polymerases, under specific reaction conditions, may incorporate only single nucleotides and may remain bound to the primer-template after the incorporation of the single nucleotide. Optionally, the thumb and finger domains of the polymerase may form transient or covalent crosslinks due to their physical proximity in the closed form of the polymerase. The crosslinks may be formed, for example by native or engineered cysteines at suitable positions on the thumb and finger domains.

The term polymerase and its variants, as used herein, also refers to fusion proteins comprising at least two portions linked to each other, for example, where one portion comprises a peptide that can catalyze the polymerization of nucleotides into a nucleic acid strand is linked to another portion that comprises a second moiety, such as, a reporter enzyme or a processivity-modifying domain. For example, T7 DNA polymerase comprises a nucleic acid polymerizing domain and a thioredoxin binding domain, wherein thioredoxin binding enhances the processivity of the polymerase. Absent the thioredoxin binding, T7 DNA polymerase is a distributive polymerase with processivity of only one to a few bases. Although DNA polymerases differ in detail, they have a similar overall shape of a hand with specific regions referred to as the fingers, the palm, and the thumb; and a similar overall structural transition, comprising the movement of the thumb and/or finger domains, during the synthesis of nucleic acids.

DNA polymerases include, but are not limited to, bacterial DNA polymerases, eukaryotic DNA polymerases, archaeal DNA polymerases, viral DNA polymerases and phage DNA polymerases. Bacterial DNA polymerases include *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase. Eukaryotic DNA polymerases include DNA polymerases α, β, γ, δ, ε, η, ζ, λ, σ, μ, and k, as well as the Rev1 polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cpl DNA polymerase, Cpl DNA polymerase, T7 DNA polymerase, and T4 polymerase. Archaeal DNA polymerases include thermostable and/or thermophilic DNA polymerases such as DNA polymerases isolated from *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavusu* (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. go N-7 DNA polymerase; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; and the heterodimeric DNA polymerase DP1/DP2.

RNA polymerases include, but are not limited to, viral RNA polymerases such as T7 RNA polymerase, T3 polymerase, SP6 polymerase, and Kll polymerase; Eukaryotic RNA polymerases such as RNA polymerase I, RNA polymerase II, RNA polymerase III, RNA polymerase IV, and RNA polymerase V; and Archaea RNA polymerase.

Reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, and Telomerase reverse transcriptase that maintains the telomeres of eukaryotic chromosomes.

As used herein, a nucleotide analog may bind transiently to a polymerase-primed template nucleic acid complex, but is not incorporable (or substantially non-incorporable) in a nucleic acid polymerization reaction. As used herein, a nucleotide analog may bind to a polymerase-primed template nucleic acid complex, and become incorporated (or substantially incorporated) in a nucleic acid polymerization reaction. Nucleotide analogs may or may not have a structure similar to that of a native nucleotide comprising a nitrogenous base, five-carbon sugar, and phosphate group. Modified nucleotides may have modifications, such as moieties, which replace and/or modify any of the components of a native nucleotide. The non-incorporable nucleotides can be alpha-phosphate modified nucleotides, alpha-beta nucleotide analogs, beta-phosphate modified nucleotides, beta-gamma nucleotide analogs, gamma-phosphate modified nucleotides, caged nucleotides, or ddNTPs. Some examples of nucleotide analogs are described in U.S. Pat. No. 8,071,755, which is incorporated by reference herein in its entirety.

As referred to herein, a blocking moiety, when used to reference a nucleotide, is a part of the nucleotide that inhibits or prevents the nucleotide from forming a covalent linkage to a second nucleotide (e.g., the 3' OH of a primer nucleotide) during the incorporation step of a nucleic acid polymerization reaction. The blocking moiety can be removed from the nucleotide, allowing for nucleotide incorporation.

As used herein, a next correct nucleotide is a nucleotide that is complementary to the next base of the primed template nucleic acid downstream of the 3' end of the primer. An incorrect nucleotide is a nucleotide that is not complementary to the next base in the template nucleic acid downstream of the 3' end of the primer.

As used herein, a binary complex is a complex between a polymerase and a nucleic acid. Optionally, the nucleic acid is a template nucleic acid. Optionally, the nucleic acid is a primed template nucleic acid, wherein the polymerase binds to the polymerization site of the primed template nucleic acid at the 3' end of the primer. A complex may also form between a polymerase and a nucleotide referred to herein as a "polymerase-nucleotide complex" or "polymerase-nucleotide binary complex." As used herein, a ternary complex is a complex between a polymerase, a nucleic acid, and a nucleotide. Optionally, the nucleic acid is a template nucleic acid to be sequenced. Optionally, the nucleic acid in the ternary complex is a primed template nucleic acid, wherein the polymerase binds to the polymerization site of the primed template nucleic acid at the 3' end of the primer. Catalytic metal ions refers to metal ions that are required by polymerases to catalyze the reaction between the 3' OH group of a nucleic acid (e.g., a primer) and the phosphate group of an incoming nucleotide. Catalytic metal ions can be present at concentrations necessary to stabilize formation of a complex between a polymerase, nucleotide and nucleic acid, referred to as non-catalytic concentrations of a metal ion. Catalytic concentrations of a metal ion refer to the amount of a metal ion needed by polymerases to catalyze the reaction between the 3' OH group of a nucleic acid (e.g., a primer) and the phosphate group of an incoming nucleotide.

In the provided methods, contacting of the primed template nucleic acid molecule with a reaction mixture comprising a polymerase and one or more unlabeled nucleotide molecules can occur under conditions that stabilize formation of the ternary complex. Optionally, the contacting occurs under conditions that destabilizes formation of the binary complex. Optionally, the conditions comprise contacting the primed nucleic acid molecule with a buffer that regulates osmotic pressure. Optionally, the first reaction mixture comprises the buffer that regulates osmotic pressure. Optionally, the buffer is a high salt buffer. Optionally, the buffer comprises potassium glutamate. Optionally, the conditions that stabilize formation of the ternary complex comprise contacting the primed nucleic acid molecule with a stabilizing agent. Optionally, the first reaction mixture comprises a stabilizing agent. Optionally, the stabilizing agent is a non-catalytic metal ion. Optionally, the non-catalytic metal ion is strontium, tin, or nickel. Optionally, the first reaction mixture comprises from 0.01 mM to 30 mM strontium chloride.

Described herein, are polymerase-based, nucleic acid sequencing by binding reactions, wherein the polymerase undergoes conformational transitions between open and closed conformations during discrete steps of the reaction. In one step, the polymerase binds to a primed template nucleic acid to form a binary complex, also referred to herein as the pre-insertion conformation. In a subsequent step, an incoming nucleotide is bound and the polymerase fingers close, forming a pre-chemistry conformation comprising a polymerase, primed template nucleic acid and nucleotide; wherein the bound nucleotide has not been incorporated. This step, also referred to herein as an examination step, may be followed by a chemical step wherein a phosphodiester bond is formed with concomitant pyrophosphate cleavage from the nucleotide (nucleotide incorporation). The polymerase, primed template nucleic acid and newly incorporated nucleotide produce a post-chemistry, pre-translation conformation. As both the pre-chemistry conformation and the pre-translocation conformation comprise a polymerase, primed template nucleic acid and nucleotide, wherein the polymerase is in a closed state, either conformation may be referred to herein as a closed-complex or a ternary closed-complex. In the closed pre-insertion state, divalent catalytic metal ions, such as $Mg^{2+}$ mediate a rapid chemical step involving nucleophilic displacement of a pyrophosphate (PPi) by the 3' hydroxyl of the primer terminus. The polymerase returns to an open state upon the release of PPi, the post-translocation step, and translocation initiates the next round of reaction. While a closed-complex can form in the absence of a divalent catalytic metal ions (e.g., $Mg^{2+}$), it is proficient in chemical addition of nucleotide in the presence of the divalent metal ions. Low or deficient levels of catalytic metal ions, such as $Mg^{2+}$ tend to lead to non-covalent (physical) sequestration of the next correct nucleotide in a tight closed-complex. This closed-complex may be referred to as a stabilized or trapped closed-complex. In any reaction step described above, the polymerase configuration and/or interaction with a nucleic acid may be monitored during an examination step to identify the next correct base in the nucleic acid sequence.

As used herein, nucleic acid sequencing reaction mixtures, or reaction mixtures, comprise reagents that are commonly present in polymerase based nucleic acid synthesis reactions. Reaction mixture reagents include, but are not limited to, enzymes (e.g., polymerase), dNTPs, template nucleic acids, primer nucleic acids, salts, buffers, small molecules, co-factors, metals, and ions. The ions may be catalytic ions, divalent catalytic ions, non-catalytic ions, non-covalent metal ions, or a combination thereof. The reaction mixture can include salts such as NaCl, KCl, K-acetate, $NH_4$-acetate, K-glutamate, $NH_4Cl$, or $(NH_4HSO_4)$. The reaction mixture can include a source of ions, such as $Mg^{2+}$ or $Mn^{2+}$ Mg-acetate, $Co^{2+}$, $Cd^{2+}$ or $Ba^{2+}$. The reaction mixture can include tin, $Ca^{2+}$, $Zn^{2+}$, $Cu^{2+}$, $Co^{2+}$, $Fe(II)SO_4$, or $Ni^{2+}$. The buffer can include Tris, Tricine, HEPES, MOPS, ACES, MES, phosphate-based buffers, and acetate-based buffers. The reaction mixture can include chelating agents such as EDTA, EGTA, and the like. Optionally, the reaction mixture includes cross-linking reagents. Provided herein are first reaction mixtures, optionally, used during the examination step, as well as incorporation reaction mixtures used during nucleotide incorporation that can include one or more of the aforementioned agents. First reaction mixtures when used during examination can be referred to herein as examination reaction mixtures. Optionally, the first reaction mixture comprises a high concentration of salt; a high pH; 1, 2, 3, 4, or more types of unlabeled nucleotides; potassium glutamate; a chelating agent; a polymerase inhibitor; a catalytic metal ion; a non-catalytic metal ion; or any combination thereof. The first reaction mixture can include 10 mM to 1.6 M of potassium glutamate or any amount in between 10 mM and 1.6 M. Optionally, the incorporation reaction mixture comprises a catalytic metal ion; 1, 2, 3, 4, or more types of unlabeled nucleotides; potassium chloride; a non-catalytic metal ion; or any combination thereof.

As used herein, a closed-complex can be a ternary complex between a polymerase, primed template nucleic acid, and nucleotide. The closed-complex may be in a pre-chemistry conformation, wherein a nucleotide is sequestered but not incorporated. The closed-complex may be in a pre-translocation conformation, wherein a nucleotide is incorporated by formation of a phosphodiester bond with the 3' end of the primer in the primed template nucleic acid. The closed-complex may be formed in the absence of catalytic metal ions or deficient levels of catalytic metal ions, thereby physically sequestering the next correct nucleotide within the polymerase active site without chemical incorporation. Optionally, the sequestered nucleotide may be a non-incorporable nucleotide. The closed-complex may be formed in the presence of catalytic metal ions, where the closed-complex comprises a nucleotide analog which is incorporated, but a PPi is not capable of release. In this instance, the closed-complex is stabilized in a pre-translocation conformation. Optionally, a pre-translocation conformation is stabilized by chemically cross-linking the polymerase. Optionally, the closed-complex may be stabilized by external means. In some instances, the closed-complex may be stabilized by allosteric binding of small molecules. Optionally, closed-complex may be stabilized by pyrophosphate analogs, including, but not limited to, phosphonoformates, that bind close to the active site with high affinity, preventing translocation of the polymerase.

As used herein, a stabilized closed-complex or stabilized ternary complex refers to a polymerase trapped at the polymerization initiation site (3' end of the primer) of the primed template nucleic acid by one or a combinations of means, including but not limited to, crosslinking the thumb and finger domains in the closed conformation, binding of an allosteric inhibitor that prevents return of the polymerase to an open conformation, binding of pyrophosphate analogs that trap polymerase in the pre-translocation step, absence of catalytic metal ions in the active site of the polymerase, and addition of a metal ions such as nickel, barium, tin and strontium as substitutes for a catalytic metal ion. As such, the polymerase may be trapped at the polymerization initiation site even after the incorporation of a nucleotide. Therefore the polymerase may be trapped in the pre-chemistry conformation, pre-translocation step, post-translocation step or any intermediate step thereof. Thus, allowing for sufficient examination and identification of the next correct nucleotide or base.

As described herein, a polymerase-based, sequencing by binding reaction generally involves providing a primed template nucleic acid, providing the primed template nucleic acid with a polymerase and one or more types of nucleotides, wherein the nucleotides may or may not be complementary to the next base of the primed template nucleic acid, and examining the interaction of the polymerase with the primed template nucleic acid under conditions wherein either chemical incorporation of a nucleotide to the primed template nucleic acid is disabled or severely inhibited in the pre-chemistry conformation or one or more complementary nucleotide incorporation occurs at the 3' end of the primer. Optionally, wherein the pre-chemistry conformation is stabilized prior to nucleotide incorporation, preferably using stabilizers, a separate incorporation step may follow the examination step to incorporate a single nucleotide to the 3' end of the primer. Optionally, where a single nucleotide incorporation occurs, the pre-translocation conformation may be stabilized to facilitate examination and/or prevent subsequent nucleotide incorporation.

Whereas single template nucleic acid molecules may be described for ease of exposition, the sequencing methods provided herein readily encompass a plurality of template nucleic acids, wherein the plurality of nucleic acids may be clonally amplified copies of a single nucleic acid, or disparate nucleic acids, including combinations, such as populations of disparate nucleic acids that are clonally amplified.

The provided methods for sequencing a nucleic acid include an examination step. The examination step involves binding a polymerase to the polymerization initiation site of a primed template nucleic acid in a reaction mixture comprising one or more nucleotides, and monitoring the interaction. Optionally, a nucleotide is sequestered within the polymerase-primed template nucleic acid complex to form a closed-complex, under conditions in which incorporation of the enclosed nucleotide by the polymerase is attenuated or inhibited. Optionally a stabilizer is added to stabilize the ternary complex in the presence of the next correct nucleotide. This closed-complex is in a stabilized or polymerase-trapped pre-chemistry conformation. A closed-complex allows for the incorporation of the enclosed nucleotide but does not allow for the incorporation of a subsequent nucleotide. This closed-complex is in a stabilized or trapped pre-translocation conformation. Optionally, the polymerase is trapped at the polymerization site in its closed-complex by one or a combination of means, not limited to, crosslinking of the polymerase domains, crosslinking of the polymerase to the nucleic acid, allosteric inhibition by small molecules, uncompetitive inhibitors, competitive inhibitors, non-competitive inhibitors, and denaturation; wherein the formation of the trapped closed-complex provides information about the identity of the next base on the nucleic acid template.

The identity of the next correct base or nucleotide can be determined by monitoring the presence, formation, and/or dissociation of the ternary complex or closed-complex. The identity of the next base may be determined without chemically incorporating the next correct nucleotide to the 3' end of the primer. Optionally, the identity of the next base is determined by monitoring the affinity of the polymerase to the primed nucleic acid template in the presence of added nucleotides. Optionally, the affinity of the polymerase to the primed template nucleic acid in the presence of the next correct nucleotide may be used to determine the next correct base on the template nucleic acid. Optionally, the affinity of the polymerase to the primed nucleic acid template in the presence of an incorrect nucleotide may be used to determine the next correct base on the template nucleic acid.

The examination step may be controlled, in part, by providing reaction conditions to prevent chemical incorporation of a nucleotide, while allowing determination of the identity of the next base on the nucleic acid. Such reaction conditions may be referred to as examination reaction conditions. Optionally, a ternary complex or closed-complex is formed under examination conditions. Optionally, a stabilized ternary complex or closed-complex is formed under examination conditions or in a pre-chemistry conformation. Optionally, a stabilized closed-complex is in a pre-translocation conformation, wherein the enclosed nucleotide has been incorporated, but the closed-complex does not allow for the incorporation of a subsequent nucleotide. Optionally, the examination conditions accentuate the difference in affinity for polymerase to primed template nucleic acids in the presence of different nucleotides. Optionally, the examination conditions cause differential affinity of the polymerase to the primed template nucleic acid in the presence of different nucleotides. By way of example, the examination conditions that cause differential affinity of the polymerase to the primed template nucleic acid in the presence of different nucleotides include, but are not limited to, high salt and potassium glutamate. Concentrations of potassium glutamate that can be used to alter polymerase affinity to the primed template nucleic acid include 10 mM to 1.6 M of potassium glutamate or any amount in between 10 mM and 1.6 M. Optionally, high salt refers to a concentration of salt from 50 to 1500 mM salt.

Examination typically comprises detecting polymerase interaction with a template nucleic acid. Detection may include optical, electrical, thermal, acoustic, chemical and mechanical means. Optionally, examination is performed after a wash step, wherein the wash step removes any non-bound reagents, e.g., unbound polymerases and/or nucleotides, from the region of observation. Optionally, examination is performed during a wash step, such that the dissociation kinetics of the polymerase-nucleic acid or polymerase-nucleic acid-nucleotide complexes may be used to determine the identity of the next base. Optionally, examination is performed during the course of addition of the examination reaction mixture or first reaction mixture, such that the association kinetics of the polymerase to the nucleic acid may be used to determine the identity of the next base on the nucleic acid. Optionally, examination involves distinguishing closed-complexes from binary complexes of polymerase and nucleic acid. Optionally, examination is performed under equilibrium conditions where the affinities measured are equilibrium affinities. Multiple examination steps comprising different or similar examination reagents, may be performed sequentially to ascertain the identity of the next template base. Multiple examination steps may be utilized in cases where multiple template nucleic acids are being sequenced simultaneously in one sequencing reaction, wherein different nucleic acids react differently to the different examination reagents. Optionally, multiple examination steps may improve the accuracy of next base determination.

The sequencing methods described herein, optionally, involve an incorporation step. The incorporation step involves chemically incorporating one or more nucleotides at the 3' end of a primer bound to a template nucleic acid. Optionally, a single nucleotide or multiple nucleotides is incorporated at the 3' end of the primer. Optionally, multiple nucleotides of the same kind are incorporated at the 3' end of the primer. Optionally, multiple nucleotides of different kinds are incorporated at the 3' end of the primer. The polymerase can dissociate from the polymerization initiation site after nucleotide incorporation or can be retained at the polymerization initiation site after incorporation. Thus, for example, the polymerase may be trapped at the 3' end of the primer after the incorporation reaction in the pre-translocation state, post-translocation state, an intermediate state thereof, or a binary complex state. The incorporation reaction may be enabled by an incorporation reaction mixture. Optionally, the incorporation reaction mixture comprises a different composition of nucleotides than the examination reaction. For example, the examination reaction comprises one type of nucleotide and the incorporation reaction comprises another type of nucleotide. By way of another example, the examination reaction comprises one type of nucleotide and the incorporation reaction comprises four types of nucleotides, or vice versa. Optionally, the examination reaction mixture is altered or replaced by the incorporation reaction mixture. Optionally, the incorporation reaction mixture comprises a catalytic metal ion, potassium chloride, or a combination thereof.

Nucleotides present in the reaction mixture but not sequestered in a closed-complex may cause multiple nucleotide insertions. Thus, a wash step can be employed prior to the chemical incorporation step to ensure only the nucleotide sequestered within a trapped closed-complex is available for incorporation during the incorporation step. Optionally, free nucleotides may be removed by enzymes such as phosphatases. The trapped polymerase complex may be a closed-complex, a stabilized closed-complex or ternary complex involving the polymerase, primed template nucleic acid and next correct nucleotide.

Optionally, the nucleotide enclosed within the closed-complex of the examination step is incorporated into the 3' end of the template nucleic acid primer during the incorporation step. For example, a stabilized closed-complex of the examination step comprises an incorporated next correct nucleotide. Optionally, the nucleotide enclosed within the closed-complex of the examination step is incorporated during the examination step, but the closed-complex does not allow for the incorporation of a subsequent nucleotide; in this instance, the closed-complex is released during an incorporation step, allowing for a subsequent nucleotide to become incorporated.

Optionally, the incorporation step comprises replacing a nucleotide from the examination step (e.g., the nucleotide is an incorrect nucleotide) and incorporating another nucleotide into the 3' end of the template nucleic acid primer. The incorporation step can comprise releasing a nucleotide from within a closed-complex (e.g., the nucleotide is a modified nucleotide or nucleotide analog) and incorporating a nucleotide of a different kind to the 3' end of the template nucleic acid primer. Optionally, the released nucleotide is removed and replaced with an incorporation reaction mixture comprising a next correct nucleotide.

Suitable reaction conditions for incorporation may involve replacing the examination reaction mixture with an incorporation reaction mixture. Optionally, nucleotides present in the examination reaction mixture are replaced with one or more nucleotides in the incorporation reaction mixture. Optionally, the polymerase present during the examination step is replaced during the incorporation step. Optionally, the polymerase present during the examination step is modified during the incorporation step. Optionally, the one or more nucleotides present during the examination step are modified during the incorporation step. The reaction mixture and/or reaction conditions present during the examination step may be altered by any means during the incorporation step. These means include, but are not limited to, removing reagents, chelating reagents, diluting reagents, adding reagents, altering reaction conditions such as conductivity or pH, and any combination thereof. The reagents in the reaction mixture including any combination of polymerase, primed template nucleic acid, and nucleotide and each may be modified during the examination step and/or incorporation step.

Optionally, the incorporation step comprises competitive inhibitors, wherein the competitive inhibitors reduce the occurrence of multiple incorporations. In an embodiment, the competitive inhibitor is a non-incorporable nucleotide. In an embodiment, the competitive inhibitor is an aminoglycoside. The competitive inhibitor is capable of replacing either the nucleotide or the catalytic metal ion in the active site, such that after the first incorporation the competitive inhibitor occupies the active site preventing a second incorporation. In some embodiments, both an incorporable nucleotide and a competitive inhibitor are introduced in the incorporation step, such that the ratio of the incorporable nucleotide and the inhibitor can be adjusted to ensure incorporation of a single nucleotide at the 3' end of the primer.

In the provided sequencing methods, the next base is identified before the incorporation step, allowing the incorporation step to not require labeled reagents and/or monitoring. Thus, in the provided methods, a nucleotide, optionally, does not contain an attached detectable tag or label. Optionally, the nucleotide contains a detectable label, but the label is not detected in the method. Optionally, the correct nucleotide does not contain a detectable label; however, an incorrect or non-complementary nucleotide to the next base contains a detectable label.

The examination step of the sequencing reaction may be repeated 1, 2, 3, 4 or more times prior to the incorporation step. The examination and incorporation steps may be repeated until the desired sequence of the template nucleic acid is obtained.

The formation of the closed-complex or the stabilized closed-complex can be employed to ensure that only one nucleotide is added to the template nucleic acid primer per cycle of sequencing, wherein the added nucleotide is sequestered within the closed-complex. The controlled incorporation of a single nucleotide per sequencing cycle enhances sequencing accuracy for nucleic acid regions comprising homopolymer repeats.

Optionally, in the provided methods, following one or more examination and/or incorporation steps a subset of nucleotides is added to reduce or reset phasing. Thus, the methods can include one or more steps of contacting a template nucleic acid molecule being sequenced with a composition comprising a subset of nucleotides and an enzyme for incorporating the nucleotides into the strand opposite the template strand of the nucleic acid molecule. The contacting can occur under conditions to reduce phasing in the nucleic acid molecule. Optionally, the step of contacting the template nucleic acid molecule occurs after an incorporation step and/or after an examination step. Optionally, the contacting occurs after 1, 2, 3, 4, 5, 6, 7, 8, 9, 10, 15, 20, 25, 30, 35, 40, 45, 50, 60, 65, 70, 75, 80, 85, 90, 95, or 100 rounds or more of sequencing, i.e., rounds of examination and incorporation. Optionally, the contacting occurs after 30 to 60 rounds of sequencing. Optionally, the contacting occurs after every round of sequencing, i.e., after one examination and incorporation step. Optionally, multiple contacting steps occur after every round of sequencing, wherein each contacting step may comprise different subsets of nucleotides. Optionally, the method further comprises one or more washing steps after contacting. Optionally, the subset comprises two or three nucleotides. Optionally, the subset comprises three nucleotides. Optionally, the subset of nucleotides is selected from three of dATP, dGTP, dCTP, dTTP or a derivative thereof. Optionally, the three nucleotides comprise adenosine, cytosine, and guanine. Optionally, the three nucleotides comprise adenosine, cytosine, and thymine. Optionally, the three nucleotides comprise cytosine, guanine and thymine. Optionally, the three nucleotides comprise adenosine, guanine and thymine. Optionally, each round of contacting comprises the same subset or different subsets of nucleotides. Optionally, sequencing of a nucleic acid template is monitored and the contacting with the subset of nucleotides occurs upon detection of phasing. See also for example, U.S. Pat. No. 8,236,532, which is incorporated herein by reference in its entirety.

Optionally, the sequencing reaction involves a plurality of template nucleic acids, polymerases and/or nucleotides, wherein a plurality of closed-complexes is monitored. Clonally amplified template nucleic acids may be sequenced together wherein the clones are localized in close proximity to allow for enhanced monitoring during sequencing. Optionally, the formation of a closed-complex ensures the synchronicity of base extension across a plurality of clonally amplified template nucleic acids. The synchronicity of base extension allows for the addition of only one base per sequencing cycle.

The provided methods can be performed on a platform, where any component of the nucleic acid polymerization reaction is localized to a surface. Optionally, the template nucleic acid is attached to a planar substrate, a nanohole array, a microparticle, or a nanoparticle. Optionally, all reaction components are freely suspended in the reaction mixture.

The provided methods are conducted under reaction conditions that modulate the formation and stabilization of a closed-complex during an examination step. The reaction conditions of the examination step favor the formation and/or stabilization of a closed-complex encapsulating a nucleotide and hinder the formation and/or stabilization of a binary complex. The binary interaction between the polymerase and template nucleic acid may be manipulated by modulating sequencing reaction parameters such as ionic strength, pH, temperature, or any combination thereof, or by the addition of a binary complex destabilizing agent to the reaction. Optionally, high salt (e.g., 50 to 1500 mM) and/or pH changes are utilized to destabilize a binary complex. Optionally, a binary complex may form between a polymerase and a template nucleic acid during the examination or incorporation step of the sequencing reaction, regardless of the presence of a nucleotide. Optionally, the reaction conditions favor the stabilization of a ternary closed-complex and destabilization of a binary complex. By way of example, the pH of the examination reaction mixture can be adjusted from 4.0 to 10.0 to favor the stabilization of a ternary closed-complex and destabilization of a binary complex. Optionally, the pH of the examination reaction mixture is from 4.0 to 6.0. Optionally, the pH of the examination reaction mixture is 6.0 to 10.0.

The provided sequencing methods disclosed herein promote polymerase interaction with the nucleotides and template nucleic acid in a manner that reveals the identity of the next base while controlling the chemical addition of a nucleotide. Optionally, the methods are performed in the absence of detectably labeled nucleotides or in the presence of labeled nucleotides wherein the labels are not detected.

Provided herein are methods for the formation and/or stabilization of a closed-complex comprising a polymerase bound to a primed template nucleic acid and a nucleotide enclosed within the polymerase-template nucleic acid complex, under examination reaction mixture conditions. Examination reaction conditions may inhibit or attenuate nucleotide incorporation. Optionally, incorporation of the enclosed nucleotide is inhibited and the complex is stabilized or trapped in a pre-chemistry conformation or a ternary complex. Optionally, the enclosed nucleotide is incorporated and a subsequent nucleotide incorporation is inhibited. In this instance, the complex is stabilized or trapped in a pre-translocation conformation. For the sequencing reactions provided herein, the closed-complex is stabilized during the examination step, allowing for controlled nucleotide incorporation. Optionally, a stabilized closed-complex is a complex wherein incorporation of an enclosed nucleotide is attenuated, either transiently (e.g., to examine the complex and then incorporate the nucleotide) or permanently (e.g., for examination only) during an examination step. Optionally, a stabilized closed-complex allows for the incorporation of the enclosed nucleotide, but does not allow for the incorporation of a subsequent nucleotide. Optionally, the closed-complex is stabilized in order to monitor any polymerase interaction with a template nucleic acid in the presence of a nucleotide for identification of the next base in the template nucleic acid.

Optionally, the enclosed nucleotide has severely reduced or disabled binding to the template nucleic acid in the closed-complex. Optionally, the enclosed nucleotide is base-paired to the template nucleic acid at a next base. Optionally, the identity of the polymerase, nucleotide, primer, template nucleic acid, or any combination thereof, affects the interaction between the enclosed nucleotide and the template nucleic acid in the closed-complex.

Optionally, the enclosed nucleotide is bound to the polymerase of the closed-complex. Optionally, the enclosed nucleotide is weakly associated with the polymerase of the closed-complex. Optionally, the identity of the polymerase, nucleotide, primer, template nucleic acid, or any combination thereof, affects the interaction between the enclosed nucleotide and the polymerase in the closed-complex. For a given polymerase, each nucleotide has a different affinity for the polymerase than another nucleotide. Optionally, this affinity is dependent, in part, on the template nucleic acid and/or the primer.

The closed-complex may be transiently formed. Optionally, the enclosed nucleotide is a next correct nucleotide. In some methods, the presence of the next correct nucleotide contributes, in part, to the stabilization of a closed-complex. Optionally, the enclosed nucleotide is not a next correct nucleotide.

Optionally, the examination reaction condition comprises a plurality of primed template nucleic acids, polymerases, nucleotides, or any combination thereof. Optionally, the plurality of nucleotides comprises 1, 2, 3, 4, or more types of different nucleotides, for example dATP, dTTP, dGTP, and dCTP. Optionally, the plurality of template nucleic acids is a clonal population of template nucleic acids.

The examination reaction mixture can include other molecules including, but not limited to, enzymes. Optionally, the examination reaction mixture comprises any reagents or biomolecules generally present in a nucleic acid polymerization reaction. Reaction components may include, but are not limited to, salts, buffers, small molecules, detergents, crowding agents, metals, and ions. Optionally, properties of the reaction mixture may be manipulated, for example, electrically, magnetically, and/or with vibration.

Optionally, the closed-complex is transiently formed during the examination step of the sequencing methods provided herein. Optionally, the closed-complex is stabilized during the examination step. The stabilized closed-complex may not allow for the incorporation of a nucleotide in a polymerization reaction during the examination step, this includes incorporation of the enclosed nucleotide and/or incorporation of a subsequent nucleotide after the enclosed nucleotide. Reaction conditions that may modulate the stability of a closed-complex include, but are not limited to, the availability of catalytic metal ions, suboptimal or inhibitory metal ions, ionic strength, pH, temperature, polymerase inhibitors, cross-linking reagents, and any combination thereof. Reaction reagents which may modulate the stability of a closed-complex include, but are not limited to, non-incorporable nucleotides, incorrect nucleotides, nucleotide analogs, modified polymerases, template nucleic acids with non-extendible polymerization initiation sites, and any combination thereof.

Optionally, a closed-complex is released from its trapped or stabilized conformation, which may allow for nucleotide incorporation to the 3' end of the primer in the primer-template nucleic acid duplex. The closed-complex can be destabilized and/or released by a modulating the composition of the reaction conditions. In addition, the closed-complex can be destabilized by electrical, magnetic, and/or mechanical means. Mechanical means include mechanical agitation, for example, by using ultrasound agitation. Mechanical vibration destabilizes the closed-complex and suppresses binding of the polymerase to the DNA. Thus, rather than a wash step where the examination reaction mixture is replaced with an incorporation mixture, mechanical agitation may be used to remove the polymerase from the template nucleic acid, enabling cycling through successive incorporation steps with a single nucleotide addition per step.

Any combination of closed-complex stabilization or closed-complex release reaction conditions and/or methods may be combined. For example, a polymerase inhibitor which stabilizes a closed-complex may be present in the examination reaction with a catalytic ion, which functions to release the closed-complex. In the aforementioned example, the closed-complex may be stabilized or released, depending on the polymerase inhibitor properties and concentration, the concentration of the catalytic metal ion, other reagents and/or conditions of the reaction mixture, and any combination thereof.

The closed-complex can be stabilized under reaction conditions where covalent attachment of a nucleotide to the 3' end of the primer in the primed template nucleic acid is attenuated. Optionally, the closed-complex is in a pre-chemistry conformation or ternary complex. Optionally, the closed-complex is in a pre-translocation conformation. The formation of this closed-complex can be initiated and/or stabilized by modulating the availability of a catalytic metal ion that permits closed-complex release and/or chemical incorporation of a nucleotide to the primer in the reaction mixture. Exemplary metal ions include, but are not limited to, magnesium, manganese, cobalt, and barium. Catalytic ions may be any formulation, for example, salts such as $MgCl_2$, $Mg(C_2H_3O_2)_2$, and $MnCl_2$.

The selection and/or concentration of the catalytic metal ion may be based on the polymerase and/or nucleotides in the sequencing reaction. For example, the HIV reverse transcriptase utilizes magnesium for nucleotide incorporation (N Kaushik 1996 Biochemistry 35:11536-11546, and H P Patel 1995 Biochemistry 34:5351-5363, which are incorporated by reference herein in their entireties). The rate of closed-complex formation using magnesium versus manganese can be different depending on the polymerase and the identity of the nucleotide. Thus, the stability of the closed-complex may differ depending on catalytic metal ion, polymerase, and/or nucleotide identity. Further, the concentration of catalytic ion necessary for closed-complex stabilization may vary depending on the catalytic metal ion, polymerase, and/or nucleotide identity and can be readily determined using the guidance provided herein. For example, nucleotide incorporation may occur at high catalytic ion concentrations of one metal ion but does not occur at low concentrations of the same metal ion, or vice versa. Therefore, modifying metal ion identity, metal ion concentration, polymerase identity, and/or nucleotide identity allows for controlled examination reaction conditions.

The closed-complex may be formed and/or stabilized by sequestering, removing, reducing, omitting, and/or chelating a catalytic metal ion during the examination step of the sequencing reaction so that closed-complex release and/or chemical incorporation does not occur. Chelation includes any procedure that renders the catalytic metal ion unavailable for nucleotide incorporation, including using EDTA and/or EGTA. A reduction includes diluting the concentration of a catalytic metal ion in the reaction mixture. The reaction mixture can be diluted or replaced with a solution comprising a non-catalytic ion, which permits closed-complex formation, but inhibits nucleotide incorporation. Non-catalytic ions include, but are not limited to, calcium, strontium, scandium, titanium, vanadium, chromium, iron, cobalt, nickel, copper, zinc, gallium, germanium, arsenic, selenium, rhodium, and strontium. Optionally, $Ni^{2+}$ is provided in an examination reaction to facilitate closed-complex formation. Optionally, $Sr^{2+}$ is provided in an examination reaction to facilitate closed-complex formation. Optionally, a non-catalytic metal ion and a catalytic metal ion are both present in the reaction mixture, wherein one ion is present in a higher effective concentration than the other. In the provided methods, a non-catalytic ion such as, cobalt can become catalytic, i.e., facilitate nucleotide incorporation at high concentrations. Thus, optionally, a low concentration of a non-catalytic metal ion is used to facilitate ternary complex formation and a higher concentration of the non-catalytic metal ion is used to facilitate incorporation.

Non-catalytic ions may be added to a reaction mixture under examination conditions. The reaction may already include nucleotides. Optionally, non-catalytic ions are complexed to one or more nucleotides and complexed nucleotides are added to the reaction mixture. Non-catalytic ions can complex to nucleotides by mixing nucleotides with non-catalytic ions at elevated temperatures (about 80° C.). For example, a chromium nucleotide complex may be added to a mixture to facilitate closed-complex formation and stabilization. Optionally, a chromium nucleotide complex is a chromium monodentate, bidentate, or tridentate complex. Optionally, a chromium nucleotide complex is an α-monodentate, or β-γ-bidentate nucleotide.

Optionally, a closed-complex is formed between a polymerase, primed template nucleic acid, and nucleotide in reaction conditions comprising $Sr^{2+}$ wherein $Sr^{2+}$ induces the formation of the closed-complex. The presence of $Sr^{2+}$ can allow for the favorable formation of a closed-complex comprising a next correct nucleotide over the formation a complex comprising an incorrect nucleotide. $Sr^{2+}$ may be present at concentrations from about 0.01 mM to about 30 mM. Optionally, $Sr^{2+}$ is present as 10 mM $SrCl_2$. The formation of the closed-complex is monitored under examination conditions to identify the next base in the template nucleic acid of the closed-complex. The affinity of the polymerase (e.g., Klenow fragment of *E. coli* DNA polymerase I, Bst) for each dNTPs (e.g., dATP, dTTP, dCTP, dGTP) in the presence of $Sr^{2+}$ can be different. Therefore, examination can involve measuring the binding affinities of polymerase-template nucleic acids to dNTPs; wherein binding affinity is indicative of the next base in the template nucleic acid. Optionally, the binding interaction may be performed under conditions that destabilize the binary interactions between the polymerase and primed template nucleic acid. Optionally, the binding interaction may be performed under conditions that stabilizes the ternary interactions between the polymerase, the primed template nucleic acid, and the next correct nucleotide. After examination, a wash step removes unbound nucleotides, and $Mg^{2+}$ is added to the reaction to induce nucleotide incorporation and pyrophosphate (PPi) release. Optionally, the wash step comprises $Sr^{2+}$ to maintain the stability of the ternary complex, preventing the dissociation of the ternary complex. The reaction may be repeated until a desired sequence read-length is obtained.

Optionally, a closed-complex is formed between a polymerase, primed template nucleic acid, and nucleotide in reaction conditions comprising $Ni^{2+}$ wherein $Ni^{2+}$ induces the formation of the closed-complex. The presence of $Ni^{2+}$ can allow for the favorable formation of a closed-complex comprising a next correct nucleotide over the formation a complex comprising an incorrect nucleotide. $Ni^{2+}$ may be present at concentrations from about 0.01 mM to about 30 mM. Optionally, $Ni^{2+}$ is present as 10 mM $NiCl_2$. The formation of the closed-complex is monitored under examination conditions to identify the next base in the template nucleic acid of the closed-complex. The affinity of the polymerase (e.g., Klenow fragment of *E. coli* DNA polymerase I, Bst) for each dNTPs (e.g., dATP, dTTP, dCTP, dGTP) in the presence of $Sr^{2+}$ can be different. Therefore, examination can involve measuring the binding affinities of polymerase-template nucleic acids to dNTPs; wherein binding affinity is indicative of the next base in the template nucleic acid. Optionally, the binding interaction may be performed under conditions that destabilize the binary interactions between the polymerase and primed template nucleic acid. Optionally, the binding interaction may be performed under conditions that stabilizes the ternary interactions between the polymerase, the primed template nucleic acid, and the next correct nucleotide. After examination, a wash removes unbound nucleotides and polymerase, and $Mg^{2+}$ is added to the reaction to induce nucleotide incorporation and pyrophosphate release. Optionally, the wash buffer comprises $Ni^{2+}$ to maintain the stability of the ternary complex, preventing the dissociation of the ternary complex. The reaction may be repeated until a desired sequence read-length is obtained.

Optionally, a closed-complex is formed between a polymerase, primed template nucleic acid, and nucleotide in reaction conditions comprising non-catalytic concentrations of $Co^{2+}$ wherein $Co^{2+}$ induces the formation of the closed-complex. The presence of non-catalytic concentrations of $Co^{2+}$ can allow for the favorable formation of a closed-complex comprising a next correct nucleotide over the formation a complex comprising an incorrect nucleotide. $Co^{2+}$ may be present at concentrations from about 0.01 mM to about 0.5 mM. Optionally, $Co^{2+}$ is present as 0.5 mM $CoCl_2$. The formation of the closed-complex is monitored under examination conditions to identify the next base in the template nucleic acid of the closed-complex. The affinity of the polymerase (e.g., Klenow fragment of *E. coli* DNA polymerase I, Bst) for each dNTPs (e.g., dATP, dTTP, dCTP, dGTP) in the presence of $Co^{2+}$ can be different. Therefore, examination can involve measuring the binding affinities of polymerase-template nucleic acids to dNTPs; wherein binding affinity is indicative of the next base in the template nucleic acid. Optionally, the binding interaction may be performed under conditions that destabilize the binary interactions between the polymerase and primed template nucleic acid. Optionally, the binding interaction may be performed under conditions that stabilizes the ternary interactions between the polymerase, the primed template nucleic acid, and the next correct nucleotide. After examination, a wash removes unbound nucleotides and polymerase, and $Co^{2+}$ at a catalytic concentration is added to the reaction to induce nucleotide incorporation and pyrophosphate release. Optionally, the wash buffer comprises non-catalytic amounts of $Co^{2+}$ to maintain the stability of the ternary complex, preventing the dissociation of the ternary complex. The reaction may be repeated until a desired sequence read-length is obtained.

Optionally, a catalytic metal ion may facilitate the formation of a closed-complex without subsequent nucleotide incorporation and closed-complex release. Optionally, a concentration of 0.5, 1, 2, 3, 4, 5, 6, 7, 8, 9, or 10 µM $Mg^{2+}$ in a reaction mixture can induce conformational change of a polymerase to form a closed-complex without subsequent nucleotide incorporation, PPi and closed-complex release. Optionally, the concentration of $Mg^{2+}$ is from about 0.5 µM to about 10 µM, from about 0.5 µM to about 5 µM, from about 0.5 µM to about 4 µM, from about 0.5 µM to about 3 µM, from about µM to about 5 µM, from about 1 µM to about 4 µM, and from about 1 µM to about 3 µM.

Optionally, the concentration of catalytic metal ion in the sequencing reaction which is necessary to allow nucleotide incorporation is from about 0.001 mM to about 10 mM, from about 0.01 mM to about 5 mM, from about 0.01 mM to about 3 mM, from about 0.01 to about 2 mM, from about 0.01 mM to about 1 mM, from about 0.05 to about 10 mM, from about 0.05 mM to about 5 mM, from about 0.05 mM to about 3 mM, from about 0.05 to about 2 mM, or from about 0.05 mM to about 1 mM. Optionally, the concentration of catalytic metal ion is from 5 to 50 mM. Optionally, the concentration of catalytic metal ion is from 5 to 15 mM or about 10 mM.

A non-catalytic ion may be added to the reaction mixture at any stage including before, during, or after any of the following reaction steps: providing a primed template nucleic acid, providing a polymerase, formation of a binary complex, providing a nucleotide, formation of a pre-chemistry closed-complex, nucleotide incorporation, formation of a pre-translocation closed-complex, and formation of a post-translocation conformation. The non-catalytic ion may be added to the reaction mixture during wash steps. The non-catalytic ion may be present through the reaction in the reaction mixture. For example, a catalytic ion is added to the reaction mixture at concentrations which dilute the non-catalytic metal ion, allowing for nucleotide incorporation.

The ability of catalytic and non-catalytic ions to modulate nucleotide incorporation may depend on conditions in the reaction mixture including, but not limited to, pH, ionic strength, chelating agents, chemical cross-linking, modified polymerases, non-incorporable nucleotides, mechanical or vibration energy, and electric fields.

Optionally, the concentration of non-catalytic metal ion in the sequencing reaction necessary to allow for closed-complex formation without nucleotide incorporation is from about 0.1 mM to about 50 mM, from about 0.1 mM to about 40 mM, from about 0.1 mM to about 30 mM, from about 0.1 mM to about 20 mM, from about 0.1 mM to about 10 mM, from about 0.1 mM to about 5 mM, from about 0.1 to about 1 mM, from about 1 mM to about 50 mM, from about 1 to about 40 mM, from about 1 mM to about 30 mM, from about 1 mM to about 20 mM, from about 1 mM to about 10 mM, from about 1 mM to about 5 mM, from about 2 mM to about 30 mM, from about 2 mM to about 20 mM, from about 2 mM to about 10 mM, or any concentration within these ranges.

A closed complex may be formed and/or stabilized by the addition of a polymerase inhibitor to the examination reaction mixture. Inhibitor molecules phosphonoacetate, (phosphonoacetic acid) and phosphonoformate (phosphonoformic acid, common name Foscarnet), Suramin, Aminoglycosides, INDOPY-1 and Tagetitoxin are non-limiting examples of uncompetitive or noncompetitive inhibitors of polymerase activity. The binding of the inhibitor molecule, near the active site of the enzyme, traps the polymerase in either a pre-translocation or post-translocation step of the nucleotide incorporation cycle, stabilizing the polymerase in its closed-complex conformation before or after the incorporation of a nucleotide, and forcing the polymerase to be bound to the template nucleic acid until the inhibitor molecules are not available in the reaction mixture by removal, dilution or chelation.

Thus, provided is a method for sequencing a template nucleic acid molecule including an examination step including providing a template nucleic acid molecule primed with a primer; contacting the primed template nucleic acid molecule with a first reaction mixture comprising a polymerase, a polymerase inhibitor and at least one unlabeled nucleotide molecule; monitoring the interaction of the polymerase with the primed template nucleic acid molecule in the presence of the unlabeled nucleotide molecule without incorporation of the nucleotide into the primer of the primed template nucleic acid molecule; and identifying the nucleotide that is complementary to the next base of the primed template nucleic acid molecule by the monitored interaction. The polymerase inhibitor prevents the incorporation of the unlabeled nucleotide molecule into the primer of the primer template nucleic acid. Optionally, the inhibitor is a non-competitive inhibitor, an allosteric inhibitor, or an uncompetitive allosteric inhibitor. Optionally, the polymerase inhibitor competes with a catalytic ion binding site in the polymerase.

Aminoglycosides non-competitively inhibit polymerase activity by displacing magnesium binding sites in a Klenow polymerase. The non-competitive nature of the interaction with respect to nucleotide binding allows the polymerase to interact with the template nucleic acid and nucleotide, affecting only the catalytic step of nucleotide incorporation.

One inhibitor molecule is the drug Efavirenz, which acts as a non-competitive inhibitor to the HIV-1 reverse transcriptase. The drug has high affinity and a low off-rate for the closed-complex configuration of the polymerase, such that, once the polymerase incorporates the next correct nucleotide, the drug binds to the polymerase, preventing the polymerase from opening its fingers to allow for binding and/or incorporation of a subsequent nucleotide. If the reaction occurs under conditions that favor ternary closed-complex formation over the formation of a binary complex, non-specific polymerase-template nucleic acid interactions can be eliminated, wherein, the binding of the polymerase signifies the added nucleotide is complementary to the next base on the template. If the reaction occurs under examination reaction conditions, the high-affinity binding of the polymerase to the template nucleic acid containing the next correct nucleotide can be used to distinguish the ternary closed-complex from random, non-specific interaction of polymerase with the template nucleic acid. Optionally, high-affinity polymerase binding indicates nucleotide incorporation, and a separate incorporation step is not required. Once the polymerase is bound, and the binding detected, the excess nucleotides and polymerases may be removed or sequestered from the reaction mixture. The next nucleotide may be added under examination reaction conditions and the process repeated cyclically for all nucleotide types, or in a random or predetermined order, until sequencing of a desired read-length is complete.

Any polymerase may be chosen and a suitable non-competitive inhibitor may be uncovered using a high-throughput screening (HTS) process. Many examples of HTS processes for polymerase inhibitors are found in the literature, wherein the specific screening criteria is for non-competitive polymerase inhibitors. As a general concept, these inhibitors can be screened to have a binding site that is only exposed when the polymerase is in its closed conformation, and they bind with high affinities and very low off-rates, such that the binding of the inhibitor stabilizes the polymerase in the closed conformation. Such an inhibitor allows incorporation of a single base, after which the binding of the inhibitor prevents the polymerase from opening up to receive another nucleotide. The entire system can be washed away, including the polymerase, before initiating the next step (examination or incorporation) in the sequencing reaction.

Optionally, polymerase inhibitors found to be effective in inhibiting a HIV-1 reverse transcriptase polymerase are employed to stabilize a closed-complex. Optionally, the inhibitor is an inhibitor of HIV-2 reverse transcriptase. HIV-1 reverse transcriptase inhibitors include nucleoside/nucleotide reverse transcriptase inhibitors (NRTI) and non-nucleoside reverse transcriptase inhibitors (NNRTI). NRTis include, but are not limited to, COMBIVIR (lamivudine and zidovudine; GlaxoSmithKline, Middlesex, UK), EMTRIVA (emtricitabine; Gilead Sciences, Foster City, Calif.), EPIVIR (lamivudine; GlaxoSmithKline, Middlesex, UK), EPZICOM (abacavir sulfate and lamivudine; GlaxoSmithKline, Middlesex, UK), HMD (zalcitabine; Hoffmann-La Roche, Nutley, N.J.), RETROVIR (zidovudine; GlaxoSmithKline, Middlesex, UK), TRIZIVIR (abacavir sulfate, zidovudine, lamivudine; GlaxoSmithKline, Middlesex, UK), TRUVADA (emtricitabine/tenofovir disoproxil fumarate; Gilead Sciences, Foster City, Calif.), VIDEX EC (enteric coated didanosine; Bristol Myers-Squibb, New York, N.Y.), VIDEX (didanosine; Bristol Myers-Squibb, New York, N.Y.), VIREAD (tenofovir disoproxil fumarate; Gilead Sciences, Foster City, Calif.), ZERIT (stavudine; Bristol Myers-Squibb, New York, N.Y.), and ZIAGEN (abacavir sulfate; GlaxoSmithKline, Middlesex, UK). Examples of NNRTI include, but are not limited to, VIRAMUNE (nevirapine; Boehringer Ingelheim, Rhein, Germany), SUSTIVA (efavirenz, Bristol Myers-Squibb, New York, N.Y.), DELAVIRDINE (Rescriptor; Pfizer, New York, N.Y.), and INTELENCE (etravirine; Tibotec Therapeutics, Eastgate Village, Ireland). Optionally, NNRTis are non-competitive polymerase inhibitors that bind to an allosteric center located near the RNA polymerase active site on subunit p66.

Optionally, an HIV-1 reverse transcriptase polymerase inhibitor is a (4/6-halogen/MeO/EtO-substituted benzo[d]thiazol-2-yl)thiazolidin-4-one. Table 1 includes a list of 19 (4/6-halogen/MeO/EtO-substituted benzo[d]thiazol-2-yl)thiazolidin-4-ones inhibitors (adapted from E. Pitta et. al., Synthesis and HIV-1 RT inhibitory action of novel (4/6-substituted benzo[d]thiazol-2-yl)thiazolidin-4-ones. Divergence from the non-competitive inhibition mechanism, Journal of Enzyme Inhibition and Medicinal Chemistry, February 2013, Vol. 28, No. 1, Pages 113-122). The (4/6-halogen/MeO/EtO-substituted benzo[d]thiazol-2-yl)thiazolidin-4-ones inhibitors have the following formula:

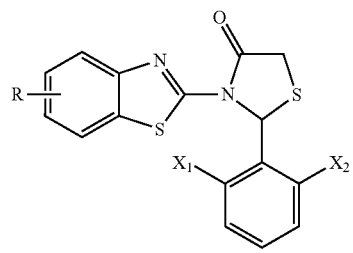

TABLE 1

(4/6-halogen/MeO/EtO-substituted benzo[d]thiazol-2-yl)thiazolidin-4-ones inhibitors

| NNRTI Inhibitor | R | $X_1$ | $X_2$ |
| --- | --- | --- | --- |
| 1 | 4-H, 6-H | F | F |
| 2 | 4-H, 6-H | F | Cl |
| 3 | 4-H, 6-Cl | Cl | Cl |
| 4 | 4-H, 6-Cl | F | Cl |
| 5 | 4-H, 6-Cl | F | F |
| 6 | 4-H, 6-H | Cl | Cl |
| 7 | 4-H, 6-H | F | Cl |
| 8 | 4-H, 6-H | F | F |
| 9 | 4-H, 6-F | Cl | Cl |
| 10 | 4-H, 6-F | F | Cl |
| 11 | 4-H, 6-F | F | F |
| 12 | 4-H, 6-MeO | Cl | Cl |
| 13 | 4-H, 6-MeO | F | Cl |
| 14 | 4-H, 6-MeO | F | F |
| 15 | 4-MeO, 6-H | Cl | Cl |
| 16 | 4-MeO, 6-H | F | Cl |
| 17 | 4-H, 6-EtO | Cl | Cl |
| 18 | 4-H, 6-EtO | F | Cl |
| 19 | 4-H, 6-EtO | F | F |

Any suitable combination of polymerase inhibitors and polymerase mutants may be used so long as they trap/stabilize the closed-complex and, optionally, prevent multiple nucleotide incorporations per cycle.

The provided reaction mixtures can comprise from 100 nM to 1 mM of the polymerase inhibitor or any amount of inhibitor between 100 nM to 1 mM. Optionally, the provided reaction mixtures can comprise from 1 to 200 µM of the polymerase inhibitor or any amount. Optionally, the reaction mixtures include from 30 to 150 µM of the polymerase inhibitor. Optionally, the reaction mixtures include from 30 to 70 µM of the polymerase inhibitor. Optionally, the reaction mixtures include from 60 to 140 µM of the polymerase inhibitor.

Optionally, the polymerase of the closed-complex is prevented from opening its finger domains and translocating to the next template nucleic acid position by using pyrophosphate analogs or other related molecules. Pyrophosphate analogs configure the polymerase in closed-complex by occupying sites close to the triphosphate binding site in the active pocket of the polymerase. Release of the pyrophosphate (PPi) is critical for the polymerase to assume the open conformation, translocate to the next template nucleic acid position, and accept the next nucleotide. The non-competitive inhibitor, such as Foscarnet (phosphonoformate), phosphonoacetate or other pyrophosphate analogs, traps the polymerase in its fingers-closed confirmation. Optionally, binding of the PPi analog is reversible, with the polymerase activity fully restored by washing away, diluting, or sequestering the inhibitor in the reaction mixture. Broadly, any non-competitive inhibitor of polymerase activity may be used during the sequencing reaction.

Optionally, a polymerase inhibitor which stabilizes a closed-complex is combined with reaction conditions which usually release the closed-complex, including, but not limited to, the presence of a catalytic metal ion, such as magnesium or manganese. Optionally, the closed-complex is stabilized even in the presence of a catalytic metal ion. Optionally, the closed-complex is released even in the presence of a polymerase inhibitor. Optionally, the stabilization of the closed-complex is dependent, in part, on the concentrations, the identity of the stabilization reagent, the identity of release reagents, and any combination thereof. Optionally, the stabilization of a closed-complex using polymerase inhibitors is combined with additional reaction conditions which also function to stabilize a closed-complex, including, but not limited to, sequestering, removing, reducing, omitting, and/or chelating a catalytic metal ion; the presence of a modified polymerase in the closed-complex; a non-incorporable nucleotide in the closed-complex; and any combination thereof.

Polymerases may be modified to facilitate closed-complex formation and/or stabilization during the examination step of the sequencing methods described herein. Thus, a modified polymerase may be used in the provided methods. Modifications of polymerases may include cross-linking the members within the closed-complex with cross-linkers or forming disulfide bonds within the polymerase to maintain a closed-complex.

Optionally, cysteines are positioned so that when a closed-complex is formed, the cysteines are in close proximity to form at least one disulfide bond to trap the polymerase in the closed conformation. Optionally, the finger and the thumb domain of the polymerase are engineered to contain one or more cysteines each, such that in the closed-complex, the cysteines on the opposing fingers interact, forming a disulfide bond and trapping the polymerase in its closed conformation. Introducing cysteines to suitable positions on the polymerase so as to induce disulfide bond formation can be accomplished using methods known to those in the art of protein engineering. A reducing agent such as 2-mercaptoethanol (BME), cysteine-HCl, dithiothreitol (DTT), Tris (2-carboxyethyl) phosphine (TCEP), or any combination thereof may be used to reduce the disulfide bond and release the polymerase. Optionally, nucleotides are added sequentially, one at a time, in separate examination steps along with the cysteine modified polymerase, wherein the need for additional examination reaction conditions that favor closed-complex formation and/or stabilization is optional. Optionally, 1, 2, 3, 4 or more nucleotides are added in combination (e.g., dATP, dTTP, dCTP, and dGTP), in one examination step along with the cysteine modified polymerase, wherein the need for additional examination reaction conditions that favor closed-complex formation and/or stabilization is optional.

Optionally, a cysteine-modified polymerase binds to a template nucleic acid without incorporating a correct nucleotide while forming a closed-complex. While in the closed-complex, the cysteines of the polymerase are close enough in space to form at least one disulfide bond, thereby stabilizing the closed-complex. In this example, the polymerase is trapped and prevented from nucleotide incorporation.

Optionally, a nucleotide present in the examination reaction mixture is a next correct nucleotide, and the cysteine-modified polymerase binds to a template nucleic acid and incorporates the next correct nucleotide forming a closed-complex; wherein while in the closed-complex, the cysteines of the polymerase are close enough in space to form at least one disulfide bond, thereby stabilizing the closed-complex. After closed-complex stabilization and monitoring, an incorporation step can be performed wherein a reducing agent breaks the disulfide bond, releasing the polymerase from the closed complex. The reducing agent may then be removed, diluted, or sequestered and another examination step may be performed.

Optionally, the nucleotide of the disulfide-stabilized closed-complex is incorporated prior to or during stabilization of the closed-complex. An incorporation step may be performed by reducing the disulfide bond to allow for subsequent nucleotide incorporation and/or an additional examination step.

Optionally, one nucleotide is added to the reaction mixture during the examination step. Optionally, 1, 2, 3, 4 or more nucleotides are added to the reaction mixture during the examination step. Optionally, the next correct nucleotide is enclosed within the closed-complex. Optionally, an incorrect nucleotide is enclosed within the closed-complex.

Optionally, a polymerase may form a disulfide bond with itself after formation of a closed-complex. A polymerase can form a disulfide bond to the primed template nucleic acid after formation of a closed-complex. The closed-complex may include a next correct nucleotide based-paired to the next base and/or incorporated to the primer of the primed template nucleic acid. Optionally, the closed-complex comprises an incorrect nucleotide, wherein binding to the next base and/or incorporation is attenuated.

Optionally, the polymerase is stabilized via cross-linking methods involving the polymerase of the closed-complex. The cross-linking methods do not need to be reversible, as the polymerase can be unbound from the nucleic acid using other means, such as enzymatic or chemical cleavage, denaturation or any combination thereof. Denaturants include, but are not limited to, acids such as acetic acid, or trichloroacetic acid; solvents such as ethanol or methanol; chaotropic agents such as urea, guanidinium chloride, lithium perchlorate; surfactants such as sodium dodecyl sulfate; or any combination thereof. Chemical cleavage includes the use of one or more of natural, modified, or commercially available proteases. Additional methods for releasing a cross-linked polymerase include, but are not limited to, altering pH, temperature, ionic strength, or any combination thereof.

The closed-complex is formed without incorporation of the enclosed nucleotide during an examination step of a reaction. Optionally, the examination reaction mixture at any point in time includes a cross-linking agent, wherein the closed-complex is cross-linked. In this example, the polymerase is trapped and prevented from nucleotide incorporation. Optionally, a nucleotide present in the examination reaction mixture is a next correct nucleotide, and a polymerase binds to a template nucleic acid and incorporates the next correct nucleotide forming a closed-complex; wherein, while in the closed-complex, a cross-linking agent is available to trap the closed-complex. After closed-complex stabilization and monitoring, an incorporation step can be performed wherein the closed-complex is released from its closed-conformation. Optionally, a closed-complex is formed and the next correct nucleotide is incorporated into the template nucleic acid primer. The cross-linking inhibits the polymerase from translocating to the next base position and the next nucleotide cannot be added until the polymerase is no longer cross-linked. Optionally, the nucleotide of the cross-linked-stabilized closed-complex is incorporated prior to or during stabilization of the closed-complex. An incorporation step may be performed by cleaving the linkage and/or denaturing the polymerase to allow for subsequent nucleotide incorporation and/or an additional examination step.

Optionally, a polymerase may be cross-linked to itself after formation of a closed-complex. Thus, a polymerase can be cross-linked to the primed template nucleic acid after formation of a closed-complex. The closed-complex may include a next correct nucleotide which is based-paired to the next base and/or incorporated to the primer of the primed template nucleic acid. Optionally, the closed-complex comprises an incorrect nucleotide who's binding to the next base and/or incorporation is attenuated.

Optionally, a polymerase is modified to favor the formation of a closed-complex over the formation of a binary complex. The polymerase modifications may be genetically engineered. Polymerases may be selected based on their selective binding affinities to the template nucleic acid. A polymerase may be selected or modified to have a high affinity for nucleotides, wherein the polymerase binds to a nucleotide prior to binding to the template nucleic acid. For example, the DNA polymerase X from the African Swine Fever virus has an altered order of substrate binding, where the polymerase first binds to a nucleotide, then binds to the template nucleic acid. Polymerases that bind to nucleotides first may be utilized to develop novel sequencing schemes. Polymerase modifications can be designed to trap the polymerase in a closed-complex in the methods disclosed herein. The polymerase may be trapped permanently or transiently.

Optionally, a modified polymerase that allows for the stabilization of a closed-complex is combined with reaction conditions, usually to release the closed-complex, including, but not limited to, the presence of a release reagent (e.g., catalytic metal ion, such as magnesium or manganese). Optionally, the closed-complex is stabilized even in the presence of a catalytic metal ion. Optionally, the closed-complex is released even in the presence of a cross-linking agent. Optionally, the stabilization of the closed-complex is dependent, in part, on the concentrations and/or identity of the stabilization reagent and/or the release reagents, and any combination thereof. Optionally, the stabilization of a closed-complex using one or more modified polymerases is combined with additional reaction conditions to stabilize a closed-complex, including, but not limited to, sequestering, removing, reducing, omitting, and/or chelating a catalytic metal ion; the presence of a polymerase inhibitor, or non-incorporable nucleotide; and any combination thereof.

Optionally, a closed-complex of an examination step comprises a nucleotide analog or modified nucleotide to facilitate stabilization of the closed-complex. Optionally, a nucleotide analog comprises a nitrogenous base, five-carbon sugar, and phosphate group; wherein any component of the nucleotide may be modified and/or replaced. Nucleotide analogs may be non-incorporable nucleotides. Non-incorporable nucleotides may be modified to become incorporable at any point during the sequencing method.

Nucleotide analogs include, but are not limited to, alpha-phosphate modified nucleotides, alpha-beta nucleotide analogs, beta-phosphate modified nucleotides, beta-gamma nucleotide analogs, gamma-phosphate modified nucleotides, caged nucleotides, or ddNTPs. Examples of nucleotide analogs are described in U.S. Pat. No. 8,071,755, which is incorporated by reference herein in its entirety.

Nucleotide analogs can include terminators that reversibly prevent nucleotide incorporation to the 3' end of the primer. One type of reversible terminator is a 3'-O-blocked reversible terminator. The terminator is linked to the oxygen atom of the 3' OH end of the 5-carbon sugar of a nucleotide. Another type of reversible terminator is a 3'-unblocked reversible terminator. The terminator is linked to the nitrogenous base of a nucleotide. For reviews of nucleotide analogs having terminators see e.g., Mu, R., et al., "The History and Advances of Reversible Terminators Used in New Generations of Sequencing Technology," Genomics, Proteomics & Bioinformatics 11(1):34-40 (2013).

Optionally, nucleotides are substituted for modified nucleotide analogs having terminators that irreversibly prevent nucleotide incorporation to the 3' end of the primer. Irreversible nucleotide analogs include 2', 3' dideoxynucleotides, ddNTPs (ddGTP, ddATP, ddTTP, ddCTP). Dideoxynucleotides lack the 3'-OH group of dNTPs that is essential for polymerase-mediated synthesis.

Optionally, non-incorporable nucleotides comprise a blocking moiety that inhibits or prevents the nucleotide from forming a covalent linkage to a second nucleotide (3' OH of a primer) during the incorporation step of a nucleic acid polymerization reaction. The blocking moiety can be removed from the nucleotide, allowing for nucleotide incorporation.

Optionally, a nucleotide analog present in a closed-complex renders the closed-complex stable. Optionally, the nucleotide analog is non-incorporable. Optionally, the nucleotide analog is released and a native nucleotide is incorporated. Optionally, the closed-complex is released, the nucleotide analog is modified, and the modified nucleotide analog is incorporated. Optionally, the closed-complex is released under reaction conditions that modify and/or destabilize the nucleotide analog in the closed-complex.

Optionally, a nucleotide analog present in a closed-complex is incorporated and the closed-complex is stabilized. The closed complex may be stabilized by the nucleotide analog, or for example, by any stabilizing methods disclosed herein. Optionally, the nucleotide analog does not allow for the incorporation of a subsequent nucleotide. The closed-complex can be released, for example, by any methods described herein, and the nucleotide analog is modified. The modified nucleotide analog may allow for subsequent incorporation of a nucleotide to its 3' end.

Optionally, a nucleotide analog is present in the reaction mixture during the examination step. For example, 1, 2, 3, 4 or more nucleotide analogs are present in the reaction mixture during the examination step. Optionally, a nucleotide analog is replaced, diluted, or sequestered during an incorporation step. Optionally, a nucleotide analog is replaced with a native nucleotide. The native nucleotide may include a next correct nucleotide. Optionally, a nucleotide analog is modified during an incorporation step. The modified nucleotide analog can be similar to or the same as a native nucleotide.

Optionally, a nucleotide analog has a different binding affinity for a polymerase than a native nucleotide. Optionally, a nucleotide analog has a different interaction with a next base than a native nucleotide. Nucleotide analogs and/or non-incorporable nucleotides may base-pair with a complementary base of a template nucleic acid.

Optionally, a nucleotide analog is a nucleotide, modified or native, fused to a polymerase. Optionally, a plurality of nucleotide analogs comprises fusions to a plurality of polymerases, wherein each nucleotide analog comprises a different polymerase.

A nucleotide can be modified to favor the formation of a closed-complex over the formation of a binary complex. The nucleotide modifications may be genetically engineered. A nucleotide may be selected or modified to have a high affinity for a polymerase, wherein the polymerase binds to a nucleotide prior to binding to the template nucleic acid.

Any nucleotide modification that trap the polymerase in a closed-complex may be used in the methods disclosed herein. The nucleotide may be trapped permanently or transiently. Optionally, the nucleotide analog is not the means by which a closed-complex is stabilized. Any closed-complex stabilization method may be combined in a reaction utilizing a nucleotide analog.

Optionally, a nucleotide analog that allows for the stabilization of a closed-complex is combined with reaction conditions that usually release the closed-complex. The conditions include, but are not limited to, the presence of a release reagent (e.g., catalytic metal ion, such as magnesium or manganese). Optionally, the closed-complex is stabilized even in the presence of a catalytic metal ion. Optionally, the closed-complex is released even in the presence of a nucleotide analog. Optionally, the stabilization of the closed-complex is dependent, in part, on the concentrations and/or identity of the stabilization reagent and/or release reagents, and any combination thereof. Optionally, the stabilization of a closed-complex using nucleotide analogs is combined with additional reaction conditions that function to stabilize a closed-complex, including, but not limited to, sequestering, removing, reducing, omitting, and/or chelating a catalytic metal ion; the presence of a polymerase inhibitor, cross-linking agent; and any combination thereof.

In an exemplary sequencing reaction, the examination step comprises formation and/or stabilization of a closed-complex comprising a polymerase, primed template nucleic acid, and nucleotide. Characteristics of the formation and/or release of the closed-complex are monitored to identify the enclosed nucleotide and therefore the next base in the template nucleic acid. Closed-complex characteristics can be dependent on the sequencing reaction components (e.g., polymerase, primer, template nucleic acid, nucleotide) and/or reaction mixture components and/or conditions. Optionally, the closed-complex is in a pre-chemistry conformation. Optionally, the closed-complex is in a pre-translocation conformation. Optionally, the closed-complex is in a post-translocation conformation.

The examination step involves monitoring the interaction of a polymerase with a template nucleic acid in the presence of a nucleotide. The formation of a closed-complex may be monitored. Optionally, the absence of formation of closed-complex is monitored. Optionally, the dissociation of a closed-complex is monitored. Optionally, the incorporation step involves monitoring incorporation of a nucleotide. Optionally, the incorporation step involves monitoring the absence of nucleotide incorporation.

Any process of the examination and/or incorporation step may be monitored. Optionally, a polymerase has a detectable tag. Optionally, no component of the sequencing reaction is detectably labeled. Optionally, the detectable tag or label on the polymerase is removable. Optionally, the nucleotides or polymerases have a detectable label, however, the label is not detected during sequencing.

Monitoring the variation in affinity of a polymerase to a template nucleic acid in the presence of correct and incorrect nucleotides, under conditions that may or may not allow the incorporation of the nucleotide, may be used to determine the sequence of the template nucleic acid. The affinity of a polymerase to a template nucleic acid in the presence of different nucleotides, including modified or labeled nucleotides, can be monitored as the off-rate of the polymerase-nucleic acid interaction in the presence of the various nucleotides. The affinities and off-rates of many standard polymerases to various matched/correct, mismatched/incorrect and modified nucleotides are known in the art. Single molecule imaging of Klenow polymerase reveals that the off-rate for a template nucleic acid for different nucleotide types, where the nucleotide types are prevented from incorporating, are distinctly and measurably different.

Optionally, a nucleotide of a particular type is made available to a polymerase in the presence of a primed template nucleic acid. The reaction is monitored, wherein, if the nucleotide is a next correct nucleotide, the polymerase may be stabilized to form a closed-complex. If the nucleotide is an incorrect nucleotide, a closed-complex may still be formed; however, without the additional assistance of stabilizing agents or reaction conditions (e.g., absence of catalytic ions, polymerase inhibitors, salt), the closed-complex may dissociate. The rate of dissociation is dependent on the affinity of the particular combination of polymerase, template nucleic acid, and nucleotide, as well as reaction conditions. Optionally, the affinity is measured as an off-rate. Optionally, the affinity is different between different nucleotides for the closed-complex. For example, if the next base in the template nucleic acid downstream of the 3' end of the primer is G, the polymerase-nucleic acid affinity, measured as an off-rate, is expected to be different based on whether dATP, dCTP, dGTP or dTTP are added. In this case, dCTP would have the slowest off-rate, with the other nucleotides providing different off-rates for the interaction. Optionally, the off-rate may be different depending on the reaction conditions, for example, the presence of stabilizing agents (e.g., absence of magnesium or inhibitory compounds) or reaction conditions (e.g., nucleotide modifications or modified polymerases). Once the identity of the next correct nucleotide is determined, 1, 2, 3, 4 or more nucleotide types may be introduced simultaneously to the reaction mixture under conditions that specifically target the formation of a closed-complex. Excess nucleotides may be removed from the reaction mixture and the reaction conditions modulated to incorporate the next correct nucleotide of the closed-complex. This sequencing reaction ensures that only one nucleotide is incorporated per sequencing cycle.

Optionally, a plurality of template nucleic acids are tethered to a surface and one (or more) dNTPs are flowed in sequentially. The spectrum of affinities reveals the identity of the next correct nucleotide and therefore the next base in the template nucleic acid. Optionally, the affinities are measured without needing to remove and replace reaction mixture conditions, i.e., a wash step. Autocorrelation of the measured intensities of the binding interaction, for instance, could readily reveal the dynamics of the interaction, thus revealing the affinities without requiring a washing step to measure the off-rate.

Any technique that can measure dynamic interactions between a polymerase and nucleic acid may be used to measure the affinities and enable the sequencing reaction methods disclosed herein.

Optionally, the affinity of a polymerase to a nucleotide is dependent, in part, on the identity of the next base in the primed template nucleic acid and/or the identity of the nucleotide. Optionally, the affinity can be altered by modification of the polymerase, nucleotide, primer, template nucleic acid, or any combination thereof. Optionally, the reaction mixture conditions and/or additional components affect the affinity value.

Provided herein are methods to create a table of polymerase-nucleic acid affinities for a variety of possible combinations of nucleotides and next bases. Because these affinities are affected primarily by interactions at the polymerase active site, where only the nucleotide and next base on the nucleic acid template participate, context specific effects may be neglected. Context specific effects may include secondary structures of the nucleic acid and contribution of bases further down the sequence from the next base on the template nucleic acid. The table of affinities allows for the determination of a nucleotide, natural or modified, which induces the widest and most easily measured dispersion in affinities for different template bases. Optionally, the template bases are 1, 2, 3, or 4 of the bases dATP, dTTP, dCTP, and dGTP. It is understood that the strongest affinity will exist for the base that is complementary to the nucleotide. As used herein, dispersion particularly refers to the variation in affinities for the other three incorrect, non-complementary bases. Optionally, each affinity is measured under examination conditions that inhibit nucleotide incorporation. Optionally, the polymerase is modified or selected to provide a wide dispersion in affinities. The engineered or natural polymerase may have unfavorable error profiles or other unfavorable properties as a sequencing enzyme, which is immaterial as this polymerase will only be used under non-incorporating conditions. A polymerase may be expressly selected for its ability to provide easily measurable and distinct affinities for different template bases. Evolving or screening for polymerases with desired properties are standard procedures in the art (e.g., screening for polymerases with high affinity for modified nucleotides). Optionally, a polymerase is replaced with a high-fidelity polymerase for an incorporation step. Optionally, a combination of polymerase and nucleotide is selected that provides the most convenient affinities for the template bases, thereby allowing for the execution of a sequencing method that measure the affinity of the selected polymerase to the template nucleic acid in the presence of the selected nucleotide. The next base on the nucleic acid is determined from the measured affinity, as the spectrum of affinities for the template bases is provided in the constructed affinity table. The affinity can be an on-rate, off-rate, or combination of on-rate and off-rate of the polymerase nucleic acid interaction.

The affinity of a polymerase for a template nucleic acid in the presence of a nucleotide can be measured in a plurality of methods known to one of skill in the art. Optionally, the affinity is measured as an off-rate, where the off-rate is measured by monitoring the release of the polymerase from the template nucleic acid as the reaction is washed by a wash buffer. Optionally, the affinity is measured as an off-rate, where the off-rate is measured by monitoring the release of the polymerase from the template nucleic acid under equilibrium binding conditions, especially equilibrium binding conditions where the polymerase binding rates are low or diffusion limited. The polymerase binding rates may be diffusion limited at sufficiently low concentrations of polymerase, wherein if the polymerase falls-off from the DNA-polymerase complex, it does not load back immediately, allowing for sufficient time to detect that the polymerase has been released from the complex. For a higher affinity interaction, the polymerase is released from the nucleic acid slowly, whereas a low affinity interaction results in the polymerase being released more rapidly. The spectrum of affinities, in this case, translates to different off-rates, with the off-rates measured under dynamic wash conditions or at equilibrium. The smallest off-rate corresponds to the base complementary to the added nucleotide, while the other off-rates vary, in a known fashion, depending on the combination of polymerase and nucleotide selected.

Optionally, the off-rate is measured as an equilibrium signal intensity after the polymerase and nucleotide are provided in the reaction mixture, wherein the interaction with the lowest off-rate (highest affinity) nucleotide produces the strongest signal, while the interactions with other, varying, off-rate nucleotides produce signals of measurably different intensities. As a non-limiting example, a fluorescently labeled polymerase, measured, preferably, under total internal reflection (TIRF) conditions, produces different measured fluorescence intensities depending on the number of polymerase molecules bound to surface-immobilized nucleic acid molecules in a suitably chosen window of time. The intrinsic fluorescence of the polymerase, for instance, tryptophan fluorescence, may also be utilized. A high off-rate interaction produces low measured intensities, as the number of bound polymerase molecules, in the chosen time window is very small, wherein a high off-rate indicates that most of the polymerase is unbound from the nucleic acid. Any surface localized measurement scheme may be employed including, but not limited to, labeled or fluorescence schemes. Suitable measurement schemes that measure affinities under equilibrium conditions include, but are not limited to, bound mass, refractive index, surface charge, dielectric constant, and schemes known in the art. Optionally, a combination of on-rate and off-rate engineering yields higher fidelity detection in the proposed schemes. As a non-limiting example, a uniformly low on-rate, base dependent, varying off-rate results in an unbound polymerase remaining unbound for prolonged periods, allowing enhanced discrimination of the variation in off-rate and measured intensity. The on-rate may be manipulated by lowering the concentration of the added polymerase, nucleotide, or both polymerase and nucleotide.

Optionally, the interaction between the polymerase and the nucleic acid is monitored via a detectable tag attached to the polymerase. The tag may be monitored by detection methods including, but limited to, optical, electrical, thermal, mass, size, charge, vibration, and pressure. The label may be magnetic, fluorescent or charged. For external and internal label schemes, fluorescence anisotropy may be used to determine the stable binding of a polymerase to a nucleic acid in a closed-complex.

By way of example, a polymerase is tagged with a fluorophore, wherein closed-complex formation is monitored as a stable fluorescent signal. The unstable interaction of the polymerase with the template nucleic acid in the presence of an incorrect nucleotide results in a measurably weaker signal compared to the closed-complex formed in the presence of the next correct nucleotide.

Optionally, a polymerase is tagged with a chemiluminescent tag, wherein closed-complex formation is monitored as a stable luminescence signal in the presence of the appropriate luminescence triggers. The unstable interaction of the polymerase with the template nucleic acid in the presence of an incorrect nucleotide results in a measurably weaker signal compared to the closed-complex formed in the presence of the next correct nucleotide. Additionally, a wash step prior to triggering luminescence could remove all polymerase molecules not bound in a stable closed complex.

Optionally, a polymerase is tagged with an optical scattering tag, wherein closed-complex formation is monitored as a stable optical scattering signal. The unstable interaction of the polymerase with the nucleic acid in the presence of an incorrect nucleotide results in a measurably weaker signal compared to the closed-complex formed in the presence of the next correct nucleotide.

Optionally, the polymerase is tagged with a plasmonic nanoparticle tag, wherein the closed-complex formation is monitored as a shift in plasmonic resonance that is different from the plasmonic resonance in the absence of the closed-complex or the presence of a closed-complex comprising an incorrect nucleotide. The change in plasmon resonance may be due to the change in local dielectric environment in the closed-complex, or it may be due to the synchronous aggregation of the plasmonic nanoparticles on a cluster of clonally amplified nucleic acid molecules or another means that affects the plasmons differently in the closed-complex configuration.

Optionally, the polymerase is tagged with a Raman scattering tag, wherein, the closed-complex formation is monitored as a stable Raman scattering signal. The unstable interaction of polymerase with the nucleic acid in the presence of an incorrect nucleotide results in a measurably weaker signal compared to the closed-complex formed in the presence of the next correct nucleotide.

Optionally, a next correct nucleotide is identified by a tag on a polymerase selected or modified to have a high affinity for nucleotides, wherein the polymerase binds to a nucleotide prior to binding to the template nucleic acid. For example, the DNA polymerase X from the African Swine Fever virus has an altered order of substrate binding, where the polymerase first binds to a nucleotide, then binds to the template nucleic acid. Optionally, a polymerase is incubated with each type of nucleotide in separate compartments, where each compartment contains a different type of nucleotide and where the polymerase is labeled differently with a tag depending on the nucleotide with which it is incubated. In these conditions, unlabeled nucleotides are bound to differently labeled polymerases. The polymerases may be the same kind of polymerase bound to each nucleotide type or different polymerases bound to each nucleotide type. The differentially tagged polymerase-nucleotide complexes may be added simultaneously to any step of the sequencing reaction. Each polymerase-nucleotide complex binds to a template nucleic acid whose next base is complementary to the nucleotide in the polymerase-nucleotide complex. The next correct nucleotide is identified by the tag on the polymerase carrying the nucleotide. The interrogation of the next template base by the labeled polymerase-nucleotide complex may be performed under non-incorporating and/or examination conditions, where once the identity of the next template base is determined, the complex is destabilized and removed, sequestered, and/or diluted and a separate incorporation step is performed in a manner ensuring that only one nucleotide is incorporated.

A common method to introduce a detectable tag on a polymerase involves chemical conjugation to amines or cysteines present in the non-active regions of the polymerase. Such conjugation methods are well known in the art. As non-limiting examples, n-hydroxysuccinimide esters (NHS esters) are commonly employed to label amine groups that may be found on an enzyme. Cysteines readily react with thiols or maleimide groups, while carboxyl groups may be reacted with amines by activating them with EDC (1-Ethyl-3-[3-dimethylaminopropyl]carbodiimide hydrochloride). Optionally, N-Hydroxysuccinimide (NHS) chemistry is employed at pH ranges where only the N-terminal amines are reactive (for instance, pH 7), such that only a single tag is added per polymerase.

Optionally, the tag attached to the polymerase is a charge tag, such that the formation of stable closed-complex can be detected by electrical means by measuring changes in local charge density around the template nucleic acids. Methods for detecting electrical charges are well known in the art, comprising methods such as field-effect transistors, dielectric spectroscopy, impedance measurements, and pH measurements, among others. Field-effect transistors include, but are not limited to, ion-sensitive field-effect transistors (ISFET), charge-modulated field-effect transistors, insulated-gate field-effect transistors, metal oxide semiconductor field-effect transistors and field-effect transistors fabricated using semiconducting single wall carbon nanotubes.

Optionally, a charge tag is a peptide tag having an isoelectric point below about 4 or above about 10. Optionally, a polymerase comprising a peptide tag has a total isoelectric point below about 5 or above about 9. A charge tag may be any moiety which is positively or negatively charged. The charge tag may comprise additional moieties including mass and/or labels such as dyes. Optionally, the charge tag possesses a positive or negative charge only under certain reaction conditions such as changes in pH.

Optionally, a field-effect transistor (FET) is configured as a biosensor for the detection of a closed-complex. A gate terminal of the FET is modified by the addition of template nucleic acids. The binding of a polymerase comprising a charged tag results in changes in electrochemical signals. Binding of a polymerase with a next correct nucleotide to the template nucleic acid provides different signals than polymerase binding to a template nucleic acid in the presence of other incorrect nucleotides, where each incorrect nucleotide may also provide a different signal. Optionally, polymerase interactions with a template nucleic acid are monitored using FET without the use of a labeled tag on the polymerase, primed template nucleic acid, or nucleotide. Optionally, the pH change that occurs due to release of $H^+$ ions during the incorporation reaction is detected using a FET. Optionally, the polymerase comprises a tag that generates continuous $H^+$ ions that is detected by the FET. Optionally, the continuous $H^+$ ion generating tag is an ATP synthase. Optionally, the continuous $H^+$ ion generation tag is palladium, copper or another catalyst. Optionally, the release of a PPi after nucleotide incorporation is detected using FET. For example, one type of nucleotide may be provided to a reaction at a time. Once the next correct nucleotide is added and conditions allow for incorporation, PPi is cleaved, released, and detected using FET, therefore identifying the next correct nucleotide and the next base. Optionally, template nucleic acids are bound to walls of a nanotube. Optionally, a polymerase is bound to a wall of a nanotube. FET is advantageous for use as a sequencing sensor due to its small size and low weight, making it appropriate for use as a portable sequencing monitoring component. Details of FET detection of molecular interactions are described in Dong-Sun Kim et al., "An FET-Type Charge Sensor for Highly Sensitive Detection of DNA Sequence," Biosensors and Bioelectronics, Microsensors and Microsystems 2003, 20, no. 1 (Jul. 30, 2004): 69-74, doi:10.1016/j.bios.2004.01.025 and Alexander Star et al., "Electronic Detection of Specific Protein Binding Using Nanotube FET Devices," Nano Letters 3, no. 4 (Apr. 1, 2003): 459-63, doi:10.1021/nl0340172, which are incorporated by reference herein in their entireties.

By way of example, the polymerase comprises a fluorescent tag. To monitor polymerase-nucleic acid interaction with high signal-to-noise, evanescent illumination or confocal imaging may be employed. The formation of a closed-complex on localized template nucleic acids may be observed as an increased fluorescence compared to the background, for instance, whereas in some instances it may be also be observed as a decreased fluorescence due to quenching or change in local polar environment. Optionally, a fraction of polymerase molecules may be tagged with a fluorophore while another fraction may be tagged with a quencher in the same reaction mixture; wherein, the formation of closed-complex on a localized, clonal population of nucleic acid is revealed as decrease in fluorescence compared to the background. The clonal population of nucleic acids may be attached to a support surface such as a planar substrate, microparticle, or nanoparticle. Optionally, a polymerase is tagged with a fluorophore, luminophore, chemiluminophore, chromophore, or bioluminophore.

A polymerase may be labeled with a fluorophore and/or quencher. Optionally, a nucleic acid is labeled with a fluorophore and/or quencher. Optionally, one or more nucleotides are labeled with a fluorophore and/or quencher. Exemplary fluorophores include, but are not limited to, fluorescent nanocrystals; quantum dots; d-Rhodamine acceptor dyes including dichloro[R110], dichloro[R6G], dichloro [TAMRA], dichloro[ROX] or the like; fluorescein donor dye including fluorescein, 6-FAM, or the like; Cyanine dyes such as Cy3B; Alexa dyes, SETA dyes, Atto dyes such as atto 647N which forms a FRET pair with Cy3B and the like. Fluorophores include, but are not limited to, MDCC (7-diethylamino-3-[([(2-maleimidyl)ethyl]amino)carbonyl]coumarin), TET, HEX, Cy3, TMR, ROX, Texas Red, Cy5, LC red 705 and LC red 640. Fluorophores and methods for their use including attachment to polymerases and other molecules are described in The Molecular Probes® Handbook (Life Technologies, Carlsbad Calif.) and Fluorophores Guide (Promega, Madison, Wis.), which are incorporated herein by reference in their entireties. Exemplary quenches include, but are not limited to, ZEN, IBFQ, BHQ-1, BHQ-2, DDQ-I, DDQ-11, Dabcyl, Qxl quencher, Iowa Black RQ, and IRDye QC-1.

Optionally, a conformationally sensitive dye may be attached close to the active site of the polymerase without affecting the polymerization ability or fidelity of the polymerase; wherein a change in conformation, or a change in polar environment due to the formation of a closed-complex is reflected as a change in fluorescence or absorbance properties of the dye. Common fluorophores such as cy3 and fluorescein are known to have strong solvatochromatic response to polymerase binding and closed-complex formation, to the extent that the formation of closed-complex can be distinguished clearly from the binary polymerase-nucleic acid complex. Optionally, the closed-complex can be distinguished from binary complexes based on differences in fluorescence or absorbance signals from a conformationally sensitive dye. Optionally, a solvatochromatic dye may be employed to monitor conformational transitions; wherein the change in local polar environment induced by the conformational change can be used as the reporter signal. Solvatochromatic dyes include, but are not limited to, Reichart's dye, IR44, merocyanine dyes (e.g., merocyanine 540), 4-[2-N-substituted-1,4-hydropyridin-4-ylidine)ethylidene] cyclohexa-2,5-dien-1-one, red pyrazolone dyes, azomethine dyes, indoaniline dyes, diazamerocyanine dyes, indigoid dyes, as exemplified by indigo, and others as well as mixtures thereof. Methods to introduce dyes or fluorophores to specific sites of a polymerase are well known in the art. As a non-limiting example, a procedure for site specific labeling of a T7 DNA polymerase with a dye is provided in Yu-Chih Tsai, Zhinan Jin, and Kenneth A. Johnson, "Site-Specific Labeling of T7 DNA Polymerase with a Conformationally Sensitive Fluorophore and Its Use in Detecting Single-Nucleotide Polymorphisms," Analytical Biochemistry 384, no. 1 (Jan. 1, 2009): 136-44, which is incorporated herein in its entirety by reference.

Optionally, a polymerase is tagged with a fluorophore at a position that could sense closed-complex formation without interfering with the reaction. The polymerase may be a native or modified polymerase. Modified polymerases include those with one or more amino acid mutations, additions, and/or deletions. Optionally, one or more, but not all, cysteine amino acids are mutated to another amino acid, such as alanine. In this case, the remaining one or more cysteines are used for site-specific conjugation to a fluorophore. Alternatively, one or more amino acids are mutated to a reactive amino acid suitable for fluorophore conjugation, such as cysteines or amino acids comprising primary amines.

Optionally, binding between a polymerase and a template nucleic acid in the presence of a correct nucleotide may induce a decrease in fluorescence, whereas binding with an incorrect nucleotide causes an increase in fluorescence. Binding between a polymerase and a template nucleic acid in the presence of a correct nucleotide may induce an increase in fluorescence, whereas binding with an incorrect nucleotide causes a decrease in fluorescence. The fluorescent signals may be used to monitor the kinetics of a nucleotide-induced conformational change and identify the next base in the template nucleic acid sequence.

Optionally, the polymerase/nucleic-acid interaction may be monitored by scattering signal originating from the polymerase or tags attached to the polymerase, for instance, nanoparticle tags.

Optionally, one or more nucleotides can be labeled with distinguishing and/or detectable tags or labels, however such tags or labels are not detected during examination, identification of the base or incorporation of the base, and such tags or labels are not detected during the sequencing methods disclosed herein. The tags may be distinguishable by means of their differences in fluorescence, Raman spectrum, charge, mass, refractive index, luminescence, length, or any other measurable property. The tag may be attached to one or more different positions on the nucleotide, so long as the fidelity of binding to the polymerase-nucleic acid complex is sufficiently maintained to enable identification of the complementary base on the template nucleic acid correctly. Optionally, the tag is attached to the nucleobase position of the nucleotide. Under suitable reaction conditions, the tagged nucleotides may be enclosed in a closed-complex with the polymerase and the primed template nucleic acid. Alternatively, a tag is attached to the gamma phosphate position of the nucleotide.

Optionally, the interaction between the polymerase and the template nucleic acid in the presence of a nucleotide is monitored utilizing intrinsic signals from the polymerase including, but not limited to, Raman signature, tryptophan, 2-aminopurine or other intrinsic fluorescence. Intrinsic fluorescence of polymerase amino acids can be exploited to detect polymerase conformational changes that occur during one or more steps of a sequencing method disclosed herein, for example closed-complex formation or release. Amino acids with intrinsic fluorescence include tryptophan, tyrosine, and phenylalanine. Optionally, one or more polymerase amino acids are mutated to comprise a tryptophan, tyrosine, or phenylalanine residue. Polymerases may be modified by any means, including genetic or chemical modification, to comprise additional amino acids with intrinsic fluorescence. Optionally, intrinsic fluorescence is influenced by the proximity of other amino acids which may cause quenching of fluorescence, such as those amino acids having protonated groups (e.g., aspartic acid, glutamic acid). Optionally, a tryptophan residue of a polymerase is buried in a hydrophobic core, when the polymerase is configured in a closed-complex, and exposed to an aqueous environment, when the polymerase is released or not engaged in a closed-complex confirmation. The emission spectrum of the tryptophan is different depending on the environment (hydrophilic or hydrophobic), allowing for the detection of a closed-complex. Optionally, intrinsic fluorescence of a polymerase is used to identify conformational changes during a sequencing reaction. In one example, intrinsic fluorescence emissions from tryptophan residues of a polymerase are monitored using techniques similar to those referenced in Yu-Chih Tsai, Zhinan Jin, and Kenneth A. Johnson, "Site-Specific Labeling of T7 DNA Polymerase with a Conformationally Sensitive Fluorophore and Its Use in Detecting Single-Nucleotide Polymorphisms," Analytical Biochemistry 384, no. 1 (Jan. 1, 2009): 136-44, which is herein incorporated in its entirety by reference.

The interaction between the polymerase and the template nucleic acid in the presence of nucleotides can be monitored without the use of a tagged label. The sequencing reaction may be monitored by detecting the change in refractive index, charge detection, Raman scattering detection, ellipsometry detection, pH detection, size detection, mass detection, surface plasmon resonance, guided mode resonance, nanopore optical interferometry, whispering gallery mode resonance, nanoparticle scattering, photonic crystal, quartz crystal microbalance, bio-layer interferometry, vibrational detection, pressure detection and other label free detection schemes that detect the added mass or refractive index due to polymerase binding in a closed-complex with a template nucleic acid.

Optionally, a Raman signature of a polymerase is exploited to detect polymerase conformational changes that occur during one or more steps of a sequencing method disclosed herein, for example closed-complex formation or release. Optionally, during one or more steps of a nucleic acid sequencing method described herein, light is directed to the sequencing reaction mixture in the visible, near infrared, or near ultraviolet range. The light interacts with molecular vibrations or other excitations in the reaction, resulting in the energy of the light being shifted. The shift in energy provides information about the vibrational modes of the reaction and therefore provides information on the configurations of reaction components (e.g., polymerase). The sequencing methods of this disclosure may be detected with surface enhanced Raman, resonance Raman, tip-enhanced Raman, polarized Raman, stimulated Raman, transmission Raman, spatially offset Raman, and hyper Raman spectroscopy.

Optionally, detecting a change in refractive index is accomplished in one or a combination of means, including, but not limited to, surface plasmon resonance sensing, localized plasmon resonance sensing, plasmon-photon coupling sensing, transmission sensing through sub-wavelength nanoholes (enhanced optical transmission), photonic crystal sensing, interferometry sensing, refraction sensing, guided mode resonance sensing, ring resonator sensing, or ellipsometry sensing. Optionally, nucleic acid molecules may be localized to a surface, wherein the interaction of polymerase with nucleic acids in the presence of various nucleotides may be measured as a change in the local refractive index.

Optionally, the template nucleic acid is tethered to or localized appropriately on or near a surface, such that the interaction of polymerase and template nucleic acid in the presence of nucleotides changes the light transmitted across or reflected from the surface. The surface may contain nanostructures. Optionally, the surface is capable of sustaining plasmons or plasmon resonance. Optionally, the surface is a photonic substrate, not limited to a resonant cavity, resonant ring or photonic crystal slab. Optionally, the surface is a guided mode resonance sensor. Optionally, the nucleic acid is tethered to, or localized appropriately on or near a nanohole array, a nanoparticle or a microparticle, such that the interaction of polymerase and template nucleic acid in the presence of nucleotides changes the absorbance, scattering, reflection or resonance of the light interacting with the microparticle or nanoparticle.

Optionally, a nanohole array on a gold surface is used as a refractive index sensor. The template nucleic acid may be attached to a metal surface by standard thiol chemistry, incorporating the thiol group on one of the primers used in a PCR reaction to amplify the DNA. When the dimensions of the nanohole array are appropriately tuned to the incident light, binding of the polymerase to the template nucleic acid in the presence of nucleotides can be monitored as a change in light transmitted across the nanoholes. For both the labeled and label-free schemes, simple and straightforward measurement of equilibrium signal intensity may reveal the formation of a stable closed-complex.

Optionally, nucleic acid molecules are localized to a surface capable of sustaining surface plasmons, wherein the change in refractive index caused by the polymerase interaction with localized nucleic acids may be monitored through the change in the properties of the surface plasmons, wherein further, said properties of surface plasmons may include surface plasmon resonance. Surface plasmons, localized surface plasmons (LSP), or surface plasmon polaritons (SPP), arise from the coupling of electromagnetic waves to plasma oscillations of surface charges. LSPs are confined to nanoparticle surfaces, while SPPs and are confined to high electron density surfaces, at the interface between high electron mobility surfaces and dielectric media. Surface plasmons may propagate along the direction of the interface, whereas they penetrate into the dielectric medium only in an evanescent fashion. Surface plasmon resonance conditions are established when the frequency of incident electromagnetic radiation matches the natural frequency of oscillation of the surface electrons. Changes in dielectric properties at the interface, for instance due to binding or molecular crowding, affects the oscillation of surface electrons, thereby altering the surface plasmon resonance wavelength. Surfaces capable of surface plasmon resonance include, in a non-limiting manner, nanoparticles, clusters and aggregates of nanoparticles, continuous planar surfaces, nanostructured surfaces, and microstructured surfaces. Materials such as gold, silver, aluminum, high conductivity metal oxides (e.g., indium tin oxide, zinc oxide, tungsten oxide) are capable of supporting surface plasmon resonance at their surfaces.

Optionally, a single nucleic acid molecule, or multiple clonal copies of a nucleic acid, are attached to a nanoparticle, such that binding of polymerase to the nucleic acid causes a shift in the localized surface plasmon resonance (LSPR). Light incident on the nanoparticles induces the conduction electrons in them to oscillate collectively with a resonant frequency that depends on the nanoparticles' size, shape and composition. Nanoparticles of interest may assume different shapes, including spherical nanoparticles, nanorods, nanopyramids, nanodiamonds, and nanodiscs. As a result of these LSPR modes, the nanoparticles absorb and scatter light so intensely that single nanoparticles are easily observed by eye using dark-field (optical scattering) microscopy. For example, a single 80-nm silver nanosphere scatters 445-nm blue light with a scattering cross-section of $(3 \times 10^{-2})$ m$^2$, a million fold greater than the fluorescence cross-section of a fluorescein molecule, and a thousand fold greater than the cross-section of a similarly sized nanosphere filled with fluorescein to the self-quenching limit. Optionally, the nanoparticles are plasmon-resonant particles configured as ultra-bright, nanosized optical scatters with a scattering peak anywhere in the visible spectrum. Plasmon-resonant particles are advantageous as they do not bleach. Optionally, plasmon-resonant particles are prepared, coated with template nucleic acids, and provided in a reaction mixture comprising a polymerase and one or more nucleotides, wherein a polymerase-template nucleic acid-particle interaction is detected. One or more of the aforementioned steps may be based on or derived from one or more methods disclosed in Sheldon Schultz et al., "Single-Target Molecule Detection with Nonbleaching Multicolor Optical Immunolabels," *Proceedings of the National Academy of Sciences* 97, no. 3 (Feb. 1, 2000): 996-1001, which is incorporated by reference herein in its entirety.

The very large extinction coefficients at resonant wavelength enables noble-metal nanoparticles to serve as extremely intense labels for near-surface interactions. Optionally, polymerase interaction with nanoparticle-localized DNA results in a shift in the resonant wavelength. The change in resonant wavelength due to binding or binding interactions can be measured in one of many ways. Optionally, the illumination is scanned through a range of wavelengths to identify the wavelength at which maximum scattering is observed at an imaging device. Optionally, broadband illumination is utilized in conjunction with a dispersive element near the imaging device, such that the resonant peak is identified spectroscopically. Optionally, the nanoparticle system may be illuminated at its resonant wavelength, or near its resonant wavelength, and any binding interactions may be observed as a drop in intensity of light scattered as the new resonant wavelength shifts away from the illumination wavelength. Depending on the positioning of the illuminating wavelength, interactions may even appear as an increase in nanoparticle scattering as the resonance peak shifts towards the illumination wavelength. Optionally, DNA-attached-nanoparticles may be localized to a surface, or, alternatively, the DNA-attached-nanoparticles may be suspended in solution. A comprehensive review of biosensing using nanoparticles is described in Jeffrey N. Anker et al., "Biosensing with Plasmonic Nanosensors," Nature Materials 7, no. 6 (June 2008): 442-53, which is incorporated in its entirety herein by reference.

Optionally, nano-features capable of LSPR are lithographically patterned on a planar substrate. The two dimensional patterning of nano-features has advantages in multiplexing and high-throughput analysis of a large number of different nucleic acid molecules. Optionally, gold nanoposts are substrates for surface plasmon resonance imaging detection of polymerase-template nucleic acid interactions, wherein the nucleic acids are attached to the nanoposts. Nanostructure size and period can influence surface plasmon resonance signal enhancement, optionally, providing a 2, 3, 4, 5, 6, 7, 8-fold or higher signal amplification when compared to control films.

Optionally, surface plasmon resonance may be sustained in planar surfaces. A number of commercial instruments based on the Kretschmann configuration (e.g., Biacore, Uppsala, Sweden) and surface plasmon resonance imaging (e.g., GWC Technologies, Madison, Wis., or Horiba, Kyoto, Japan) are readily available in the market, and have well established protocols to attach DNA to their surface, both in a single spot and in multiplexed array patterns. In the Kretschmann configuration, a metal film, typically gold is evaporated onto the side of a prism and incident radiation is launched at an angle to excite the surface plasmons. An evanescent wave penetrates through the metal film exciting plasmons on the other side, where it may be used to monitor near-surface and surface interactions near the gold film. At the resonant angle, the light reflected from the prism-gold interface is severely attenuated. Assuming fixed wavelength illumination, binding interactions may be examined by monitoring both the intensity of the reflected light at a fixed angle close to the resonant angle, as well as by monitoring the changes in angle of incidence required to establish surface plasmon resonance conditions (minimum reflectivity). When a 2D imaging device such as a CCD or CMOS camera is utilized to monitor the reflected light, the entire illumination area may be imaged with high resolution. This method is called surface plasmon resonance imaging (SPRi). It allows high throughput analysis of independent regions on the surface simultaneously. Broadband illumination may also be used, in a fixed angle configuration, wherein the wavelength that is coupled to the surface plasmon resonance is identified spectroscopically by looking for dips in the reflected spectrum. Surface interactions are monitored through shifts in the resonant wavelength.

Surface plasmon resonance is an extremely well established method to monitor protein-nucleic acid interactions, and there exist many standard protocols both for nucleic acid attachment as well for analyzing the data. Illustrative references from literature include Bongsup Cho et al., "Binding Kinetics of DNA-Protein Interaction Using Surface Plasmon Resonance," *Protocol Exchange*, May 22, 2013, and, Jennifer M. Brockman, Anthony G. Frutos, and Robert M. Corn, "A Multistep Chemical Modification Procedure To Create DNA Arrays on Gold Surfaces for the Study of Protein-DNA Interactions with Surface Plasmon Resonance Imaging," *Journal of the American Chemical Society* 121, no. 35 (Sep. 1, 1999): 8044-51, both of which are included herein in their entireties by reference.

Polymerase/nucleic-acid interactions may be monitored on nanostructured surfaces capable of sustaining localized surface plasmons. Optionally, polymerase/nucleic-acid interactions may be monitored on nanostructured surfaces capable of sustaining surface plasmon polaritons.

Optionally, polymerase/nucleic-acid interactions may be monitored on nanostructured surfaces capable of sustaining localized surface plasmons. Optionally, polymerase/nucleic-acid interactions may be monitored on nanostructured surfaces capable of sustaining surface plasmon polaritons.

Optionally, extraordinary optical transmission (EOT) through a nanoholes array may be used to monitor nucleic-acid/polymerase interactions. Light transmitted across sub-wavelength nanoholes in plasmonic metal films is higher than expected from classical electromagnetic theory. This enhanced optical transmission may be explained by considering plasmonic resonant coupling to the incident radiation, whereby at resonant wavelength, a larger than anticipated fraction of light is transmitted across the metallic nanoholes. The enhanced optical transmission is dependent on the dimensions and pitch of the nanoholes, properties of the metal, as well as the dielectric properties of the medium on either side of the metal film bearing the nanoholes. In the context of a biosensor, the transmissivity of the metallic nanohole array depends on the refractive index of the medium contacting the metal film, whereby, for instance, the interaction of polymerase with nucleic acid attached to the metal surface may be monitored as a change in intensity of light transmitted across the nanoholes array. The elegance of the EOT/plasmonic nanohole array approach is that the instrumentation and alignment requirements of surface plasmon resonance may be replaced by very compact optics and imaging elements. For instance, just a low power LED illumination and inexpensive CMOS or CCD camera may suffice to implement robust EOT plasmonic sensors. An exemplary nanohole array-based surface plasmon resonance sensing device is described in C. Escobedo et al., "Integrated Nanohole Array Surface Plasmon Resonance Sensing Device Using a Dual-Wavelength Source," *Journal of Micromechanics and Microengineering* 21, no. 11 (Nov. 1, 2011): 115001, which is herein incorporated by reference in its entirety.

The plasmonic nanohole array may be patterned on an optically opaque layer of gold (greater than 50 nm thickness) deposited on a glass surface. Optionally, the plasmonic nanohole array may be patterned on an optically thick film of aluminum or silver deposited on glass. Optionally, the nanohole array is patterned on an optically thick metal layer deposited on low refractive index plastic. Patterning plasmonic nanohole arrays on low refractive index plastics enhances the sensitivity of the device to refractive index changes by better matching the refractive indices on the two sides of the metal layer. Optionally, refractive index sensitivity of the nanohole array is increased by increasing the distance between holes. Optionally, nanohole arrays are fabricated by replication, for example, by embossing, casting, imprint-lithography, or template-stripping. Optionally, nanohole arrays are fabricated by self-assembly using colloids. Optionally, nanohole arrays are fabricated by projection direct patterning, such as laser interference lithography.

A nano-bucket configuration may be preferable to a nanohole configuration. In the nanohole configuration, the bottom of the nano-feature is glass or plastic or other appropriate dielectric, whereas in the nano-bucket configuration, the bottom of the nano-feature comprises a plasmonic metal. The nanobucket array configuration may be easier to fabricate in a mass production manner, while maintaining the transmission sensitivity to local refractive index.

Optionally, the nanohole array plasmonic sensing is combined with lens-free holographic imaging for large area imaging in an inexpensive manner. Optionally, a plasmonic biosensing platform comprises a plasmonic chip comprising nanohole arrays, a light-emitting diode source configured to illuminate the chip, and a CMOS imager chip to record diffraction patterns of the nanoholes, which is modulated by molecular binding events on the surface. The binding events may be the formation of a closed-complex between a polymerase and a template nucleic acid in the presence of a nucleotide.

The methods to functionalize surfaces (for nucleic acid attachment) for surface plasmon resonance sensing may be directly applied to EOT nanohole arrays as both sensing schemes employ similar metal surfaces to which nucleic acids need to be attached.

Optionally, the refractive index changes associated with polymerase/nucleic acid interaction may be monitored on nanostructured surfaces that do not support plasmons. Optionally, guided mode resonance may be used to monitor the polymerase/nucleic-acid interaction. Guided-mode resonance or waveguide-mode resonance is a phenomenon wherein the guided modes of an optical waveguide can be excited and simultaneously extracted by the introduction of a phase-matching element, such as a diffraction grating or prism. Such guided modes are also called "leaky modes," as they do not remain guided and have been observed in one and two-dimensional photonic crystal slabs. Guided mode resonance may be considered a coupling of a diffracted mode to a waveguide mode of two optical structured placed adjacent or on top of each other. For instance, for a diffraction grating placed on top of an optical waveguide, one of the diffracted modes may couple exactly into the guided mode of the optical waveguide, resulting in propagation of that mode along the waveguide. For off-resonance conditions, no light is coupled into the waveguide, so the structure may appear completely transparent (if dielectric waveguides are used). At resonance, the resonant wavelength is strongly coupled into the waveguide, and may be couple out of the structure depending on downstream elements from the grating-waveguide interface. In cases where the grating coupler is extended over the entire surface of the waveguide, the light cannot be guided, as any light coupled in is coupled out at the next grating element. Therefore, in a grating waveguide structure, resonance is observed as a strong reflection peak, whereas the structure is transparent to off-resonance conditions. The resonance conditions are dependent on angle, grating properties, polarization and wavelength of incident light. For cases where the guided mode propagation is not present, for instance due to a grating couple to the entire surface of the waveguide, the resonant mode may also be called leaky-mode resonance, in light of the strong optical confinement and evanescent propagation of radiation in a transverse direction from the waveguide layer. Change in dielectric properties near the grating, for instance due to binding of biomolecules affects the coupling into the waveguide, thereby altering the resonant conditions. Optionally, where nucleic acid molecules are attached to the surface of grating waveguide structures, the polymerase/nucleic-acid interaction may be monitored as a change in wavelength of the leaky mode resonance.

A diffraction element may be used directly on a transparent substrate without an explicit need for a waveguide element. The change in resonance conditions due to interactions near the grating nanostructure may be monitored as resonant wavelength shifts in the reflected or transmitted radiation.

Reflected light from a nucleic acid attached guided mode resonant sensor may be used to monitor the polymerase/nucleic-acid interaction. A broadband illumination source may be employed for illumination, and a spectroscopic examination of reflected light could reveal changes in local refractive index due to polymerase binding.

Optionally, a broadband illumination may be used and the transmitted light may be examined to identify resonant shifts due to polymerase interaction. A linearly polarized narrow band illumination may be used, and the transmitted light may be filtered through a cross-polarizer; wherein the transmitted light is completely attenuated due to the crossed polarizers excepting for the leaky mode response whose polarization is modified. This implementation converts refractive index monitoring to a simple transmission assay that may be monitored on inexpensive imaging systems. Published material describe the assembly of the optical components. See, Yousef Nazirizadeh et al., "Low-Cost Label-Free Biosensors Using Photonic Crystals Embedded between Crossed Polarizers," *Optics Express* 18, no. 18 (Aug. 30, 2010): 19120-28, which is incorporated herein by reference in its entirety.

Alongside nanostructured surfaces, plain, un-structured surfaces may also be used advantageously for monitoring refractive index modulations. Optionally, interferometry may be employed to monitor the interaction of polymerase with nucleic acid bound to an un-structured, optically transparent substrate. Nucleic acid molecules may be attached to the top surface of a glass slide (by any means known in the art), and the system illuminated from the bottom surface of the glass slide. There are two reflection surfaces in this configuration, one reflection from the bottom surface of the glass slide, and the other from the top surface which has nucleic acid molecules attached to it. The two reflected waves may interfere with each other causing constructive or destructive interference based on the path length differences, with the wave reflected from the top surface modulated by the changes in dielectric constant due to the bound nucleic acid molecules (and subsequently by the interaction of polymerase with the bound nucleic acid molecules). With the reflection from the bottom surface unchanged, any binding to the nucleic acid molecules may be reflected in the phase difference between the beams reflected from the top and bottom surfaces, which in turn affects the interference pattern that is observed. Optionally, bio-layer interferometry is used to monitor the nucleic acid/polymerase interaction. Bio-layer interferometry may be performed on commercial devices such as those sold by Pall Forte Bio corporation (Menlo Park, Calif.).

Optionally, the reflected light from the top surface is selectively chosen by using focusing optics. The reflected light from the bottom surface is disregarded because it is not in the focal plane. Focusing only on the nucleic-acid-attached top surface, the light collected by the focusing lens comprises a planar wave, corresponding to the partially reflected incident radiation, and a scattered wave, corresponding to the radiations scattered in the collection direction by molecules in the focal plane. These two components may be made to interfere if the incident radiation is coherent. This scattering based interferometric detection is extremely sensitive and can be used to detect down to single protein molecules.

Following the examination step, where the identity of the next base has been identified via formation of a closed-complex, the reaction conditions may be reset, recharged, or modified as appropriate, in preparation for the optional incorporation step or an additional examination step. Optionally, the identity of the next base has been identified without chemically incorporating a nucleotide. Optionally, the identity of the next base is identified with chemical incorporation of a nucleotide, wherein a subsequent nucleotide incorporation has been inhibited. Optionally, all components of the examination step, excluding the template nucleic acid being sequenced, are removed or washed away, returning the system to the pre-examination condition. Optionally, partial components of the examination step are removed. Optionally, additional components are added to the examination step.

Optionally, reversible terminator nucleotides are used in the incorporation step to ensure one, and only one nucleotide is incorporated per cycle. No labels are required on the reversible terminator nucleotides as the base identity is known from the examination step. Non-fluorescently labeled reversible terminators are readily available from commercial suppliers. Non-labeled reversible terminator nucleotides are expected to have much faster incorporation kinetics compared to labeled reversible terminators due to their smaller steric footprint, and similar size to natural nucleotides.

Disclosed herein, in part, are reagent cycling sequencing methods, wherein sequencing reagents are introduced, one after another, for every cycle of examination and/or incorporation. Optionally, the sequencing reaction mixture comprises a polymerase, a primed template nucleic acid, and at least one type of nucleotide. Optionally, the nucleotide and/or polymerase are introduced cyclically to the sequencing reaction mixture. Optionally, the sequencing reaction mixture comprises a plurality of polymerases, primed template nucleic acids, and nucleotides. Optionally, a plurality of nucleotides and/or a plurality of polymerases are introduced cyclically to the sequencing reaction mixture. Optionally, the examination step of the sequencing reaction has a different composition than the incorporation step of the sequencing reaction.

As provided herein, a polymerase refers to a single polymerase or a plurality of polymerases. As provided herein, a primed template nucleic acid or template nucleic acid refers to a single primed template nucleic acid or single template nucleic acid, or a plurality of primed template nucleic acids or a plurality of template nucleic acids. As provided herein, a nucleotide refers to one nucleotide or a plurality of nucleotides. As provided herein, a single nucleotide is one nucleotide. Optionally, the sequencing reaction nucleotides include, but are not limited to, 1, 2, 3, or 4 of the following nucleotides: dATP, dGTP, dCTP, and dTTP. Optionally, reagent cycling involves immobilizing a template nucleic acid to a platform, washing away the current reaction mixture, and adding a new reaction mixture to the template nucleic acid.

Optionally, one or more nucleotides are sequentially added to and removed from the sequencing reaction. Optionally, 1, 2, 3, 4, or more types of nucleotides are added to and removed from the reaction mixture. For example, one type of nucleotide is added to the sequencing reaction, removed, and replaced by another type of nucleotide. Optionally, a nucleotide type present during the examination step is different from a nucleotide type present during the incorporation step. Optionally, a nucleotide type present during one examination step is different from a nucleotide type present during a sequential examination step (i.e., the sequential examination step is performed prior to an incorporation step). Optionally, 1, 2, 3, 4 or more types of nucleotides are present in the examination reaction mixture and 1, 2, 3, 4, or more types of nucleotides are present in the incorporation reaction mixture.

Optionally, a polymerase is cyclically added to and removed from the sequencing reaction. One or more different types of polymerases may be cyclically added to and removed from the sequencing reaction. Optionally, a polymerase type present during the examination step is different from a polymerase type present during the incorporation step. A polymerase type present during one examination step may be different from a polymerase type present during a sequential examination step (i.e. the sequential examination step is performed prior to an incorporation step).

Optionally, reagents conditions such as the presence of reagents, pH, temperature, and ionic strength are varied throughout the sequencing reaction. Optionally, a metal is cyclically added to and removed from the sequencing reaction. For example, a catalytic metal ion may be absent during an examination step and present during an incorporation step. Alternatively, a polymerase inhibitor may be present during an examination step and absent during an incorporation step. Optionally, reaction components that are consumed during the sequencing reaction are supplemented with the addition of new components at any point during the sequencing reaction.

Nucleotides can be added one type at a time, with the polymerase, to a reaction condition which favors closed-complex formation. The polymerase binds only to the template nucleic acid if the next correct nucleotide is present. A wash step after every nucleotide addition ensures all excess polymerases and nucleotides not involved in a closed-complex are removed from the reaction mixture. If the nucleotides are added one at a time, in a known order, the next base on the template nucleic acid is determined by the formation of a closed-complex when the added nucleotide is the next correct nucleotide. The closed-complex may be identified by both the conformational change and the increased stability of the polymerase-template nucleic acid-nucleotide interaction. Optionally, the stability of the closed-complex formed in the presence of the next correct nucleotide is at least an order of magnitude greater than the unstable interactions of the polymerase with the template nucleic acid in the presence of incorrect nucleotides. The use of a wash step ensures that there are no unbound nucleotides and polymerases and that the only nucleotides present in the reaction are those sequestered in a closed-complex with a polymerase and a template nucleic acid. Once the next base on the template nucleic acid is determined, the next correct nucleotide sequestered in the closed-complex may be incorporated by flowing in reaction conditions that favor dissociation or destabilization of the closed-complex and extending the template nucleic acid primer strand by one base (incorporation). Therefore, the wash step ensures that the only nucleotide incorporated is the next correct nucleotide from the closed-complex. This reagent cycling method may be repeated and the nucleic acid sequence determined. This reagent cycling method may be applied to a single template nucleic acid molecule, or to collections of clonal populations such as PCR products or rolling-circle amplified DNA. Many different templates can be sequenced in parallel if they are arrayed, for instance, on a solid support. Optionally, the wash step destabilizes binary complex formation. Optionally, the washing is performed for a duration of time which ensures that the binary complex is removed, leaving the stabilized closed-complex in the reaction mixture. Optionally, the wash step includes washing the reaction with a high ionic strength or a high pH solution.

Optionally, the incorporation step is a three stage process. In the first stage, all four nucleotide types are introduced into a reaction comprising a primed template nucleic acid, with a high fidelity polymerase, in reaction conditions which favor the formation of a closed-complex, and the next correct nucleotides are allowed to form stable closed-complexes with the template nucleic acid. In a second stage, excess nucleotides and unbound polymerase are washed away. In a third stage, reaction conditions are modified so that the closed-complex is destabilized and the sequestered nucleotides within the closed complex become incorporated into the 3' end of the template nucleic acid primer. Formation of tight polymerase-nucleic acid complexes in the incorporation step can be enabled by standard techniques such as fusing a non-specific DNA binding domain to the polymerase (e.g., Phusion polymerase), and utilizing high concentrations of nucleotides to ensure correct nucleotides are always present in the closed-complex.

Polymerase molecules bind to primed nucleic acid molecules in a fingers-closed conformation in the presence of the next correct nucleotide even in the absence of divalent metal ions that are typically required for polymerase synthesis reactions. The conformational change traps the nucleotide complementary to the next template base within the active site of the polymerase. Optionally, the formation of the closed-complex may be used to determine the identity of next base on the template nucleic acid. Optionally, the primed template nucleic acids may be contacted serially by different nucleotides in the presence of polymerase, in the absence of catalytic divalent metal ions; wherein the formation of a closed-complex indicates the nucleotide currently in contact with the template nucleic acid is the complementary nucleotide to the next base on the nucleic acid. A known order of nucleotides (in the presence of polymerase, absence of catalytic metal ions) brought into contact with the template nucleic acid ensures facile identification of the complementary nucleotide based on the particular position in the order that induces closed-complex formation. Optionally, an appropriate wash step may be performed after every nucleotide addition to ensure removal of all excess enzymes and nucleotides, leaving behind only the polymerase that are bound to nucleic acids in a closed-complex with the next correct nucleotide at the active site. The closed-complex may be identified by means that reveal the conformational change of the polymerase in the closed conformation or by means that reveal the increased stability of the polymerase/nucleic-acid/next-correct-nucleotide complex compared to binary polymerase-nucleic acid complexes or compared to unstable interactions between the polymerase, primed template nucleic acid and incorrect nucleotides.

Optionally, the process of identifying the next complementary nucleotide (examination step) comprises the steps of contacting immobilized primed template nucleic acids with an examination mixture comprising polymerase and nucleotides of one kind under conditions that inhibit the chemical incorporation of the nucleotide, removing unbound reagents by a wash step, detecting the presence of polymerase closed-complex on the immobilized nucleic acids, and repeating steps a-c, serially, with nucleotides of different kinds till a closed-complex formation is detected. The closed-complex may be identified by both the conformational change and the increased stability of the polymerase/nucleic-acid/next-correct-nucleotide complex. The wash step in between successive nucleotide additions may be eliminated by the use of detection mechanisms that can detect the formation of the closed-complex with high fidelity, for instance, evanescent wave sensing methods or methods that selectively monitor signals from the closed-complex. The examination steps noted above may be followed by an incorporation step comprising, contacting the closed-complex with catalytic metal ions to covalently add the nucleotide sequestered in the closed complex to the 3' end of the primer. Optionally, the incorporation step may comprise, contacting the immobilized nucleic acids with a pre-incorporation mixture comprising a combination of multiple types of nucleotides and polymerase under conditions that inhibit the chemical incorporation of the nucleotides; wherein the pre-incorporation mixture may contain additives and solution conditions to ensure highly efficient closed-complex formation (e.g., low-salt conditions). The methods may also include performing a wash step to remove unbound reagents and providing the immobilized complexes with an incorporation mixture, comprising catalytic metal ions, to chemically incorporate nucleotides sequestered within the active site of the polymerase. The pre-incorporation mixture ensures highly efficient closed-complex formation, while the wash step and incorporation mixture ensure the addition of a single nucleotide to the 3' end of the primer. Optionally, the incorporation step may occur directly after examination an addition of one type of nucleotide. For instance, a repeated pattern used for sequencing may comprise the following flow pattern (i) dATP+/polymerase, (ii) Wash, (iii) Mg, (iv) Wash, (v) dTTP+/polymerase, (vi) Wash, (vii) Mg, (viii) Wash, (ix) dCTP+/polymerase, (x) Wash (xi) Mg, (xii) Wash, (xiii) dGTP+/polymerase, (xiv) Wash, (xv) Mg, (xvi) Wash. Optionally, the repeated pattern used for sequencing may include (i) dATP+/polymerase, (ii) Wash, (iii) dTTP+/polymerase, (iv) Wash, (v) dGTP+/polymerase, (vi) Wash, (vii) dCTP+/polymerase, (viii) Wash, (ix) Pre-incorporation mixture, (x) Wash, (xi) Mg, (xii) Wash. The wash steps typically contain metal ion chelators and other small molecules to prevent accidental incorporations during the examination steps. After the incorporation step, the primer strand is typically extended by one base. Repeating this process, sequential nucleobases of a nucleic acid may be identified, effectively determining the nucleic acid sequence. Optionally, the examination step is performed at high salt conditions, for example, under conditions of 50 mM to 1500 mM salt.

For sequencing applications, it can be advantageous to minimize or eliminate fluidics and reagents exchange. Removing pumps, valves and reagent containers can allow for smaller and less expensive devices. Disclosed herein, in part, are "all-in" sequencing methods, wherein the need to introduce reagents one after another, for every cycle of examination and/or incorporation, is eliminated. Reagents are added only once to the reaction, and sequencing-by-synthesis is performed by manipulating reagents already enclosed within the sequencing reaction. A scheme such as this requires a method to distinguish different nucleotides, a method to synchronize incorporation of nucleotides across a clonal population of nucleic acids and/or across different nucleic acid molecules, and a method to ensure only one nucleotide is added per cycle. Optionally, the sequencing reaction mixture comprises a polymerase, a primed template nucleic acid, and at least one type of nucleotide. Optionally, the sequencing reaction mixture comprises a plurality of polymerases, primed template nucleic acids, and nucleotides. As provided herein, a polymerase refers to a single polymerase or a plurality of polymerases. As provided herein, a primed template nucleic acid or template nucleic acid refers to a single primed template nucleic acid or single template nucleic acid, or a plurality of primed template nucleic acids or a plurality of template nucleic acids. As provided herein, a nucleotide refers to one nucleotide or a plurality of nucleotides. As provided herein, a single nucleotide is one nucleotide. Optionally, the sequencing reaction nucleotides include, but are not limited to, 1, 2, 3, or 4 of the following nucleotides: dATP, dGTP, dCTP, and dTTP.

Optionally, the examination step and the incorporation step take place in a single sequencing reaction mixture.

Optionally, 1, 2, 3, 4 or more types of nucleotides (e.g. dATP, dGTP, dCTP, dTTP) are present in the reaction mixture together at the same time, wherein one type of nucleotide is a next correct nucleotide. The reaction mixture further comprises at least one polymerase and at least one primed template nucleic acids. Optionally, the template nucleic acid is a clonal population of template nucleic acids. Optionally, the polymerase, primed template nucleic acid, and the nucleotide form a closed-complex under examination reaction conditions.

In the provided methods, four types of nucleotides can be present at distinct and different concentrations wherein the diffusion and binding time of the polymerase to the template nucleic acid is different for each of the four nucleotides, should they be the next correct nucleotide, due to the different concentrations of the four nucleotides. For example, the nucleotide at the highest concentration would bind to its complementary base on the template nucleic acid a fast time, and the nucleotide at the lowest concentration would bind to its complementary base on the template nucleic acid a slower time; wherein binding to the complementary base on the template nucleic acid refers to the polymerase binding to the template nucleic acid with the next correct nucleotide in a closed closed-complex. The identity of the next correct nucleotide is therefore determined by monitoring the rate or time of binding of polymerase to the template nucleic acid in a closed-complex. Optionally, the four types of nucleotides may be distinguished by their concentration, wherein the different concentrations of the nucleotides result in measurably different on-rates for the polymerase binding to the nucleic acid. Optionally, the four types of nucleotides may be distinguished by their concentration, wherein the different concentrations of the nucleotides result in measurably different on-rates for the formation of a stabilized closed-complex. Optionally, the polymerase is labeled. In some instances the polymerase is not labeled and any label free detection method disclosed herein or known in the art is employed. Optionally, the binding of the polymerase to the nucleic acid is monitored via a detectable feature of the polymerase. Optionally, the formation of a stabilized closed-complex is monitored via a detectable feature of the polymerase. A detectable feature of the polymerase may include, but is not limited to, optical, electrical, thermal, colorimetric, mass, and any combination thereof.

Optionally, 1, 2, 3, 4, or more nucleotides types (e.g., dATP, dTTP, dCTP, dGTP) are tethered to 1, 2, 3, 4, or more different polymerases; wherein each nucleotide type is tethered to a different polymerase and each polymerase has a different tag or a feature from the other polymerases to enable its identification. All tethered nucleotide types can be added together to a sequencing reaction mixture forming a closed-complex comprising a tethered nucleotide-polymerase; the closed-complex is monitored to identify the polymerase, thereby identifying the next correct nucleotide to which the polymerase is tethered. The tethering may occur at the gamma phosphate of the nucleotide through a multi-phosphate group and a linker molecule. Such gamma-phosphate linking methods are standard in the art, where a fluorophore is attached to the gamma phosphate linker. The tags include, but are not limited to, optical, electrical, thermal, colorimetric, mass, or any other detectable feature. Optionally, different nucleotide types are identified by distinguishable tags. Optionally, the distinguishable tags are attached to the gamma phosphate position of each nucleotide.

Optionally, the sequencing reaction mixture comprises a catalytic metal ion. Optionally, the catalytic metal ion is available to react with a polymerase at any point in the sequencing reaction in a transient manner. To ensure robust sequencing, the catalytic metal ion is available for a brief period of time, allowing for a single nucleotide complementary to the next base in the template nucleic acid to be incorporated into the 3' end of the primer during an incorporation step. In this instance, no other nucleotides, for example, the nucleotides complementary to the bases downstream of the next base in the template nucleic acid, are incorporated. Optionally, the catalytic metal ion magnesium is present as a photocaged complex (e.g., DM-Nitrophen) in the sequencing reaction mixture such that localized UV illumination releases the magnesium, making it available to the polymerase for nucleotide incorporation. Furthermore, the sequencing reaction mixture may contain EDTA, wherein the magnesium is released from the polymerase active site after catalytic nucleotide incorporation and captured by the EDTA in the sequencing reaction mixture, thereby rendering magnesium incapable of catalyzing a subsequent nucleotide incorporation.

Thus, in the provided methods, a catalytic metal ion can be present in a sequencing reaction in a chelated or caged form from which it can be released by a trigger. For example, the catalytic metal ion catalyzes the incorporation of the closed-complex next correct nucleotide, and, as the catalytic metal ion is released from the active site, it is sequestered by a second chelating or caging agent, disabling the metal ion from catalyzing a subsequent incorporation. The localized release of the catalytic metal ion from its cheating or caged complex is ensured by using a localized uncaging or un-chelating scheme, such as an evanescent wave illumination or a structured illumination. Controlled release of the catalytic metal ions may occur for example, by thermal means. Controlled release of the catalytic metal ions from their photocaged complex may be released locally near the template nucleic acid by confined optical fields, for instance by evanescent illumination such as waveguides or total internal reflection microscopy. Controlled release of the catalytic metal ions may occur for example, by altering the pH of the solution near the vicinity of the template nucleic acid. Chelating agents such as EDTA and EGTA are pH dependent. At a pH below 5, divalent cations $Mg^{2+}$ and $Mn^{2+}$ are not effectively chelated by EDTA. A method to controllably manipulate the pH near the template nucleic acid allows the controlled release of a catalytic metal ion from a chelating agent. Optionally, the local pH change is induced by applying a voltage to the surface to which the nucleic acid is attached. The pH method offers an advantage in that that metal goes back to its chelated form when the pH is reverted back to the chelating range.

Optionally, a catalytic metal ion is strongly bound to the active site of the polymerase, making it necessary to remove the polymerase from the template nucleic acid after a single nucleotide incorporation. The removal of polymerase may be accomplished by the use of a highly distributive polymerase, which falls off the 3' end of the strand being synthesized (primer) after the addition of every nucleotide. The unbound polymerase may further be subjected to an electric or magnetic field to remove it from the vicinity of the nucleic acid molecules. Any metal ions bound to the polymerase may be sequestered by chelating agents present in the sequencing reaction mixture, or by molecules which compete with the metal ions for binding to the active site of the polymerase without disturbing the formation of the closed-complex. The forces which remove or move the polymerase away from the template nucleic acid (e.g., electric field, magnetic field, and/or chelating agent) may be terminated, allowing for the polymerase to approach the template nucleic acid for another round of sequencing (i.e., examination and incorporation). The next round of sequencing, in a non-limiting example, comprises the formation of a closed-complex, removing unbound polymerase away from the vicinity of the template nucleic acid and/or closed-complex, controlling the release of a catalytic metal ion to incorporate a single nucleotide sequestered within the closed-complex, removing the polymerase which dissociates from the template nucleic acid after single incorporation away from the vicinity of the template nucleic acid, sequestering any free catalytic metal ions through the use of chelating agents or competitive binders, and allowing the polymerase to approach the template nucleic acid to perform the next cycle of sequencing.

Provided herein are polymerase-nucleic acid binding reactions for the identification of a nucleic acid sequence. Nucleic acid sequence identification may include information regarding nucleic acid modifications. Nucleic acid modifications include methylation and hydroxymethylation. Methylation may occur on cytosine bases of a template nucleic acid. DNA methylation may stably alter the expression of genes. DNA methylation is also indicated in the development of various types of cancers, atherosclerosis, and aging. DNA methylation therefore can serve as an epigenetic biomarker for human disease.

Optionally, one or more cytosine methylations on a template nucleic acid are identified during the sequencing by binding methods provided herein. The template nucleic acid may be clonally amplified prior to sequencing, wherein the amplicons comprise the same methylation as their template nucleic acid. Amplification of the template nucleic acids may include the use of DNA methyltransferases to achieve amplicon methylation. The template nucleic acids or amplified template nucleic acids are provided to a reaction mixture comprising a polymerase and one or more nucleotide types, wherein the interaction between the polymerase and nucleic acids is monitored. Optionally, the interaction between the polymerase and template nucleic acid in the presence of a methylated cytosine is different than the interaction in the presence of an unmodified cytosine. Therefore, based on examination of a polymerase-nucleic acid interaction, the identity of a modified nucleotide is determined.

Provided herein, inter alia, are systems for performing sequencing reactions involving the examination of the interaction between a polymerase and a primed template nucleic acid in the presence of nucleotides to identify the next base in the template nucleic acid sequence or to identify the number of nucleotides needed to fill a homopolymer region encountered duting sequencing. Optionally, examination includes monitoring the affinity of the polymerase to the primed template nucleic acid in the presence of nucleotides. Optionally, the polymerase binds transiently with the nucleic acid and the binding kinetics and affinity provides information about the identity of the next base on the template nucleic acid. Optionally, a closed-complex is formed, wherein the reaction conditions involved in the formation of the closed-complex provide information about the next base on the nucleic acid. Optionally, the polymerase is trapped at the polymerization site in its closed complex by one or a combination of means, not limited to, crosslinking of the polymerase domains, crosslinking of the polymerase to the nucleic acid, allosteric inhibition by small molecules, uncompetitive inhibitors, competitive inhibitors, non-competitive inhibitors, and denaturation; wherein the formation of the trapped polymerase complex provides information about the identity of the next base on the nucleic acid template.

Also provided is a system for performing one or more steps of any sequencing method disclosed herein. Optionally, the system includes components and reagents necessary to perform a polymerase and template nucleic acid binding assay in the presence of nucleotides, wherein the template nucleic acid is provided on a nanostructure. Optionally, the system comprises one or more reagents and instructions necessary to bind template DNA molecules onto a nanostructure. For example, the system provides a nanostructure, such as a chip, configured for use with surface plasmon resonance to determine binding kinetics. An example of such a chip is a CM5 sensor S chip (GE Healthcare, Piscatawany, N.J. The system may provide instrumentation such as a SPR instrument (e.g., Biacore). The system may provide streptavidin and/or biotin. Optionally, the system provides biotin-DNA, DNA ligase, buffers, and/or DNA polymerase for preparation of biotinylated template DNA. Optionally, the system provides a gel or reagents (e.g., phenol:chloroform) for biotinylated DNA purification. Alternatively, the system provides reagents for biotinylated template DNA characterization, for example, mass spectrometry or HPLC. Optionally, the system comprises streptavidin, a chip, reagents, instrumentation, and/or instructions for immobilization of streptavidin on a chip. Optionally, a chip is provided in the system already configured for template DNA coating, wherein the chip is immobilized with a reagent capable of binding template nucleic acids or modified template nucleic acids (e.g., biotinylated template DNA). Optionally, the system provides reagents for chip regeneration.

Also provided is a system for performing one or more steps of any sequencing method disclosed herein. Optionally, the system includes components and reagents necessary to perform a polymerase and template nucleic acid binding assay in the presence of nucleotides, wherein the template nucleic acid is provided on a nanoparticle. Optionally, the system comprises one or more reagents and instructions necessary to bind template DNA molecules onto a nanoparticle. The nanoparticle may be configured for the electrochemical detection of nucleic acid-polymerase interaction, for instance, by using gold nanoparticles. Optionally, the DNA-nanoparticle conjugates are formed between aqueous gold colloid solutions and template DNA molecules comprising free thiol or disulfide groups at their ends. The conjugates may comprise clonally amplified populations of DNA molecules which may or may not comprise the same nucleic acid sequence. Optionally, the nanoparticle conjugates are stabilized against flocculation and precipitation at high temperature (e.g., >60° C.) and high ionic strength (e.g., 1M $Na^+$). Optionally, the system provides reagents for preparing template DNA molecules for nanoparticle attachment, including, generating template DNA molecules with disulfides or thiols. Disulfide-containing template nucleic acids may be synthesized using, for example, a 3'-thiol modifier controlled-pore glass (CPG) or by beginning with a universal support CPG and adding a disulfide modifier phosphoramidite as the first monomer in the sequence. The system may provide for nucleic acid synthesis reagents and/or instructions for obtaining disulfide-modified template nucleic acids. Thiol-containing template nucleic acids may also be generated during nucleic acid synthesis with a 5'-tritylthiol modifier phosphoramidite. The system may provide reagents and/or instructions for nanoparticle conjugate purification using for example, electrophoresis or centrifugation. Optionally, nanoparticle conjugates are used to monitor polymerase-template nucleic acid interactions colorimetrically. In this instance, the melting temperature of the nanoparticle conjugate increases in the presence of strong polymerase binding. Therefore the strength of DNA binding can be determined by the change in this melting transition, which is observable by a color change.

Also provided is a system for performing one or more steps of any sequencing method disclosed herein. Optionally, the system includes components and reagents necessary to perform a polymerase and template nucleic acid binding assay in the presence of nucleotides, using a detectable polymerase. Optionally, the polymerase is detectably labeled. Optionally, the polymerase is detected using intrinsic properties of the polymerase, for example, aromatic amino acids. Optionally, the polymerase and template nucleic acids are configured for use in solution, without conjugation to a support. The detectable label on the polymerase may be a fluorophore, wherein fluorescence is used to monitor polymerase-template nucleic acid binding events. Optionally, the detectable polymerase may be used in combination with template nucleic acids in solution, or template nucleic acids conjugated to a support structure. Optionally, one or more cysteine residues of the polymerase is labeled with Cy3-maleimide or Cy3-iodoacetamide. Optionally, the system comprises reagents and/or instructions necessary to prepare fluorescently labeled polymerase molecules. The system may comprise reagents and/or instructions for purification of fluorescently labeled polymerases.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties. All publications, patents, and patent applications mentioned in this specification are herein incorporated by reference to the same extent as if each individual publication, patent, or patent application was specifically and individually indicated to be incorporated by reference.

A number of embodiments have been described. Nevertheless, it will be understood that various modifications may be made. Accordingly, other embodiments are within the scope of the claims.

EXAMPLES

Example 1. Determination of Base Sequence with or without Magnesium in the Binding Step Methods & Materials. Polymerase buffer: 20 mM Tris, ph 8, 300 mM NaCl, 5 mM DTT, 100 µM dNTP, 150 nM Klenow, 0.01% BSA, 0.02% tween-20, 10 mM $MgCl_2$. Exam buffer: 20 mM Tris, ph 8, 300 mM NaCl, 5 mM DTT, 100 µM dNTP, 150 nM Klenow, 0.01% BSA, 0.02% tween-20. Incorporation buffer: 20 mM Tris, ph 8, 300 mM NaCl, 5 mM DTT, 0.01% BSA, 0.02% tween-20, 10 mM $MgCl_2$. Wash Buffer: 20 mM Tris, ph 8, 300 mM NaCl, 5 mM DTT, 0.01% BSA, 0.02% tween-20.

FIG. 1 shows the results of an experiment using non-labeled optical detection methods where magnesium was present or absent in during the binding or examination step. The first flow was dCTP (C:T mismatch) and the second flow was dATP (A:T match). The solid line in FIG. 1 shows the results with Polymerase Buffer. The pre-steady state rate constants were 0.0106 and 0.0084 for the match A and mismatch C steps, respectively. The difference is too small to accurately discriminate the cognate base. The dashed line in FIG. 1 represents a magnesium free examination step in exam buffer, followed by soaking in incorporation buffer. A signal threshold of 1.1 nm could accurately determine the correct base. These results show that the sensing platform was unable to capture transient kinetics that could discriminate a match from mismatch base and would be incapable of sequence determination when magnesium was included in the buffer during examination (Polymerase Buffer, solid line, FIG. 1). In contrast, binding in the absence of magnesium provided very large discrimination between correct and incorrect base (Exam Buffer, dashed line, FIG. 1). The correct base sequence was determined by signal thresholding rather than binding rates.

Example 2: Sequencing Using Bst Enzyme Binding Kinetics

Figure 2:
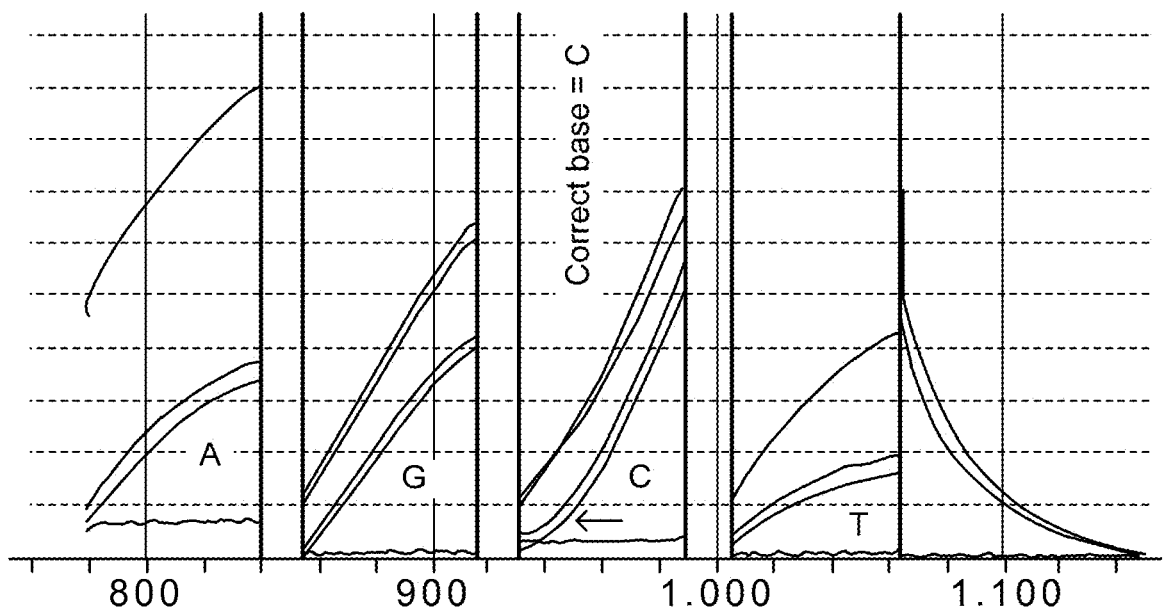
FIG. 2 is a graph showing sequencing using Bst enzyme binding kinetics for determining the correct base using Bst2.0 enzyme and dNTPs.

Binding kinetics can be used determine the correct base or nucleotide during the examination step, i.e., during the formation of a ternary complex between the polymerase, DNA template and nucleotide. This is shown in FIG. 2. Bst enzyme shows a bimodal binding curve when the correct base is present and a basic exponential binding behavior when the incorrect base is presented (FIG. 2). Thus, allowing for discrimination and detection of the correct base or nucleotide during sequencing.

Experimental Conditions.

The FORTEBIO® (Menlo Park, Calif.) Octet instrument (Red384 or qk) uses biolayer interferometry to measure binding reactions at the surface of a fiber optic tip. The tips were functionalized with streptavidin (SA) to enable binding to 5' biotin labeled DNA templates hybridized with a primer that are complementary to sequences near the 3' end of the template. PhiX_matchC and phiX_matchA were loaded onto individual tips. Primer-template was loaded onto the tips at between 100 and 500 nM in 1-2×PBS containing 0.01-0.02% BSA and 0.01-0.02% tween20 (loading buffer). The FP2 primer was in 1.25-2 fold excess over template. Loading was monitored by change in signal and usually reaches a plateau within 5 minutes at 30 degrees C. Tips were soaked in loading buffer for 1-5 minutes to remove unbound DNA material. For base calling, typically, the tips are soaked in solutions containing 1×Taq buffer (10 mM Tris-HCl, 50 mM KCl, pH 8.3 @ 25 C, magnesium free) supplemented with 0.01-0.02% BSA and 0.01-0.02% tween20 (LS buffer), 100 nM polymerase enzyme, 100 μM nucleotide, and varying concentrations of additional NaCl from 50 to 300 mM. In this experiment, for determining the correct base, 30 nM Bst2.0 enzyme, 100 μM dNTP, and LS buffer containing 150 mM NaCl was used. The phiX_matchC duplex will form a ternary complex and show an increase in binding signal because the correct next nucleotide (cognate) is presented. The phiX_matchA should not because it is an incorrect nucleotide (noncognate). After the examination step, the sensors were soaked in LS buffer containing 5 mM Mg, to allow the polymerase to incorporate the nucleotide, which was followed by washing with a LS buffer containing 150 mM NaCl.

Results.

Iterative cycling showed that this method can be used for sequence determination. The table below shows the first 3 bases were correctly identified by this examination method. The 4th base was a no call by the examination method and may reflect multiple additions. This is supported by the fact that the subsequent bases were correctly identified. Overall, 5 of 6 bases were identified correctly. Further, mis-incorporation of an incorrect base was not observed.

TABLE 2

| | Base Identification | | | | |
|---|---|---|---|---|---|
| Expected base | A | G | C | T | Comments |
| C | x | x | C | | |
| G | x | G | | | |
| C | x | x | C | | |
| C | x | x | ? | | Difficult call |
| T | x | x | x | T | |
| T | x | x | x | T | |

Example 3: Sequencing by Binding

In this example, a sequencing reaction was performed using high salt during the examination step followed by an incorporation step.

Experimental Conditions.

The binding/examination buffer used was LS buffer having 250 mM NaCl, 100 μM dGTP, dCTP, dATP, or dTTP, 1.5 mM Sr, 100 nM Klenow exo- polymerase. The incorporation buffer used was LS buffer with 50 mM NaCl, 50 mM MgCl$_2$ and the wash buffer used was LS buffer with 250 mM NaCl. Using a FORTEBIO® Octet Red384 system (Menlo Park, Calif.), sequencing cycles were performed using biotin phiX_matchC template and FP2 primer sequences attached to SA sensor tips. Sequencing steps consisted of the following: a) Examination with dATP b) incorporation, c) wash; d) Examination with dGTP e) incorporation, f) wash; g) Examination with dCTP h) incorporation, i) wash; j) Examination with dTTP k) incorporation, 1) wash, followed by repeat of these steps from a). For base calls, the examination step produced a detectable signal above the baseline from the previous wash step and/or relative to a control sequences.

Results.

Using this method, 12 bases were correctly identified. There were 2 bases that were not identified because binding signal was too low. This experiment identified 12/14 bases correctly as shown in the table below.

TABLE 3

| | Sequence Identification | | | | |
|---|---|---|---|---|---|
| Expected base | G | C | T | A | Comment |
| C | | C | | | |
| G | G | | | | |
| C | | C | | | |
| C | | | | | No call |
| T | | | T | | |
| T | | | T | | |
| C | | C | | | |
| G | G | | | | |
| T | | | T | | |
| A | | | | A | |
| T | | | | | No call |
| G | G | | | | |
| T | | | T | | |
| T | | | T | | |

Example 4: Salt Concentration on Match/Mismatch Base Discrimination

The FORTEBIO® Octet instrument (Red384 or qk) (Menlo Park, Calif.) uses biolayer interferometry to measure binding reactions at the surface of a fiber optic tip. In this example, the tips were functionalized with streptavidin (SA) to enable binding to 5' biotin labeled DNA templates hybridized with a primer that is complementary to sequences near the 3' end of the template.

Experimental Conditions.

PhiX_matchC and phiX_matchA were loaded onto individual tips. Primer-template was loaded onto the tips at between 100 and 500 nM in 1-2×PBS containing 0.01-0.02% BSA and 0.01-0.02% tween20 (loading buffer). The FP2 primer was in 1.25-2 fold excess over template. Loading was monitored by change in signal and usually reaches a plateau within 5 minutes at 30 degrees C. Tips were soaked in Loading buffer for 1-5 minutes to remove unbound DNA material. For base calling, the tips were soaked in solutions containing 1×Taq buffer (10 mM Tris-HCl, 50 mM KCl, pH 8.3 @ 25 C, magnesium free) supplemented with 0.01-0.02% BSA and 0.01-0.02% tween20 (LS buffer), 100 nM polymerase enzyme, 100 µM NTP, and varying concentrations of additional NaCl from 50 to 300 mM. The phiX_matchC duplex will form a ternary complex and show an increase in binding signal because the correct next nucleotide (cognate) is presented. The phiX_matchA should not because it is an incorrect nucleotide (noncognate).

Results.

Figure 3:
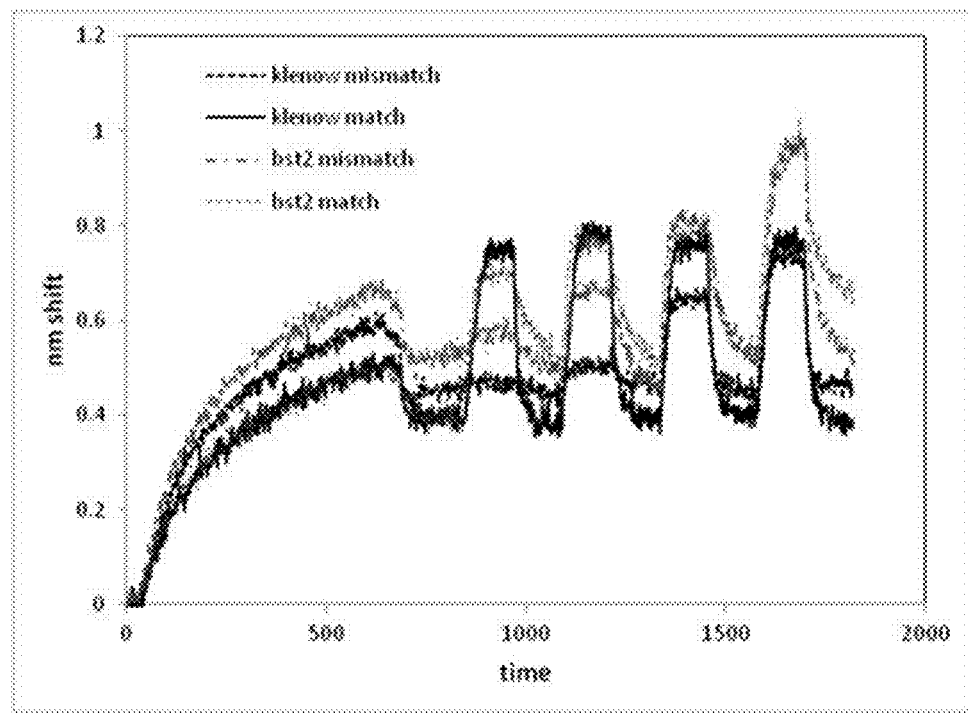
FIG. 3 is a graph showing the effects of salt concentration on match and mismatch base discrimination effects using biolayer interferometry on a FORTEBIO® octet instrument (Menlo Park, Calif.).

At standard reaction conditions both templates bind polymerase enzyme. However, as the salt concentration increases the binding affinity of the noncognate complex decreases while binding affinity of the cognate complex remains high. Thus, the signal to noise ratio (SNR) of base discrimination increases such that the next correct base can be easily identified during this examination step (FIG. 3). Sodium chloride (NaCl) was used in this example but salts such as KCL, $NH_2(SO_4)$, potassium glutamate, and others known in the art can be used. Polymerases that show differences in binding affinity between correct and incorrect nucleotides included klenow, Bst2.0, Bsu, and Taq.

Example 5: Base Discrimination During Dissociation/Wash Step

Examination during both the association and dissociation steps can be used together to improve sequence fidelity. Thus, dissociation kinetics were evaluated to determine if they can be used to determine base identification and increase sequence fidelity.

Experimental Conditions.

In this experiment, phiX_matchC and FP2 primer were loaded onto SA-sensor tips, as described above. Polymerase complex was formed in LS buffer with 100 µM of either dGTP, dCTP, dATP, or dTTP, and 100 nM klenow or Bst2.0 enzyme, and 1 mM $SrCl_2$.

Results.

Figure 4:
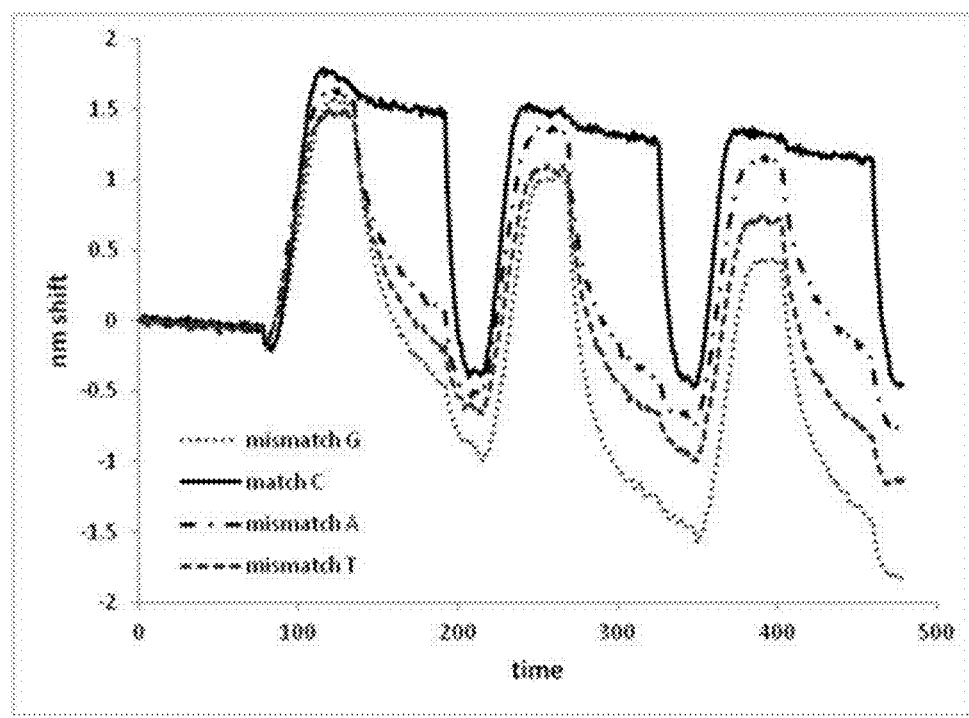
FIG. 4 is a graph showing base discrimination during the wash step, i.e., during dissociation of the polymerase, using phiX_matchC and FP2 primer and klenow or Bst2.0 enzyme, and $SrCl_2$.

In low salt, polymerase binds to DNA template primer efficiently regardless if cognate nucleotide is present or not. In wash buffer (LS buffer+50 mM or 100 mM added NaCl), all complexes dissociate, even $SrCl_2$ cannot stabilize when additional NaCl was present. However, when 50 µM of the same dNTP that was in the binding buffer was added to the wash buffer, then only the complexes with incorrect nucleotides dissociate and the correct ternary complex was stabilized (FIG. 4). Furthermore, it was found that dNTPs were unnecessary in the binding step and could be included during washing. A bound binary complex could still allow the correct base to enter and form a ternary complex when the correct dNTP was subsequently introduced during. Additionally, the fidelity was not affected by the presence of incorrect nucleotides. Thus, the dissociation rates of the polymerase may also be used to determine the correct base in a mixture of dNTPs, e.g., at different concentrations which will dissociate at different rates.

Example 6: Stabilization of Nucleic Acid:Polymerase Complex in Wash Buffer

Figure 5:
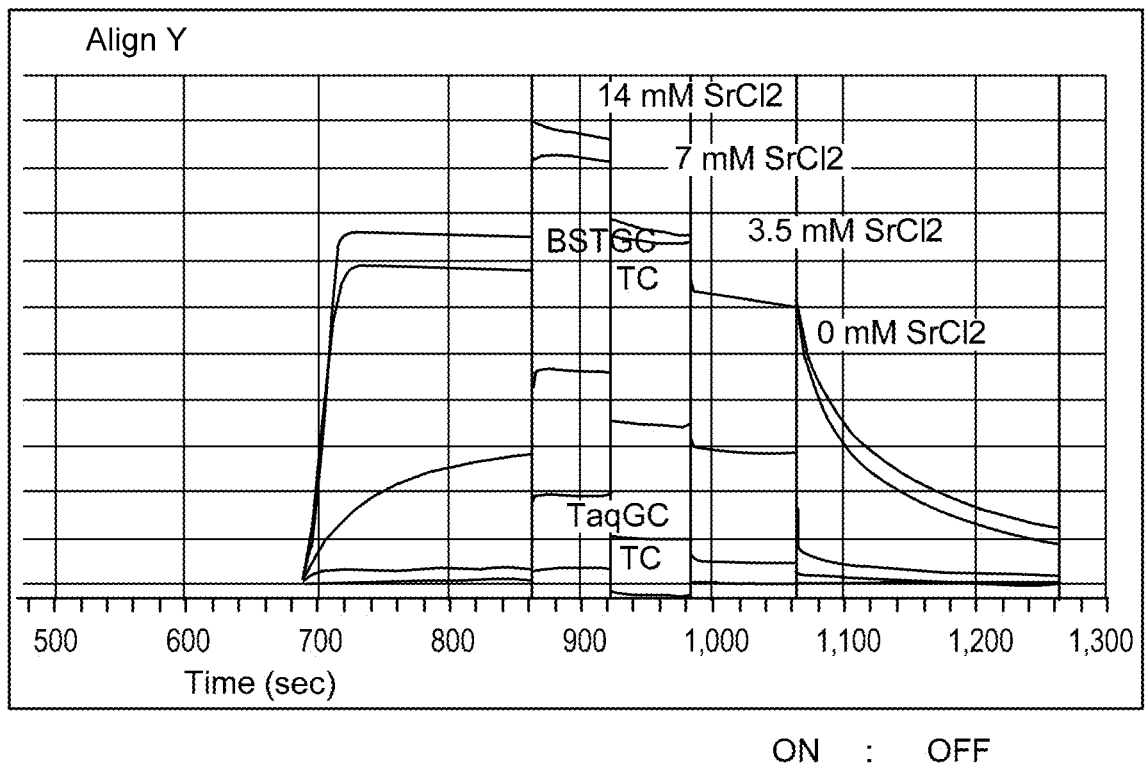
FIG. 5 is a graph showing the effect of washing on the stabilization of nucleic acid, polymerase complex using varying concentrations of $SrCl_2$ (0 mM-14 mM).

In order to minimize possibility of multiple additions in a homopolymer region, a wash step can be performed before incorporation. Metal cations such as calcium and strontium can stabilize the polymerase complex like magnesium but cannot support catalysis of the phosphodiester bond, which results in incorporation of the nucleotide. In this experiment, varying concentrations of $SrCl_2$ (0 mM-14 mM) were added to the wash buffer (LS buffer). The polymerase complex was much more stable in the presence of as little as 3.5 mM Sr (lowest concentration) in the wash buffer. Further, stability of the complex was not noticeably affected when correct or incorrect nucleotide was present during the binding step indicating that Sr related stability of the polymerase is not limited to ternary complexes. The results are shown in FIG. 5.

Example 7: Use of DNA Pol I without 3'-5' Exonuclease Activity

In this experiment, the effect of the 3'-5' exonuclease activity of DNA Pol I was investigated. Exonuclease activity increase fidelity as an incorrect base or flap is removed by the proofreading function provided by the exonuclease activity of the polymerase. However, this activity can potentially cleave correct bases leading to incorrect sequence reads. A primer with a 3' terminal mismatch was hybridized to template creating a frayed end or flap construct. Klenow exo- polymerase will not be able to extend this terminus. However, DNA pol I large fragment has exonuclease activity and could remove the mismatch base, once removed the primer can be extended normally by klenow exo- polymerase or DNA polymerase.

Experimental Conditions.

Two sensors with flap structures were exposed to either DNA polymerase or klenow exo- for sequencing. The sensors were then exposed to the template sequence in the correct order. The DNA polymerase sensor was able to add the bases whereas the klenow fragment sensor was unable to add any bases due to the flap structure. Any 3'-5' exo activity by DNA polymerase would cause base addition to be out of sync with the sequence.

Figure 6:
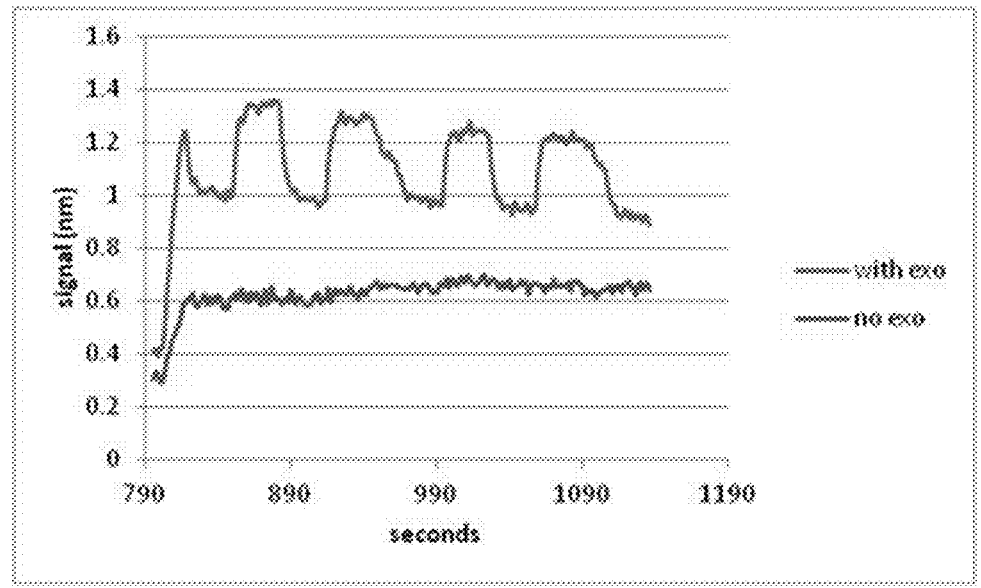
FIG. 6 is a graph showing the effect of 3'-5' exonuclease activity of DNA pol I on sequencing.

Results:

Cleavage of mismatch base by DNA polymerase allows subsequent base additions. Bases were correct out to 4 cycles. Without exonuclease activity, klenow exo(-) was unable to extend the template. The results are shown in FIG. 6. In cases where spurious exonuclease activity is detrimental, the exonuclease can be inhibited by competitive, uncompetitive or noncompetitive compounds or analogs. NaF is competitive inhibitor of DNA polymerase exonuclease function (Potapova et al., *FEBS Letters*, 277(1-2):109-111 (1990)).

| Nucleic acid sequences used in Examples 2-7 | | | |
|---|---|---|---|
| Name | len | 5' sequence 3' | Modification |
| phiX_matchC | 101 | GGC AAA TCA CCA GAA GGC GGT TCC TGA ATG AAT GGG AAG CCT TCA AGA AGG TGA TAA GCA GGA GAA ACA TAC GAA GGC GCA TAA CGA TAC CAC TGA CCC TC (SEQ ID NO: 3) | 5' biotin |
| phiX_matchA | 101 | GGC AAA TCA CCA GAA GGC GGT TCC TGA ATG AAT GGG AAG CCT TCA AGA AGG TGA TAA GCA GGA GAA ACA TAC GAA GCA TCA TAA CGA TAC CAC TGA CCC TC (SEQ ID NO: 4) | 5' biotin |
| FP2 | 22 | GAG GGT CAG TGG TAT CGT TAT G (SEQ ID NO: 5) | |
| PhiX_50matchA | 50 | TGA TAA GCA GGA GAA ACA TAC GAA GCA TCA TAA CGA TAC CAC TGA CCC TC (SEQ ID NO: 6) | 5' biotin |
| Alk_Btn-4460-4509S | 50 | GTGAGCCTGCAATCCCTGCCCCGGTTCATCCTGCTGGA GCTCATGGCGGG (SEQ ID NO: 7) | 5' biotin |
| ALK 4496-4509AS | 14 | CCCGCCATGAGCTC (SEQ ID NO: 8) | |

Example 8: Sequencing Using HIV Reverse Transcriptase (RT) and Non-Nucleoside Reverse Transcriptase Inhibitor (NNRTI) Compounds 7 and 18

EML4-ALK fusion is found in 4-5% of patients with non-small-cell lung cancer (Soda et al., Nature 448:561-6 (2007); Mano, Cancer Sci. 99:2349-55 (2008); and Horn and Pao, J. Clin. Oncol. 27:4232-5 (2009)). The ALK C4493A mutation has been identified in clinical lung tumors, which results in the L1196M "gatekeeper" mutation in ALK protein and confers resistance to the chemotherapy drug crizotinib (Choi et al., N. Engl. J. Med. 18:1734-9 (2010)). The 4496-4509AS primer enables sequencing into the region with the gatekeeper mutation. Template oligonucleotide sequence was derived from wild-type human ALK gene (nucleotide numbers 4460-4509). Primer sequence was complementary to human ALK gene (nucleotide numbers 4496-4509).

```
DNA sequence of template oligonucleotide Btn-4460-
4509S with 3' inverted dT:
                                       (SEQ ID NO: 9)
Biotin-5'-GTGAGCCTGCAATCCCTGCCCCGGTTCATCCTGCTGGAGC TCATGGCGGG-3'-(3'-dT-5')

DNA sequence of primer oligonucleotide 4496-
4509AS:
                                      (SEQ ID NO: 10)
5'-CCCGCCATGAGCTC-3'
```

Reagent Preparation.

Template oligonucleotide Btn-4460-45095 and primer oligonucleotide 4496-4509AS were synthesized and analyzed (liquid chromatography-mass spectrometry (LC-MS) and electrospray ionization (ESI)) by Integrated DNA Technologies (Coralville, Iowa). Oligonucleotides were prepared in TE Buffer (10 mM Tris pH 8.0, 0.1 mM EDTA) to 100 µM. Primer and template oligonucleotides were combined (10 µM each strand) in a tube containing Annealing Buffer (10 mM Tris pH 8.0, 0.1 mM EDTA, 80 mM KCl). The tube containing primer-template solution was loaded onto a dry heat block (95° C. for 5 min), and the block was transferred to the bench top to anneal the strands by gradual cooling to ambient temperature. Uncompetitive NNRTI compounds (Pitta et al., J. Enzyme Inhib. Med. Chem. 28(10):113-22 (2013)), which is incorporated by reference herein in its entirety), were from Epigen Biosciences, Inc. (San Diego, Calif.). NNRTI compounds 7 (3-4-chloro-benzo[d]thiazol-2yl)-2-(2-chloro-6-fluorophenyl)thiazolidin-4-one) and 18 (3-(6-ethoxy-benzo[d]thiazol-2-yl)-2-(2-chloro-6-fluoro-phenyl)thiazolidin-4-one) were dissolved in dimethylsulfoxide (DMSO) to concentrations of 25.0 mM and 15.0 mM, respectively. Recombinant purified HIV reverse transcriptase (HIV RT) was from Worthington Biochemical Corp (Lakewood, N.J.). Ultra-pure bovine serum albumin (BSA) was from Ambion (Foster City, Calif.). All reagents and solutions were molecular biology grade.

Experimental Conditions.

Primer-template duplex was diluted (100 µM) into Annealing Buffer. Immediately before use, HIV Reverse Transcriptase was pre-diluted into Enzyme Diluent (50 mM Tris, pH 8.0, 8 mM MgCl$_2$). Binding buffer (50 mM Tris, pH 8.0, 160 mM KCl, 0.5 mM EDTA, 11 mM MgCl$_2$, 0.3% (v/v) Triton X-100, 5.3 mM dithiothreitol (DTT), 100 µg/mL bovine serum albumin (BSA), 100 µM dNTP (dATP, dTTP, dGTP or dCTP), 100 nM HIV RT). NNRTI compounds were pre-diluted with DMSO immediately before being spiked into Binding Buffer. Reaction Buffer was Binding Buffer without NNRTI, dNTP or HIV RT enzyme. Buffer containing Primer-Template (PT), PT Wash Buffer, Binding buffer containing one dNTP, and Reaction Buffer were loaded (200 µL/well) into a Greiner 96-well black microplate (Sigma-Aldrich, St. Louis, Mo.; catalog number M9685). Streptavidin (SA) Biosensors (Pall ForteBio Corp., Menlo Park, Calif.; catalog number 18-5019) were re-hydrated in Annealing Buffer for approximately 10 minutes before use. The Octet QK biosensor system (Pall ForteBio Corp., Menlo Park, Calif.) was set for 30° C. operation and was programmed to coat the biosensors with Primer-Template and wash away unbound Primer-Template with PT Wash Buffer. Biosensors were transferred to Binding Buffer containing HIV RT+dCTP±NNRTI (association phase) followed by Reaction Buffer (dCTP incorporation and dissociation phase). Similarly, biosensors were transferred cyclically to solutions containing individual deoxyribonucleoside triphosphates (dATP, dGTP, dCTP or dTTP) as indicated. Cycles of binding and incorporation were repeated multiple times.

Data Analysis.

Data were imported into Microsoft Excel and Prism software (GraphPad Software, San Diego, Calif.) for display. The progress of binding and dissociation reactions was smoothed either by averaging within a 19.4-second window or by Prism software (19.4-second window and 6th-order smoothing polynomial).

Results.

Figure 7A:
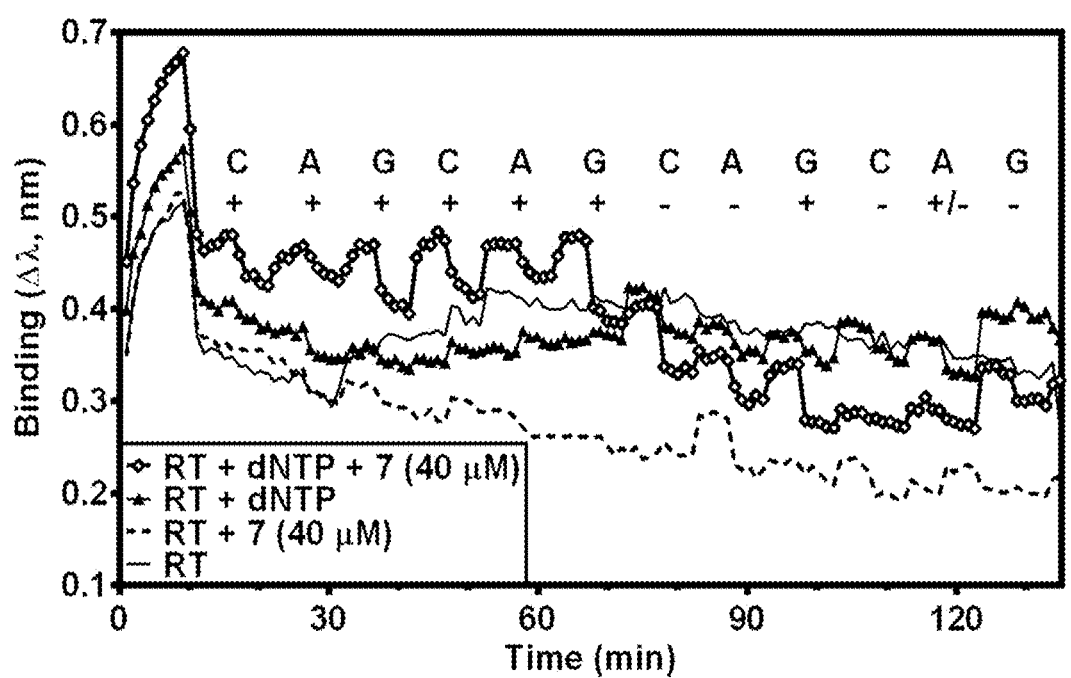
FIGS. 7A and 7B are graphs showing sequencing of human ALK gatekeeper region using HIV-1 reverse transcriptase, NNRTI compound 7 and the indicated dNTPs.
Figure 7B:
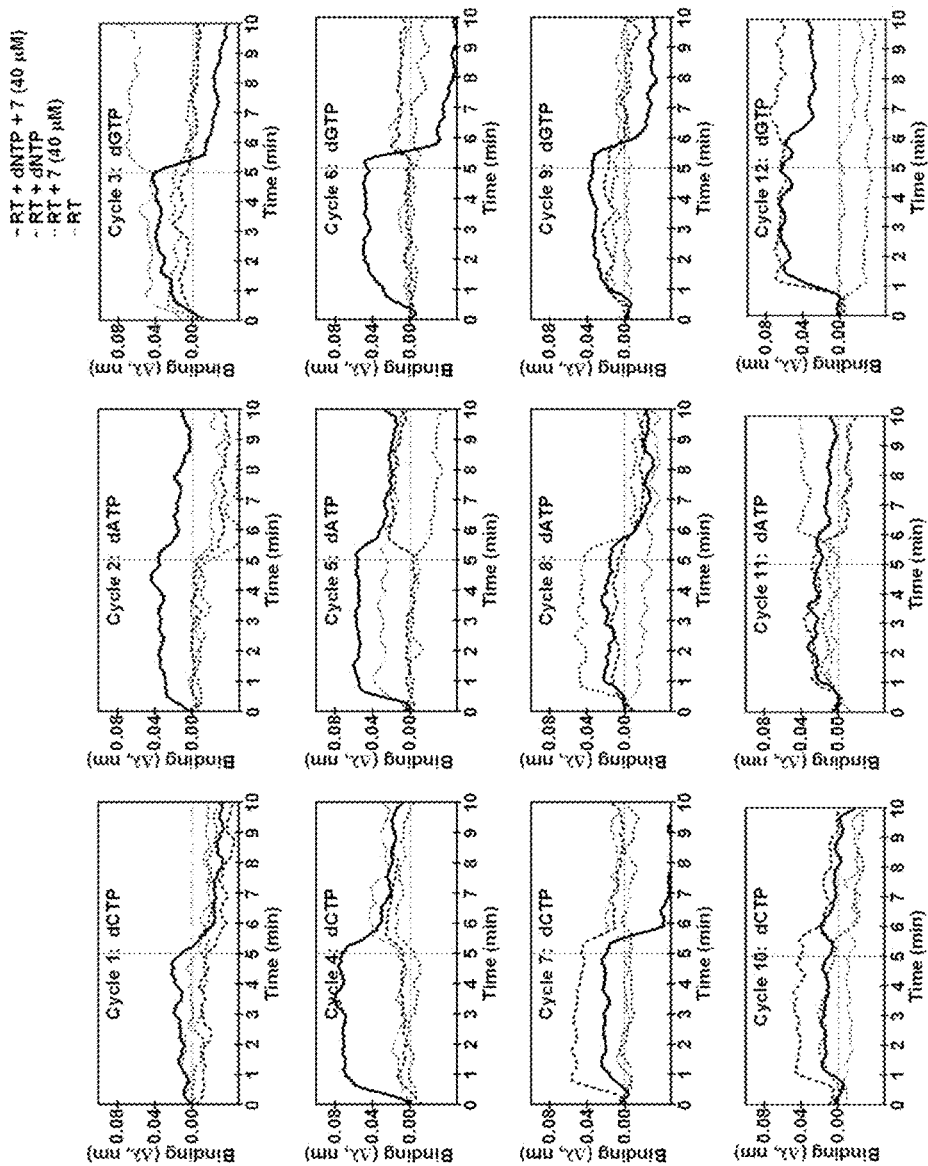

Non-nucleoside reverse transcriptase inhibitors (NNRTI) with reportedly an uncompetitive mode of inhibition were utilized for DNA sequencing via the DNA-dependent DNA polymerase activity of HIV reverse transcriptase. In assays for binding to biosensor coated with primer-template, the combination of HIV reverse transcriptase, correct dNTP and NNRTI compound 7 (40 µM) exhibit distinct peaks for binding in the association phase followed by decreased binding in wash buffer during the dissociation phase (FIG. 7A, circles). Unlike the NNRTI-stabilized HIV RT-dNTP mixtures, reactions containing HIV RT and correct dNTP did not produce appreciable binding peaks (FIG. 7A, triangles) nor did controls (HIV RT with or without 40 µM NNRTI compound 7; FIG. 7A, solid and dashed lines). The time course for binding and dissociation demonstrate sequencing for the first six cycles (nucleotide sequence CAGCAG) in FIG. 7A. The seventh cycle and eighth cycles with incorrect nucleotides dCTP and dATP, respectively did not produce a binding peak. The ninth cycle with the correct nucleotide dGTP (FIG. 7A). Time courses for binding (0-5 min) and dissociation (5-10 min) are shown for each cycle in FIG. 7B.

Figure 8:
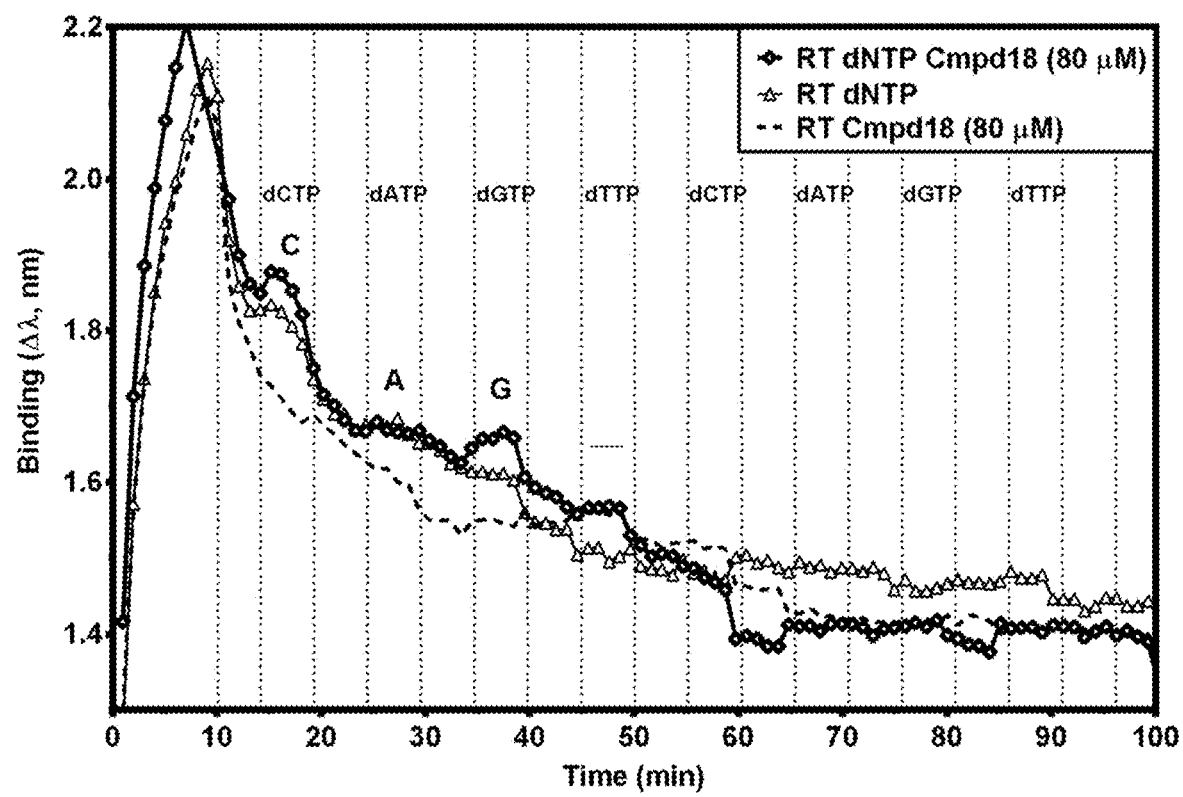
FIG. 8 is a graph showing sequencing of human ALK gatekeeper region using HIV-1 reverse transcriptase, NNRTI compound 18 and the various dNTPs.

Similarly, sequencing using HIV RT and NNRTI compound 18 also produced sequencing results. In assays for binding to biosensor coated with primer-template, the combination of HIV reverse transcriptase, correct dNTP and NNRTI compound 18 (80 µM) exhibit distinct peaks for binding in the association phase followed by decreased binding in wash buffer during the dissociation phase (FIG. 8, diamonds). Unlike the NNRTI-stabilized HIV RT-dNTP mixtures, reactions containing HIV RT and correct dNTP did not produce appreciable binding peaks (FIG. 8, triangles) nor did controls (HIV RT with 80 µM NNRTI compound 18; FIG. 8, dashed lines). In cycles 1-3, binding peaks indicated binding of HIV RT with correct nucleotide and compound 18 for sequence CAG (FIG. 8). Cycle 4 with HIV RT, incorrect nucleotide dTTP and compound 18 did not show a binding peak (FIG. 8). Subsequent cycles did not show further peaks for sequencing analysis. These results demonstrate the ability to use polymerase inhibitors during sequencing.

Example 9. DNA Sequencing on a Surface Plasmon Resonance (SPR) Imaging Biosensor Materials and Reagents.

SPR sensor chip: 20 mm×20 mm×1 mm high refractive index (1.61) slide (NanoSPR, Chicago, Ill.). Alkanethiols, PEG6: monothioalkane(C11)PEG6-OH(11-mercaptoundecyl hexaethyleneglycol (catalogue number, SPT-0011P6); and BAT: biotinylated alkane PEG thiol (catalogue number, SPT-0012D), were obtained from Sensopath technologies (Bozeman, Mont.). Base buffer (wash): 300 mM KCl, 20 mM Tris HCl (pH 8.0), 0.01% Tween-20, 1 mM SrCl2. Examination buffer: Base buffer plus 50 nM Klenow fragment+100 nM dNTP. Incorporation buffer: Base buffer plus 10 mM $MgCl_2$.

Prior to the experiment the Au coated SPR slide was coated with a mixed SAM of 18% BAT with 82% PEG6 diluted in 100% EtOH to final combined concentration of $1\times10^{-4}$ M. SPR slides were incubated in the alkanethiol solution overnight at room temperature. After incubation the SPR slides were rinsed in fresh 100% EtOH, followed by 50% EtOH in deionized water, and deionized water. The slides were then dried in air. The slides were mounted on a custom built SPR imaging system that provided fluidic control and image acquisition and data quantitation. A solution containing 10 µg/ml of Streptavidin in base buffer was injected into the flow cell. Binding of the resulting streptavidin layer was monitored by measuring the change in light reflected from the SPR chip for approximately 180 seconds, followed by washing with excess base buffer. Prehybridized primer FP2/PhiX_matchA template DNA was then injected into the flow cell and allowed to bind to the streptavidin layer for approximately 180 seconds, followed by washing with excess base buffer. For sequencing, solutions containing 50 nM Klenow fragment was prepared in base buffer with 100 nM of either dATP, dCTP, dTTP, or dGTP. The dNTP solutions were individually injected into the flow cell (in the order G, A, A, T, C, G), and allowed to incubate for approximately 180 seconds in order to examine the SPRi response. If there was no/low signal change, then flow cell was washed with excess base buffer. If the SPR signal indicated a base match, the flow cell was washed with incorporation buffer (containing 10 mM Mg2+) for 30 seconds to incorporate the correct dNTP, followed by wash with base buffer. The examination, incorporation, and wash steps were repeated.

Figure 9:
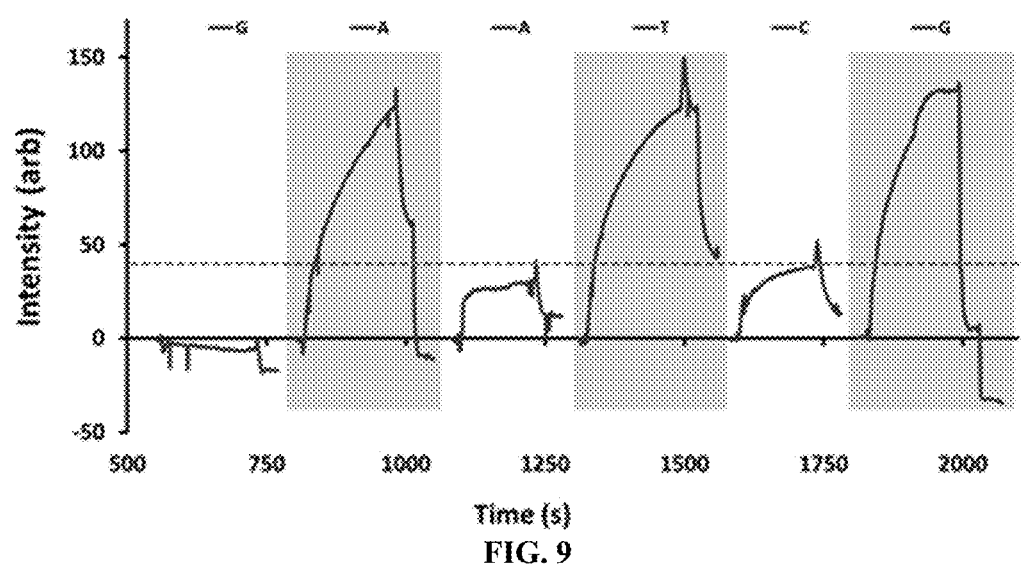
FIG. 9 is a sensorgram showing sequencing of the phiX_matchA template using a SPRi biosensor. Grayed areas correspond to correct base calls. The dotted line indicates the intensity change threshold used to determine binding of the correct Klenow/dNTP combination.

FIG. 9 shows the sensorgram recorded for the identification of three mismatched bases and three correct bases. The first three correct conjugate bases of the phiX_matchA template after the annealed primer sequence were A, T, and G. The first solution flowed over the sensor contained polymerase and dGTP, which corresponded to a base pair mismatch. The resulting sensor trace showed little change in baseline reflectance, indicating that the polymerase molecule did not bind to the primed template strand. The next solution flowed over the sensor contained polymerase and dATP, which corresponded to the correct conjugate base. The resulting trace (highlighted in the gray box), showed a strong increase in reflected light indicating that the polymerase had bound to the primed template strand, thereby shifting the position of the SPR. After allowing the polymerase solution to incubate for approximately 180 seconds (to ensure saturation of available binding sites), incorporation solution containing 10 mM Mg2+ was introduced into the flow cell. The introduction of Mg2+ allowed the polymerase to incorporate the bound dATP into the primer strand bound to the template. To ensure successful incorporation of dATP, the polymerase-dATP solution was again flowed over the sensor chip. This time, however, the amount of the reflected light did not increase as strongly as before indicating that the polymerase did not bind to the template strand as the correct cognate base was no longer A. To examine the next correct base, a solution of polymerase and dTTP was flowed over the sensor. Once again the intensity of reflected light increased above the threshold value indicating that the incorporation of dATP was successful and the next correct base was T, as expected. Incorporation buffer was flowed over the sensor chip to incorporate the base. The process was repeated two more time using a mismatch (polymerase-dCTP), followed by a match (polymerase-dGTP). In both cases the expected response was observed indicating that the next correct conjugate base was in fact G.

These results demonstrate the ability to accurately sequence DNA by Klenow/dNTP binding assay on a SPRi biosensor. The SPRi biosensor has sufficient sensitivity and durability to detect the different steps necessary for performing DNA sequencing over multiple examination/incorporation rounds. Herein is shown sequencing of three base pairs within a 60 bp strand. This technique can be extendable to an arbitrary number of sequencing cycles.

Example 10. Sequencing Double Stranded DNA by Nick Translation

```
DNA sequence of template oligonucleotide Btn-4460-
4509S with 3' inverted dT:
                                       (SEQ ID NO: 9)
Biotin-5'-GTGAGCCTGCAATCCCTGCCCCGGTTCATCCTGCTGGAGC TCATGGCGGG-3'-(3'-dT-5')

DNA sequence of primer oligonucleotide 4496-
4509AS:
                                      (SEQ ID NO: 10)
5'-CCCGCCATGAGCTC-3'

DNA sequence of oligonucleotide 4460-4494AS:
                                      (SEQ ID NO: 11)
5'-AGCAGGATGAACCGGG/i5NitInd/CAGGGATTGCAGGCTCAC-

3',
``` where "/i5NitInd/" is a 5-nitroindole-2'-deoxyribose residue. 5-Nitroindole is intended to prevent formation of guanine tetrads in this context and serves as a universal base.

Reagent Preparation.

Oligonucleotides were prepared in TE Buffer (10 mM Tris pH 8.0, 0.1 mM EDTA) to 100 µM. To prepare the ssDNA primer/template, oligonucleotides Btn-4460-4509S and 4496-4509AS were combined (10 µM each strand) in a tube containing Annealing Buffer (10 mM Tris pH 8.0, 0.1 mM EDTA, 80 mM KCl). To prepare the dsDNA primer/template with a 1-base pair gap, oligonucleotides Btn-4460-4509S, 4496-4509AS and 4460-4494AS were combined (10 µM each strand) in a tube containing Annealing Buffer. The tubes containing oligonucleotide solutions were loaded onto a dry heat block (95° C. for 5 min), and the block was transferred to the bench top to anneal strands by gradual cooling to ambient temperature. Full-length DNA polymerase encoded by *Bacillus stearothermophilus* ("Bst DNA polymerase", recombinant enzyme purified from *Escherichia coli*) was purchased from New England Biolabs (Ipswich, Mass.; catalog no. M0328L). Ultra-pure bovine serum albumin (BSA) was purchased from Ambion (Foster City, Calif.). All reagents and solutions were molecular biology grade.

Experimental Conditions.

Primer-template duplex was diluted (100 µM) into Annealing Buffer. Binding buffer was 50 mM Tris, pH 8.0, 300 mM KCl, 0.1% (v/v) Triton-X100, 100 µg/mL bovine serum albumin. Reaction Buffer was Binding Buffer containing 10 mM MgCl$_2$. Buffer containing Primer-Template (PT), Binding buffer containing one dNTP, and Reaction Buffer were loaded (200 µL/well) into a Greiner 96-well black microplate (Sigma-Aldrich, St. Louis, Mo.; catalog number M9685), and PCR-grade mineral oil (Sigma-Aldrich, St. Louis, Mo.; catalog no. M8662) was applied (75 µL/well). Streptavidin (SA) Biosensors (Pall ForteBio Corp., Menlo Park, Calif.; catalog number 18-5019) were re-hydrated in Annealing Buffer for approximately 10 minutes before use. The Octet QK biosensor system (Pall ForteBio Corp., Menlo Park, Calif.) was set for 30° C. operation and was programmed to coat the biosensors with Primer-Template and wash away unbound Primer-Template with Binding Buffer. Biosensors were transferred to Binding Buffer containing 136 Unit/mL Bst DNA Polymerase and 200 µM dNTP (dATP, dTTP, dGTP or dCTP) as indicated (association phase) followed by Reaction Buffer for dNTP incorporation. Biosensors were transferred to Reaction Buffer containing Bst DNA Polymerase (136 Unit/mL) without dNTP to promote nick translation via 5'-3' exonuclease activity. Biosensors were transferred to Reaction Buffer without enzyme or magnesium (dissociation phase). Similarly, biosensors were transferred cyclically to solutions containing individual deoxyribonucleoside triphosphates (dATP, dGTP, dCTP or dTTP) as indicated. Cycles of binding and incorporation and 5'-3' exonucleolytic cleavage were repeated multiple times to assess sequencing.

Data Analysis.

Data were imported into Microsoft Excel and Prism software (GraphPad Software, San Diego, Calif.) for display.

Results.

Figure 10A:
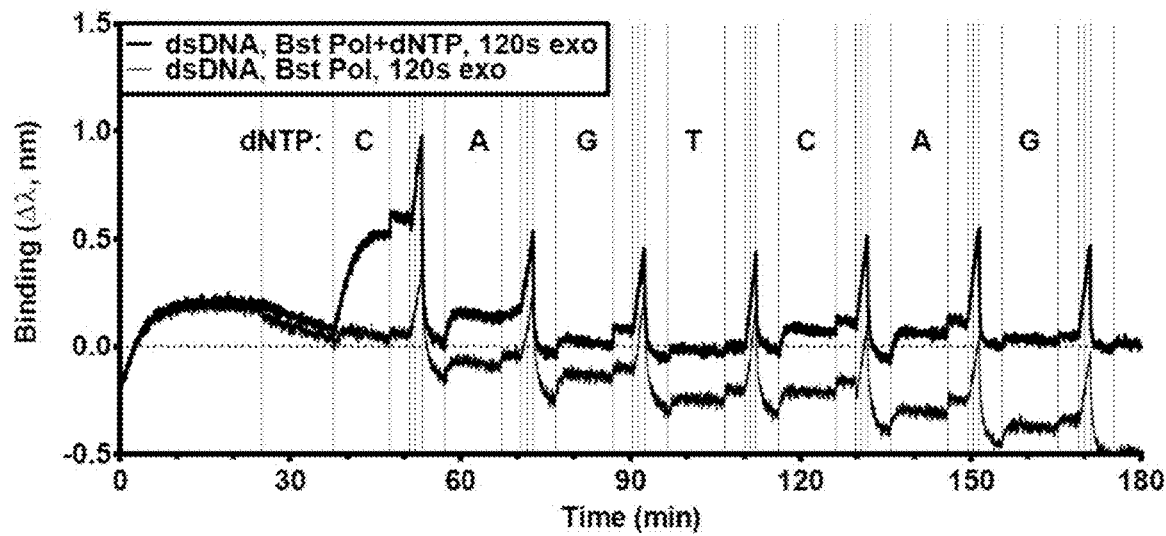
FIGS. 10A, 10B, and 10C are graphs showing sequencing of dsDNA by nick translation using Bst DNA Polymerase from *Bacillus stearothermophilus*. Double-stranded DNA with one base gap was treated with Bst DNA Pol with or without the indicated dNTP in Binding Buffer. Biosensors were transferred to Reaction Buffer for dNTP incorporation followed by transfer to Reaction Buffer containing Bst DNA Pol without dNTP for 5'-3' exonucleolytic cleavage of the non-template strand for 120 seconds (FIG. 10A) or 60 seconds (FIG. 10B). As a control, Bst DNA Pol was used for sequencing by binding a primed ssDNA template, dNTP incorporation followed by 5'-3' exonucleolytic processing for 60 seconds (FIG. 10C).
Figure 10B:
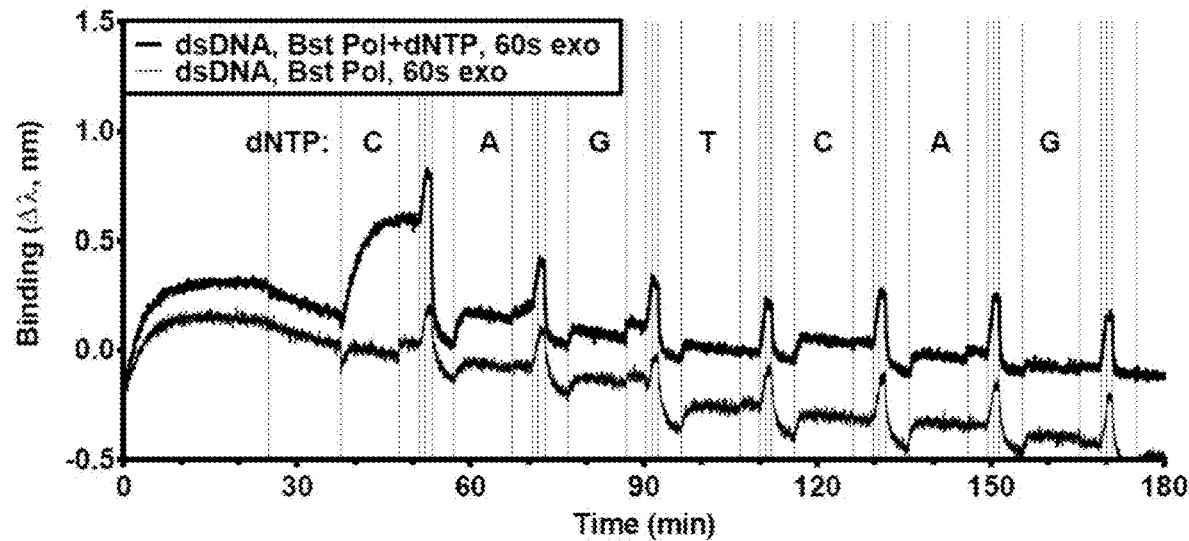
Figure 10C:
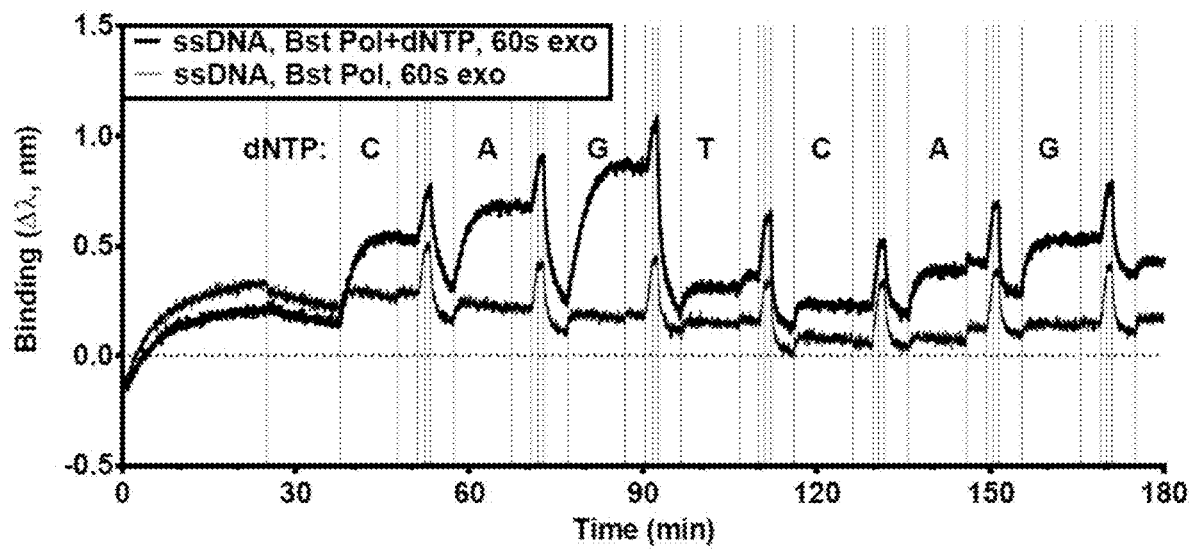

In assays for binding to biosensor coated with primer-template, the combination of Bst DNA polymerase and correct 2'-deoxyribonucleoside triphosphate (dCTP) exhibit distinct peak for binding in the association phase (FIGS. 10A, 10B, and 10C, dCTP "C"). Cycle 1 demonstrates binding and incorporation to the one base pair gap in the dsDNA template (FIGS. 10A and 10B) and incorporation of correct nucleotide downstream of the primer in the control ssDNA template (FIG. 10C). Controls lacking dNTP show minimal binding (FIGS. 10A, 10B, and 10C, cycles 1-7). Cycle 2 shows binding of polymerase to dsDNA template in combination with the next correct nucleotide, dATP (FIGS. 10A and 10B, dATP "A"), which is less than that of the unobstructed ssDNA template (FIG. 10C, dATP "A") indicates that the exonucleolytic cleavage of the complementary strand was not complete. The time course for binding and dissociation demonstrate sequencing for the first three cycles (nucleotide sequence CAG) of dsDNA (FIGS. 10A and 10B) and ssDNA (FIG. 10C). As expected the fourth cycle with the incorrect nucleotide dTTP did not produce a binding peak (FIGS. 10A, 10B, and 10C). These results demonstrate the ability to sequence double-stranded DNA by nick translation using the DNA polymerase and 5'-3' exonuclease activities of Bst DNA polymerase.

Example 11. Sequencing Double-Stranded DNA by Strand Displacement

```
DNA sequence of template oligonucleotide Btn-4460-
4509S with 3' inverted dT:
                                       (SEQ ID NO: 9)
Biotin-5'-GTGAGCCTGCAATCCCTGCCCCGGTTCATCCTGCTGGAGC TCATGGCGGG-3'-(3'-dT-5')

DNA sequence of primer oligonucleotide 4496-
4509AS:
                                      (SEQ ID NO: 10)
5'-CCCGCCATGAGCTC-3'

DNA sequence of oligonucleotide 4460-4494AS:
                                      (SEQ ID NO: 11)
5'-AGCAGGATGAACCGGG/i5NitInd/CAGGGATTGCAGGCTCAC-

3',
``` where "/i5NitInd/" is a 5-nitroindole-2'-deoxyribose residue. 5-Nitroindole is intended to prevent formation of guanine tetrads in this context and serves as a universal base.

```
DNA sequence of oligonucleotide 4460-4494AS-T8:
                                      (SEQ ID NO: 12)
5'-TTTTTTTTAGCAGGATGAACCGGG/i5NitInd/CAGGGATTGCAGG
CTCAC-3',
``` where "/i5NitInd/" is a 5-nitroindole-2'-deoxyribose residue. 5-Nitroindole is intended to prevent formation of guanine tetrads in this context and serves as a universal base.

Reagent Preparation.

Oligonucleotides Btn-4460-4509S, 4460-4494AS, 4496-4509AS and 4460-4494AS-T8 were synthesized and analyzed (liquid chromatography-mass spectrometry (LC-MS) and electrospray ionization (ESI)) by Integrated DNA Technologies (Coralville, Iowa). Oligonucleotides were prepared in TE Buffer (10 mM Tris pH 8.0, 0.1 mM EDTA) to 100 µM. To prepare the ssDNA primer/template, oligonucleotides Btn-4460-4509S and 4496-4509AS were combined (10 µM each strand) in a tube containing Annealing Buffer (10 mM Tris pH 8.0, 0.1 mM EDTA, 80 mM KCl). To prepare the dsDNA primer/template with a 1-base gap, oligonucleotides Btn-4460-4509S, 4496-4509AS and 4460-4494AS were combined (10 µM each strand) in a tube containing Annealing Buffer. To prepare the dsDNA primer/template with a 5'-oligo-dT flap and 1-base gap, oligonucleotides Btn-4460-4509S, 4496-4509AS and 4460-4494-AS-T8 were combined (10 µM each strand) in a tube containing Annealing Buffer. The tubes containing oligonucleotide solutions were loaded onto a dry heat block (95° C. for 5 min), and the block was transferred to the bench top to anneal strands by gradual cooling to ambient temperature. Klenow (3'→5' exo-) fragment of E. coli DNA polymerase was purchased from Enzymatics (Beverly, Mass.; catalog no. P7010-LC-L). Ultra-pure bovine serum albumin (BSA) was purchased from Ambion (Foster City, Calif.). All reagents and solutions were molecular biology grade.

Experimental Conditions.

Primer-template duplex was diluted (50 nM) into Annealing Buffer. Binding buffer was 20 mM Tris, pH 8.0, 300 mM KCl, 0.01% (v/v) Tween-20, 100 µg/mL bovine serum albumin, 1.0 mM dithiothreitol. Reaction Buffer was Binding Buffer containing 50 mM KCl and 10 mM $MgCl_2$. Buffer containing Primer-Template (PT), Binding buffer containing one dNTP, and Reaction Buffer were loaded (200 µL/well) into a Greiner 96-well black microplate (Sigma-Aldrich, St. Louis, Mo.; catalog number M9685), and PCR-grade mineral oil (Sigma-Aldrich, St. Louis, Mo.; catalog no. M8662) was applied (75 µL/well). Streptavidin (SA) Biosensors (Pall ForteBio Corp., Menlo Park, Calif.; catalog number 18-5019) were re-hydrated in Annealing Buffer for approximately 10 minutes before use. The Octet QK biosensor system (Pall ForteBio Corp., Menlo Park, Calif.) was set for 30° C. operation and was programmed to coat the biosensors with Primer-Template and wash away unbound Primer-Template with Binding Buffer. Biosensors were transferred to Binding Buffer containing Klenow exo- (68 Unit/mL) and 100 µM dNTP (dATP, dTTP, dGTP or dCTP) as indicated (association phase) followed by Reaction Buffer for dNTP incorporation. Biosensors were transferred to Reaction Buffer without enzyme or magnesium (dissociation phase). Similarly, biosensors were transferred cyclically to solutions containing individual deoxyribonucleoside triphosphates (dATP, dGTP, dCTP or dTTP) as indicated. Cycles of binding and incorporation were repeated multiple times to assess sequencing.

Data Analysis.

Data were imported into Microsoft Excel and Prism software (GraphPad Software, San Diego, Calif.) for display.

Results.

Figure 11A:
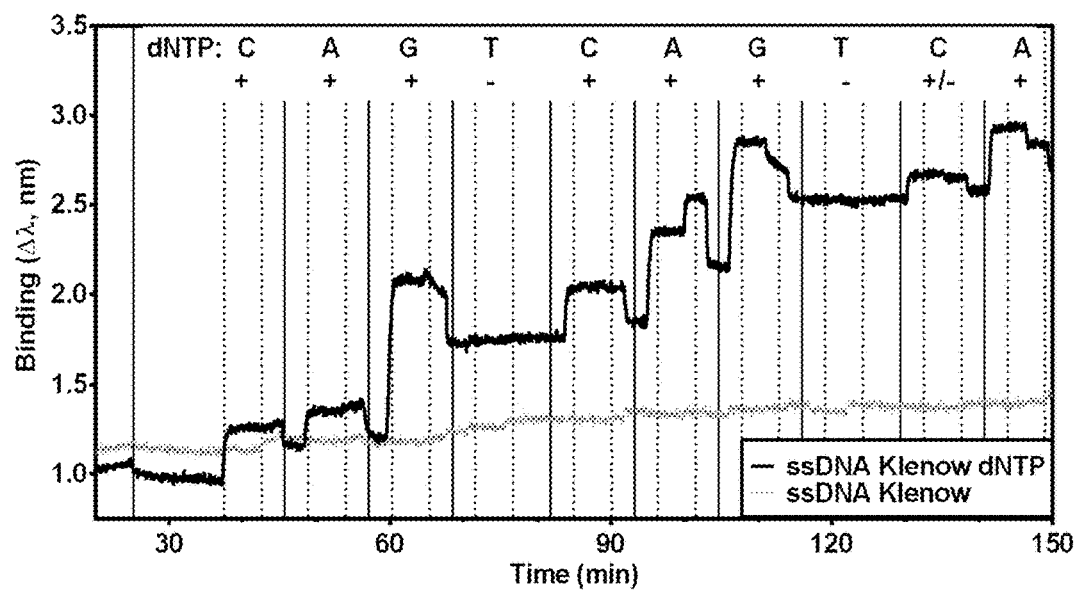
FIGS. 11A, 11B, and 11C are graphs showing sequencing of dsDNA with 5'-flap by strand displacement using Klenow (3'→5' exo-) fragment of *E. coli* DNA polymerase. DNA templates were treated with Klenow exo- DNA Pol with or without the indicated dNTP in Binding Buffer without $MgCl_2$. Biosensors were transferred to Wash Buffer with $MgCl_2$ for catalysis followed by re-equilibration in Binding Buffer without enzyme or dNTP. Cycles were repeated for each individual dNTP as indicated.
Figure 11B:
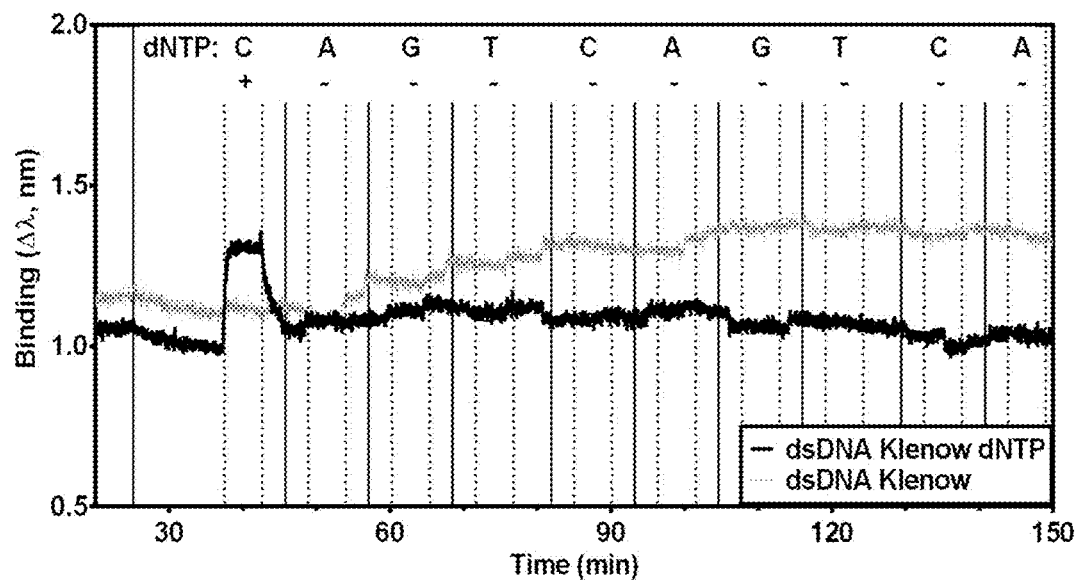
Figure 11C:
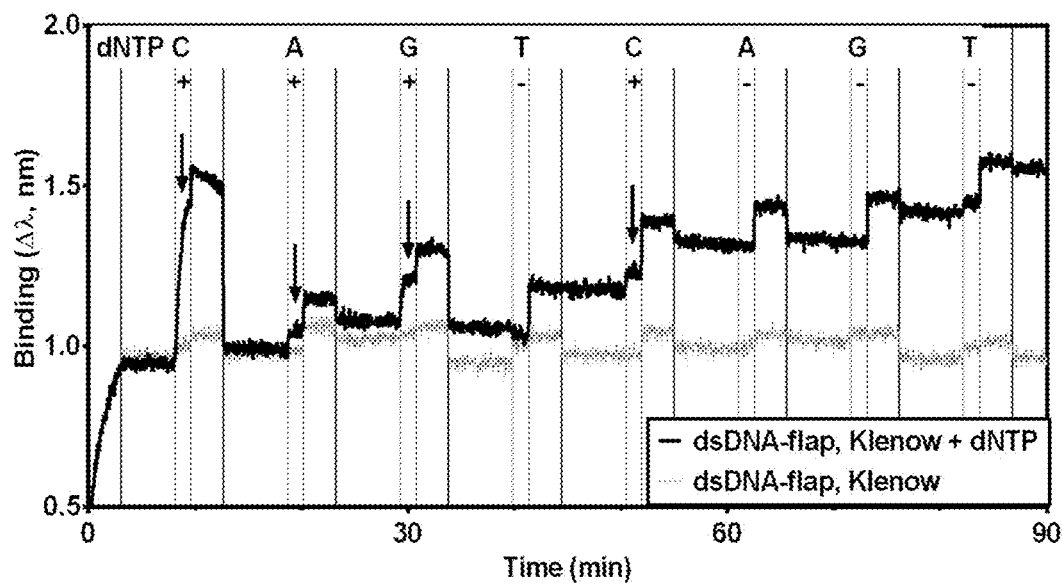

In assays for binding to biosensor coated with ssDNA primer-template, Klenow exo- yielded binding peaks in the presence of the correct individual dNTPs but not with the incorrect dTTP nucleotide (FIG. 11A, dark trace). By contrast, the negative control (enzyme without dNTP) failed to bind as shown by a consistently flat binding response (FIG. 11A, gray trace). Thus, Klenow exo- yielded a sequence of CAGCAG (C?)A (SEQ ID NO:13), which is 88% identical to the expected sequence (CAGCAGGA (SEQ ID NO:1)). In assays for binding to biosensor coated with dsDNA primer-template with a 1-base gap between the anti-sense primer and the downstream antisense strand, Klenow exo- yielded a binding peak only in the presence of the first correct individual dCTP nucleotide (FIG. 11B, dark trace). The negative control (enzyme without dNTP) failed to bind as shown by a consistently flat binding response (FIG. 11B, gray trace). Thus, Klenow exo- yielded a sequence of "C" in which the first base of the gap is filled with the correct nucleotide. However, in subsequent cycles further binding or polymerization into the double-stranded DNA region is blocked. Blockage of further sequencing is likely due to the inherent lack of the 5'-3' exonuclease domain of Klenow exo- (for nick translation) or to inability to disrupt the downstream double-stranded helix of DNA (strand displacement). Therefore, a 5'-oligo-dT flap was introduced to provide a better substrate to Klenow exo- for strand displacement. Biosensors were coated with dsDNA primer-template bearing a 5'-oligo-dT flap with a 1-base gap between the anti-sense primer and the downstream antisense strand. Klenow exo- yielded binding peaks in the 1-base gap (C) of cycle #1, and additional binding peaks were observed into the dsDNA region providing the sequence AGC for cycle #2, 3 and 5 (FIG. 11C, dark trace). Cycles #4, 6, 7 and 8 with the incorrect dNTP did not afford binding of enzyme to the immobilized DNA (FIG. 11C). The negative control (enzyme without dNTP) failed to bind as shown by a flat binding response (FIG. 11C, gray trace). Thus, Klenow exo- yielded a 100% correct sequence of "CAGC" in which the first base of the gap was filled with the correct nucleotide, and further binding or polymerization was observed for three additional bases into the double-stranded DNA region. The 5'-flap adjacent to the double-stranded DNA region enabled Klenow exo- to sequence by strand displacement (FIG. 11C), whereas lack of the 5'-flap blocked sequencing into the dsDNA region (FIG. 11B). These results demonstrate the ability to sequence double-stranded DNA using Klenow exo- fragment of DNA polymerase by a strand displacement mechanism.

Example 12. Effect of Anions on Single Stranded DNA Sequencing

To prepare the ssDNA primer/template, oligonucleotides Btn-4460-4509S (SEQ ID NO:9) and 4496-4509AS (SEQ ID NO:10) were combined (10 µM each strand) in a tube containing Annealing Buffer (10 mM Tris pH 8.0, 0.1 mM EDTA, 80 mM KCl). Tubes containing oligonucleotide solutions were loaded onto a dry heat block (95° C. for 5 min), and the block was transferred to the bench top to anneal strands by gradual cooling to ambient temperature. Klenow (3'→5' exo- fragment of *E. coli* DNA polymerase was purchased from Enzymatics (Beverly, Mass.; catalog no. P7010-LC-L). Potassium glutamate was purchased from (Teknova, Hollister, Calif.; catalog no. P2000). Ultra-pure bovine serum albumin (BSA) was purchased from Ambion (Foster City, Calif.). All reagents and solutions were molecular biology grade.

Experimental Conditions.

Binding buffer was 20 mM Tris, pH 8.0, 300 mM KCl, 0.01% (v/v) Tween-20, 100 µg/mL bovine serum albumin, 1.0 mM dithiothreitol. Reaction Buffer was Binding Buffer containing 50 mM KCl and 10 mM MgCl$_2$. For each level of potassium glutamate tested, the Binding Buffers were prepared to contain 0, 50, 100 or 200 mM potassium glutamate. Reaction Buffers did not contain potassium glutamate. The Octet QK biosensor system was set up as described in Example 11 Biosensors were transferred to Binding Buffer containing Klenow exo- (68 Unit/mL) and 100 µM dNTP (dATP, dTTP, dGTP or dCTP) as indicated (association phase) followed by Reaction Buffer for dNTP incorporation. Biosensors were transferred to Reaction Buffer containing magnesium without enzyme (dissociation phase). Biosensors were transferred to Binding Buffers without enzyme or dNTP but containing the respective concentrations of potassium glutamate to re-equilibrate. Similarly, biosensors were transferred cyclically to solutions containing individual deoxyribonucleoside triphosphates (dATP, dGTP, dCTP or dTTP) as indicated. Cycles of binding and incorporation were repeated multiple times to assess sequencing.

Data Analysis.

Data were imported into Microsoft Excel and Prism software (GraphPad Software, San Diego, Calif.) for display.

Results.

Figure 12A:
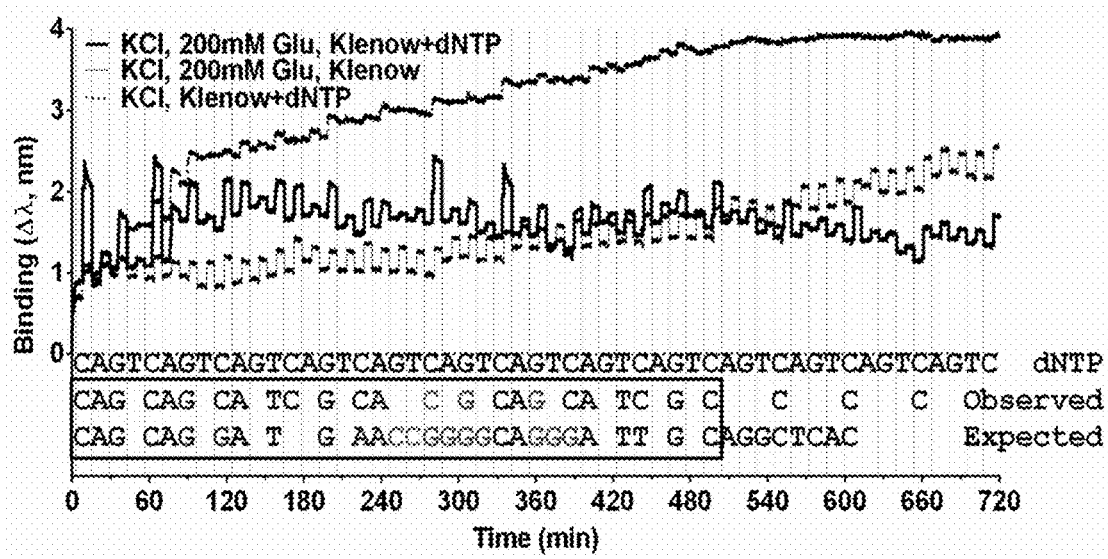
FIGS. 12A, 12B, and 12C are graphs showing sequencing ssDNA by Klenow exo-) fragment of *E. coli* DNA polymerase are promoted by salt components. Binding Buffers contain 200 mM glutamate (FIG. 12A), 100 mM glutamate (FIG. 12B) and 50 mM glutamate (FIG. 12C). Reaction Buffers contain $MgCl_2$ without glutamate. The applied dNTP for each cycle ("dNTP") is shown in the top text row (SEQ ID NO:14) of each of FIGS. 12A, 12B, and 12C. Binding of Klenow (exo-) indicates observed sequence ("Observed") in the second row of FIGS. 12A (SEQ ID NO:15), 12B (SEQ ID NO:17), and 12C (SEQ ID NO:19). "Expected" sequence based on the template is shown in the third text row of FIGS. 12A (SEQ ID NO:16), 12B (SEQ ID NO:18), and 12C (SEQ ID NO:20).
Figure 12B:
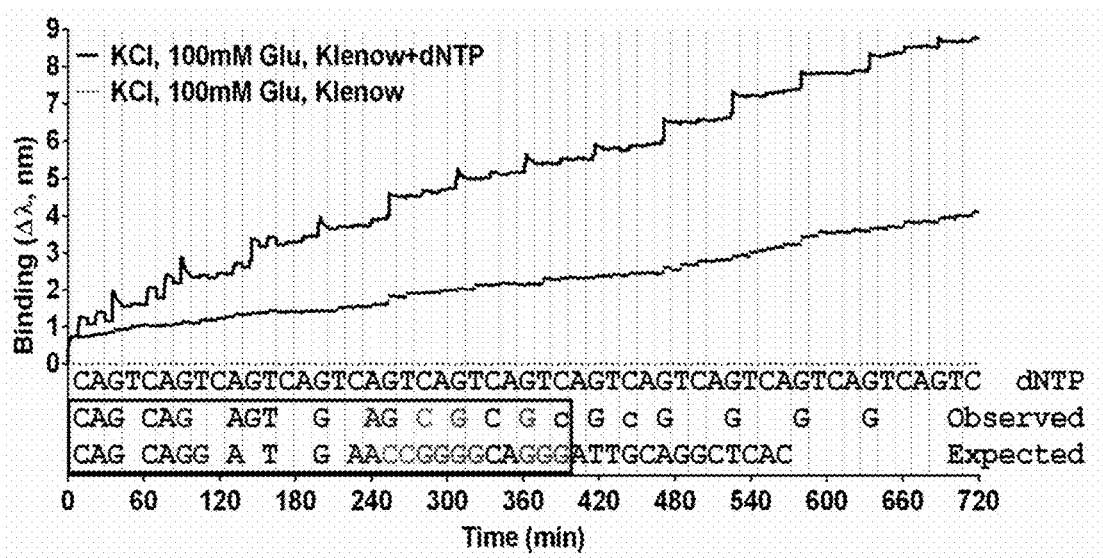
Figure 12C:
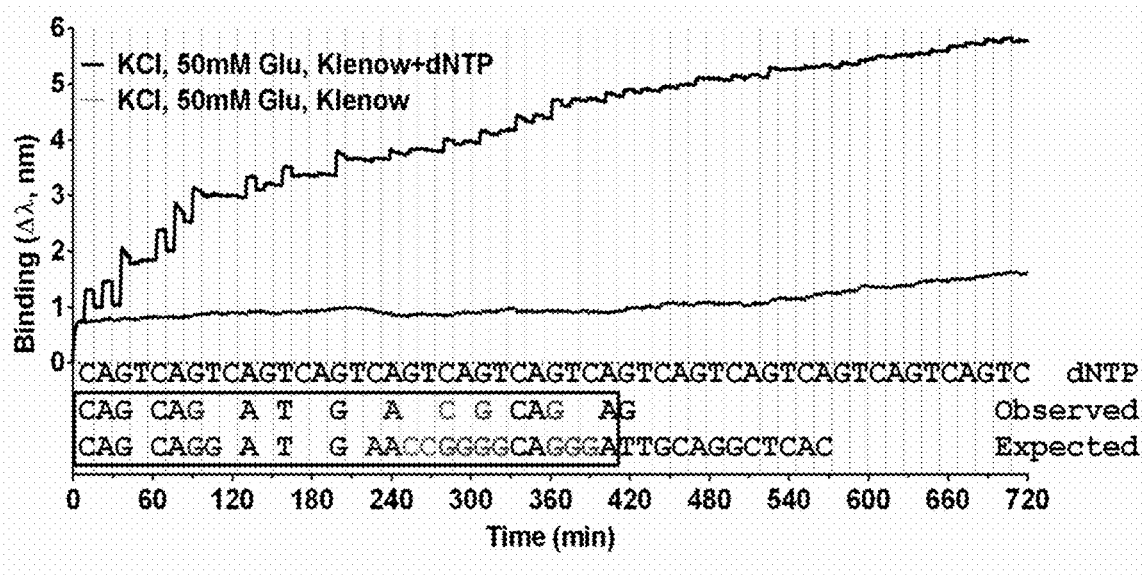

In assays for binding to biosensor coated with ssDNA primer-template, Klenow exo- (KCl without glutamate) yielded binding peaks for sequencing using the correct nucleotides as did enzyme in KCl containing 200 mM glutamate (FIG. 12A, dotted line and solid line, respectively). However, buffers without glutamate exhibited decreased amplitude of binding peaks combined with increasing background compared to formulations with 200 mM glutamate (FIG. 12A). Correct sequence was observed in KCl+200 mM glutamate formulations according to the relative peak heights for mixtures containing enzyme and correct dNTP (but not incorrect dNTP) over a 8.25-hour time course (FIG. 12A). Homopolymer runs appear to be detected as a single peak under these conditions. (FIGS. 12A, 12B, and 12C). In buffers containing KCl+100 mM glutamate, correct sequences were observed with strong peak signal for enzyme+correct dNTP over the course of 7 hours, whereas the control (enzyme without dNTP) produced no peaks and a gradual increase in background (FIG. 12B). Buffers containing KCl+50 mM glutamate show correct sequences over the course of 7 hours, whereas the control enzyme without dNTP yielded no binding peaks and a flat, stable background (FIG. 12C). These results demonstrate the ability to sequence single-stranded DNA using Klenow exo- fragment of DNA polymerase with enhancement by potassium glutamate and protection from evaporation by mineral oil overlay.

Example 13. Detecting a Point Mutation in a Wild-Type Background by Sequencing Single-Stranded DNA and Double-Stranded 5'-Flap DNA

```
DNA sequence of template oligonucleotide Btn-4460-
4509S with 3' inverted dT:
                                            (SEQ ID NO: 9)
Biotin-5'-GTGAGCCTGCAATCCCTGCCCCGGTTCATCCTGCTGGAGC TCATGGCGGG-3'-(3'-dT-5')

DNA sequence of template oligonucleotide Btn-4460-
4509S C4493A with 3' inverted dT:
                                           (SEQ ID NO: 21)
Biotin-5'-GTGAGCCTGCAATCCCTGCCCCGGTTCATCCTGATGGAGC TCATGGCGGG-3'-(3'-dT-5')

DNA sequence of primer oligonucleotide 4496-
4509AS:
                                           (SEQ ID NO: 10)
5'-CCCGCCATGAGCTC-3'

DNA sequence of oligonucleotide 4460-4494AS-T8:
                                           (SEQ ID NO: 12)
5'-TTTTTTTTAGCAGGATGAACCGGG/i5NitInd/CAGGGATTGCAGG

CTCAC-3',
``` where "/i5NitInd/" is a 5-nitroindole-2'-deoxyribose residue. 5-Nitroindole is intended to prevent formation of guanine tetrads in this context and serves as a universal base.

Reagent Preparation.

Oligonucleotides Btn-4460-4509S, Btn-4460-4509S C4493A, 4496-4509AS and 4460-4494AS-T8 were synthesized and analyzed (liquid chromatography-mass spectrometry (LC-MS) and electrospray ionization (ESI)) by Integrated DNA Technologies (Coralville, Iowa). Oligonucleotides were prepared in TE Buffer (10 mM Tris pH 8.0, 0.1 mM EDTA) to 100 µM. To prepare the ssDNA primer/template, oligonucleotides Btn-4460-4509S (or C4493A) and 4496-4509AS were combined (10 µM each strand) in a tube containing Annealing Buffer (10 mM Tris pH 8.0, 0.1 mM EDTA, 80 mM KCl). To prepare the dsDNA primer/template with a 5'-oligo-dT flap and 1-base gap, oligonucleotides Btn-4460-4509S (or C4493A), 4496-4509AS and 4460-4494-AS-T8 were combined (10 µM each strand) in a tube containing Annealing Buffer. The tubes containing oligonucleotide solutions were loaded onto a dry heat block (95° C. for 5 min), and the block was transferred to the bench top to anneal strands by gradual cooling to ambient temperature. Klenow (3'→5' exo-) fragment of *E. coli* DNA polymerase was purchased from Enzymatics (Beverly, Mass.; catalog no. P7010-LC-L). Ultra-pure bovine serum albumin (BSA) and UltraPure Salmon Sperm DNA Solution were purchased from Life Technologies (Foster City, Calif.). Nickel(II) sulfate hexahydrate (catalog no. 467901), dCDP, dGDP and dTDP were purchased from Sigma (St. Louis, Mo.). All reagents and solutions were molecular biology grade.

Experimental Conditions.

Primer-template duplex was diluted (50 nM) into Annealing Buffer. Wash buffer was 20 mM Tris, pH 8.0, 200 mM KCl, 200 mM potassium glutamate, 0.01% (v/v), Tween-20, 100 µg/mL bovine serum albumin, 1.0 mM dithiothreitol.

Binding Buffer was Wash Buffer containing 2.0 mM Ni(II) SO$_4$. Reaction Buffer was 20 mM Tris, pH 8.0, 50 mM KCl, MgCl$_2$ (10 mM), 0.01% (v/v) Tween-20, 100 µg/mL bovine serum albumin, 1.0 mM dithiothreitol. EDTA Wash Buffer was Binding Buffer containing 100 µM EDTA. Buffer containing Primer-Template (PT), Binding buffer containing one dNTP and Reaction Buffer were loaded (200 µL/well) into a Greiner 96-well black microplate (Sigma-Aldrich, St. Louis, Mo.; catalog number M9685), and PCR-grade mineral oil (Sigma-Aldrich, St. Louis, Mo.; catalog no. M8662) was applied (75 µL/well). High-precision streptavidin biosensors (Pall ForteBio Corp., Menlo Park, Calif.; catalog number 18-5117) were re-hydrated in Annealing Buffer for approximately 10 minutes before use. The Octet QK biosensor system (Pall ForteBio Corp., Menlo Park, Calif.) was set for 30° C. operation and was programmed to coat the biosensors with Primer-Template and wash away unbound Primer-Template with Wash Buffer. Biosensors were transferred to Binding Buffer containing Klenow exo- (68 Unit/mL), Ni(II)SO$_4$ (1.5 mM) and 100 µM dNTP (dATP, dTTP, dGTP or dCTP) as indicated (association phase) followed by dNTP incorporation (dissociation phase) in Reaction Buffer containing MgCl$_2$ (10 mM). Biosensors were transferred to EDTA Wash Buffer followed by re-equilibration in Reaction Buffer without enzyme, nucleotide or divalent cation. Similarly, biosensors were transferred cyclically to solutions containing individual deoxyribonucleoside triphosphates (dATP, dGTP, dCTP or dTTP) as indicated. Cycles of binding and incorporation were repeated for each dNTP to assess sequencing.

Data Analysis.

Data were imported into Microsoft Excel and Prism software (GraphPad Software, San Diego, Calif.) for display.

Results.

Figure 13A:
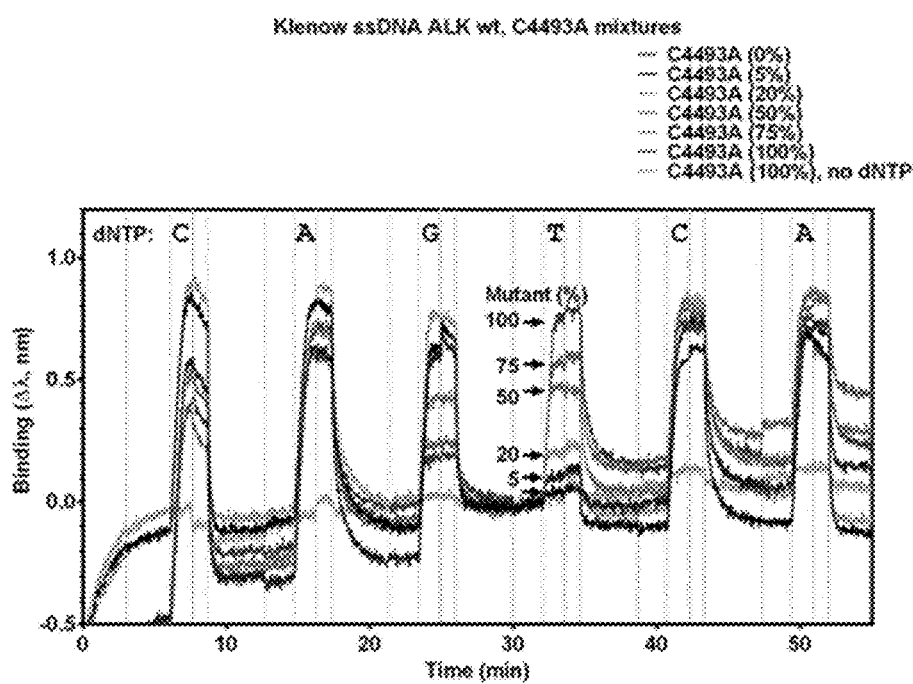
FIGS. 13A, 13B, and 13C are graphs of sequencing the sense strand of human ALK C4493A mutant in a background of ALK wild-type by Klenow exo- DNA polymerase.

In assays for binding to biosensor coated with ssDNA primer-template, Klenow exo- enzyme bound strongly to the biosensor in the presence of correct dNTP in cycles 1-2 (FIG. 13A). The "G" peak in cycle 3 shows increasing peak height in mixtures containing increasing concentrations of ALK wild-type template (FIG. 13A). The "T" peak in cycle 4 shows increasing peak heights in mixtures containing increasing concentrations of ALK C4493A mutation. The "T" readout at cycle 4 corresponds to the antisense nucleotide of the C4493A mutant. Both ALK wild-type and C4493A templates produce full-height peaks of "C" and "A" in cycles 5 and 6. Peaks indicate correct sequences for ALK wild-type (CAGCA) and ALK C4493A (CATCA) in FIG. 13A.

Figure 13B:
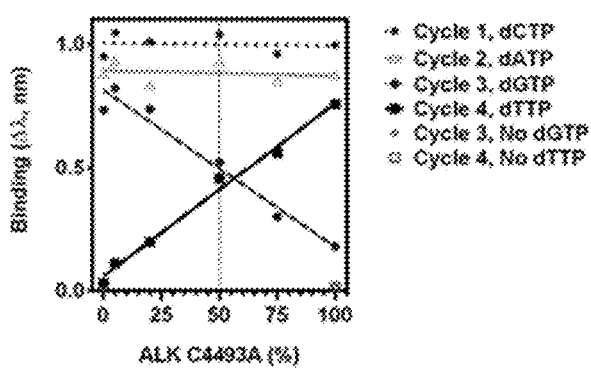
Figure 13C:
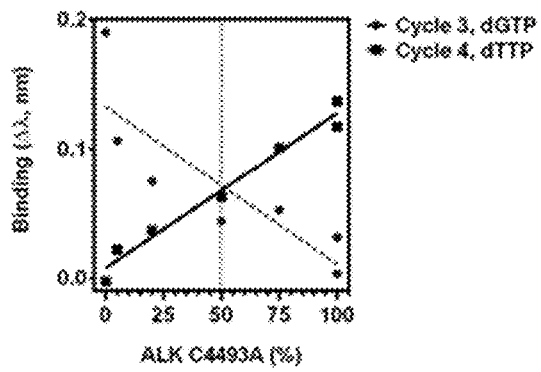

Peak intensities during sequencing allow quantitation of mutant allele in mixtures with wild-type sequence. The intensity of cycle 4 peak (T) was proportional to the quantity of ALK C4493A mutant sequence in the ALK wild-type background for ssDNA (FIG. 13B) and dsDNA-flap (FIG. 13C). Similarly, the cycle 3 peak (G) decreased linearly with increasing mutant concentration in the ssDNA template (FIG. 13B), and peak 3 intensity decreased with mutant concentration for the dsDNA-flap template (FIG. 13C). In a wild-type background, as little as 5% of a mutant sequence could be detected in either ssDNA or dsDNA-flap templates. These results demonstrate the ability to detect small quantities of mutant sequence in the presence of similar DNA sequences using ssDNA or dsDNA templates.

Example 14. Effect of Divalent Cations on Stabilizing the Ternary Complex and Polymerase Catalysis DNA sequence of template oligonucleotide Btn-4460-4509S C4493A with 3' inverted dT:
(SEQ ID NO: 21)
Biotin-5'-GTGAGCCTGCAATCCCTGCCCCGGTTCATCCTGATGGAGC TCATGGCGGG-3'-(3'-dT-5')

DNA sequence of primer oligonucleotide 4496-4509AS:
(SEQ ID NO: 10)
5'-CCCGCCATGAGCTC-3'

Reagent Preparation.

Oligonucleotides Btn-4460-4509S C4493A and 4496-4509AS were synthesized and analyzed (liquid chromatography-mass spectrometry (LC-MS) and electrospray ionization (ESI)) by Integrated DNA Technologies (Coralville, Iowa). Oligonucleotides were prepared in TE Buffer (10 mM Tris pH 8.0, 0.1 mM EDTA) to 100 µM. To prepare the ssDNA primer/template, oligonucleotides Btn-4460-4509S C4493A and 4496-4509AS were combined (10 µM each strand) in a tube containing Annealing Buffer (10 mM Tris pH 8.0, 0.1 mM EDTA, 80 mM KCl). The tubes containing oligonucleotide solutions were loaded onto a dry heat block (95° C. for 5 min), and the block was transferred to the bench top to anneal strands by gradual cooling to ambient temperature. Klenow (3'→5' exo-) fragment of E. coli DNA polymerase was purchased from Enzymatics (Beverly, Mass.; catalog no. P7010-LC-L). Ultra-pure bovine serum albumin (BSA) and UltraPure Salmon Sperm DNA Solution were purchased from Life Technologies (Foster City, Calif.). Strontium chloride, calcium chloride, manganese chloride, barium chloride, cobalt chloride, zinc chloride, copper(II) chloride, ferrous ammonium sulfate, ammonium sulfate, nickel(II) sulfate hexahydrate, dCDP, dGDP and dTDP were purchased from Sigma (St. Louis, Mo.). All reagents and solutions were molecular biology grade.

Experimental Conditions.

Primer-template duplex was diluted (100 nM) into Annealing Buffer. Wash buffer was 20 mM Tris, pH 8.0, 50 mM KCl, 0.01% (v/v) Tween-20, 100 µg/mL bovine serum albumin, 1.0 mM dithiothreitol. Binding Buffer was 20 mM Tris, pH 8.0, 200 mM KCl, 200 mM potassium glutamate, 0.01% (v/v) Tween-20, 100 µg/mL bovine serum albumin, 1.0 mM dithiothreitol. Reaction Buffer was 20 mM Tris, pH 8.0, 50 mM KCl, 0.01% (v/v) Tween-20, 100 µg/mL bovine serum albumin, 1.0 mM dithiothreitol and the indicated divalent cation. EDTA Wash Buffer was Binding Buffer containing 100 µM EDTA. Buffer containing Primer-Template (PT), Binding buffer containing one dNTP and Reaction Buffer were loaded (200 µL/well) into a Greiner 96-well black microplate (Sigma-Aldrich, St. Louis, Mo.; catalog number M9685), and PCR-grade mineral oil (Sigma-Aldrich, St. Louis, Mo.; catalog no. M8662) was applied (75 µL/well). High-precision streptavidin biosensors (Pall ForteBio Corp., Menlo Park, Calif.; catalog number 18-5117) were re-hydrated in Annealing Buffer for approximately 10 minutes before use. The Octet QK biosensor system (Pall ForteBio Corp., Menlo Park, Calif.) was set for 30° C. operation and was programmed to coat the biosensors with Primer-Template and wash away unbound Primer-Template with Wash Buffer.

To measure the initial level of unincorporated primer/template, biosensors were transferred to Binding Buffer containing Klenow exo- (68 Unit/mL), $SrCl_2$ (2.0 mM) and 100 μM dCTP (association phase) followed by Wash Buffer containing $SrCl_2$ (2.0 mM) and salmon sperm DNA trap (500 μg/mL) without $MgCl_2$. Sensors were transferred to Wash Buffer containing and salmon sperm DNA trap (500 μg/mL) without $MgCl_2$, followed by EDTA Wash Buffer and re-equilibration in Binding Buffer.

Binding to unincorporated primer/template was measured and stability of the ternary complex in divalent cation-free Binding Buffer was monitored. Biosensors were transferred to Binding Buffer containing Klenow exo- (68 Unit/mL), either $CoCl_2$ (1.0 mM) or the indicated divalent cation (2.0 mM), and 100 μM dCTP (association phase) followed by Wash Buffer containing the same concentration of the same divalent cation and salmon sperm DNA trap (500 μg/mL) without $MgCl_2$. Sensors were transferred to Wash Buffer containing and salmon sperm DNA trap (500 μg/mL) without $MgCl_2$, followed by EDTA Wash Buffer and re-equilibration in Binding Buffer.

Stabilization of the ternary complex in Binding Buffers containing various divalent cations without dNTP was measured. Biosensors were transferred to Binding Buffer containing Klenow exo- (68 Unit/mL), either $CoCl_2$ (1.0 mM) or the indicated divalent cation (2.0 mM), and 100 μM dCTP (association phase) followed by Wash Buffer containing the same divalent cation and salmon sperm DNA trap (500 μg/mL) without $MgCl_2$. Sensors were transferred to Wash Buffer containing and salmon sperm DNA trap (500 μg/mL) with 10 mM $MgCl_2$, followed by EDTA Wash Buffer and re-equilibration in Binding Buffer.

Finally nucleotide incorporation was determined by measuring the remaining unincorporated primer/template. Biosensors were transferred to Binding Buffer containing Klenow exo- (68 Unit/mL), $SrCl_2$ (2.0 mM) and 100 μM dCTP (association phase) followed by Wash Buffer containing $SrCl_2$ (2.0 mM) and salmon sperm DNA trap (500 μg/mL) without $MgCl_2$. Sensors were transferred to Wash Buffer containing and salmon sperm DNA trap (500 μg/mL) without $MgCl_2$, followed by EDTA Wash Buffer and re-equilibration in Binding Buffer.

Data Analysis.

Data were imported into Microsoft Excel and Prism software (GraphPad Software, San Diego, Calif.) for display.

Results.

Figure 14A:
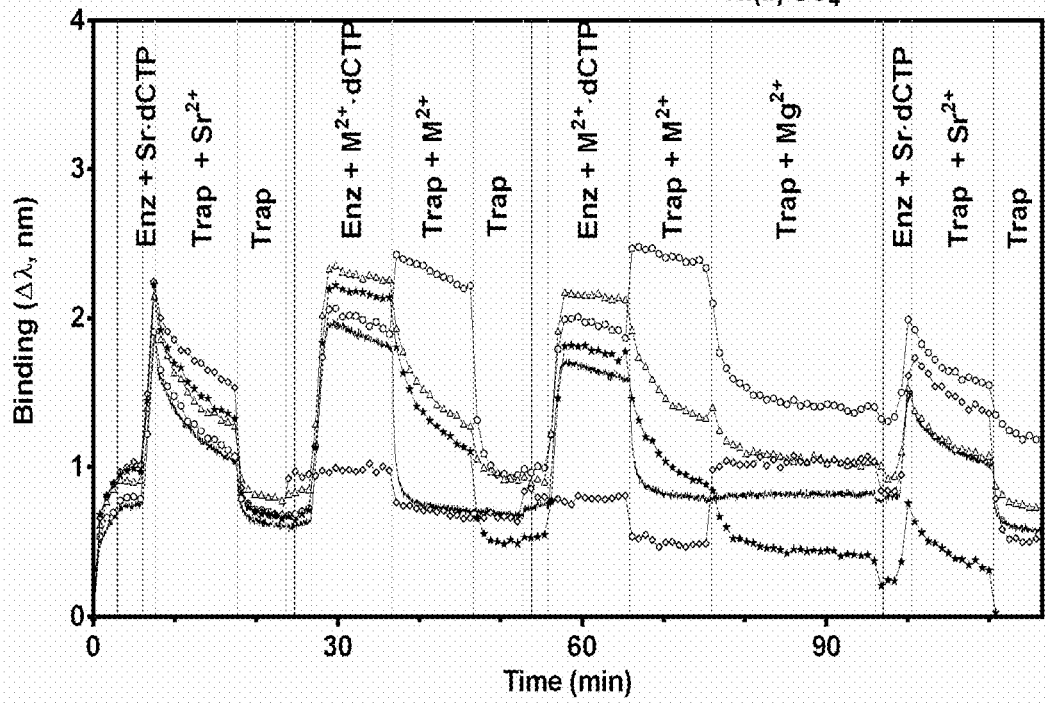
FIGS. 14A and 14B are graphs of divalent cation-mediated binding of Klenow exo- and dCTP to human ALK C4493A mutant and dissociation with or without catalytic metal ($MgCl_2$).

Assays were performed for binding of polymerase and dCTP to biosensor coated with ssDNA primer-template. In the first non-catalytic cycle, Klenow exo- enzyme bound strongly to the biosensor in the presence of correct nucleotide (dCTP) and $SrCl_2$ followed by wash that returns to baseline (FIG. 14A, Peak#1). In the second (non-catalytic) cycle, the sensors are bound strongly by enzyme and dCTP in the presence of $Ni(II)SO_4$, $BaCl_2$ and $SrCl_2$ but not EDTA (Figure BBBB A, Peak#2-3). Wash Buffer containing $Ni(II)SO_4$ stabilizes the ternary complex over the course of 10 minutes (FIG. 14A, Peak#2-3). Signal decreases in the presence of $Mg^{2+}$ (FIG. 14A, Peak#3 dissociation) which corresponds to incorporation as evidenced by low levels of $Sr^{2+}$-mediated binding by Klenow exo- and dCTP (FIG. 14A, Peak #4). These results demonstrate the ability of $Ni^{2+}$ to stabilize the ternary complex of Klenow exo-, dNTP and ssDNA primer/template in buffers lacking dNTP, and this stabilization is compatible with enzymatic incorporation of nucleotide by the DNA polymerase.

Figure 14B:
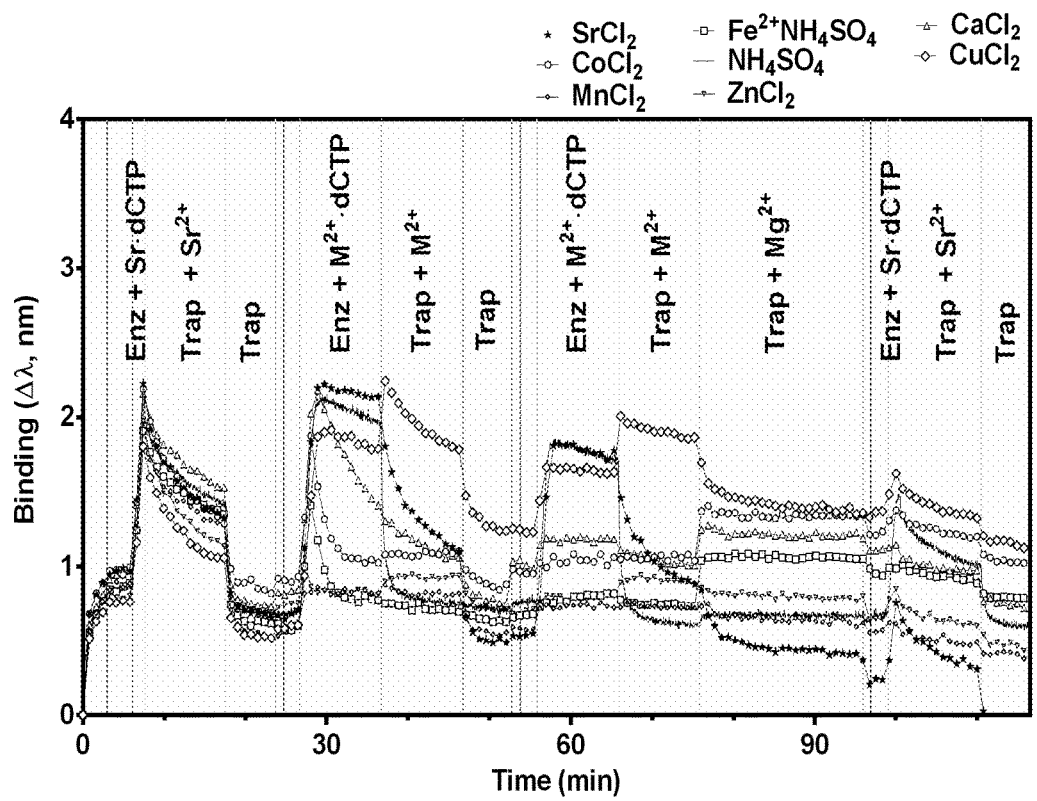

Klenow exo- exhibits polymerase activity in the presence of alternative divalent cations other than magnesium ion. Assays were performed for binding of polymerase and dCTP to biosensor coated with ssDNA primer-template. In the first non-catalytic cycle, Klenow exo- enzyme bound strongly to the biosensor in the presence of correct nucleotide (dCTP) and $SrCl_2$ followed by wash that returns to baseline (FIG. 14B, Peak#1). In the second binding cycle, the sensors are bound strongly by enzyme and dCTP in the presence of $SrCl_2$ or ammonium sulfate (FIG. 14B, Peak#2-3). However, several divalent cations ($Cu^{2+}$, $Ca^{2+}$, $Co^{2+}$, $Fe^{2+}$, $Zn^{2+}$) displayed a transient peak for binding immobilized primer/template by Klenow exo- and dCTP in the Binding Buffer (FIG. 14B, Peak 2). Following the disappearance of the transient peak ($Ca^{2+}$, $Co^{2+}$, $Fe^{2+}$, $Zn^{2+}$) or the flat peak ($Mn^{2+}$), Wash Buffer containing the same divalent cations and salmon sperm DNA trap or trap alone did not further decrease the binding signal (except for $Ca^{2+}$ brought to baseline) in FIG. 14A (Peak#2). In cycle 3, a second exposure of biosensors to enzyme, dCTP and the divalent cations $Ca^{2+}$, $Co^{2+}$, $Fe^{2+}$, $Zn^{2+}$ did not exhibit appreciable binding (FIG. 14B, Peak 3), nor did the standard Sr'-mediated binding control (FIG. 14B, Peak 4). To a lesser extent, $Cu^{2+}$ also appears to enhance polymerase activity by Klenow exo-, because the second exposure to $Cu^{2+}$ (FIG. 14B, Peak 3) was less than the first $Cu^{2+}$ binding (FIG. 14B, Peak 2). This lack of binding signal for divalent cations ($Ca^{2+}$, $Co^{2+}$, $Fe^{2+}$, $Zn^{2+}$, $Mn^{2+}$) after the first exposure to enzyme+dNTP and failure of $Sr^{2+}$-mediated control conditions to support binding suggests that complete nucleotide incorporation was achieved using certain divalent cations ($Ca^{2+}$, $Co^{2+}$, $Fe^{2+}$, $Zn^{2+}$, $Mn^{2+}$) in the absence of $Mg^{2+}$, and these transient peaks can be used for DNA sequencing.

Example 15. Long Read-Lengths by Sequencing Single-Stranded DNA Using $CoCl_2$-Mediated Binding and Catalysis

```
DNA sequence of template oligonucleotide phiX_
100mismatch:
                                      (SEQ ID NO: 22)
Biotin-5'- GGCAAATCACCAGAAGGCGGTTCCTGAATGAATGGGAAG

CCTTCAAGAA-GGTGATAAGCAGGAGAAACATACGAAGCATCATAACGAT

ACCACTGACCC -3'
```

```
DNA sequence of primer oligonucleotide FP2:
                                       (SEQ ID NO: 5)
5'-GAGGGTCAGTGGTATCGTTATG-3'
```

Reagent Preparation.

Oligonucleotides were synthesized and analyzed (liquid chromatography-mass spectrometry (LC-MS) and electrospray ionization (ESI)) by Integrated DNA Technologies (Coralville, Iowa). Oligonucleotides were prepared in TE Buffer (10 mM Tris pH 8.0, 0.1 mM EDTA) to 100 μM. To prepare the ssDNA primer/template, oligonucleotides "phiX_100mismatch" and "FP2" were combined (10 μM each strand) in a tube containing Annealing Buffer (10 mM Tris pH 8.0, 0.1 mM EDTA, 80 mM KCl). The tube containing oligonucleotide solutions was loaded onto a dry heat block (95° C. for 5 min), and the block was transferred to the bench top to anneal strands by gradual cooling to ambient temperature. Klenow (3'→5' exo-) fragment of E.

coli DNA polymerase was purchased from Enzymatics (Beverly, Mass.; catalog no. P7010-LC-L). Ultra-pure bovine serum albumin (BSA) and UltraPure Salmon Sperm DNA Solution were purchased from Life Technologies (Foster City, Calif.). Saccharomyces cerevisiae nucleoside diphosphate kinase (NDPK) enzyme (catalog no. N0379), adenosine diphosphate (ADP) and cobalt(II) chloride hexahydrate (catalog no. 255599) were purchased from Sigma (St. Louis, Mo.). All reagents and solutions were molecular biology grade.

Experimental Conditions.

Primer-template duplex was diluted (100 nM) into Annealing Buffer. Wash Buffer was 20 mM Tris, pH 8.0, 200 mM KCl, 200 mM potassium glutamate, 0.01% (v/v) Tween-20, 100 µg/mL bovine serum albumin, 1.0 mM dithiothreitol. Binding Buffer was Wash Buffer containing low $CoCl_2$ (0.050 mM). Reaction Buffer was Binding Buffer containing high $CoCl_2$ (15 mM). EDTA Wash Buffer was Binding Buffer containing 1.0 mM EDTA. Buffer containing Primer-Template (PT), Binding buffer containing one dNTP, and Reaction Buffer were loaded (200 µL/well) into a Greiner 96-well black microplate (Sigma-Aldrich, St. Louis, Mo.; catalog number M9685), and PCR-grade mineral oil (Sigma-Aldrich, St. Louis, Mo.; catalog no. M8662) was applied (75 µL/well). High-precision streptavidin biosensors (Pall ForteBio Corp., Menlo Park, Calif.; catalog number 18-5117) were re-hydrated in Annealing Buffer for approximately 10 minutes before use. The Octet QK biosensor system (Pall ForteBio Corp., Menlo Park, Calif.) was set for 30° C. operation and was programmed to coat the biosensors with Primer-Template and wash away unbound Primer-Template with Wash Buffer. Biosensors were transferred to Binding Buffer containing Klenow exo- (68 Unit/mL), $CoCl_2$ (100 µM) and 100 µM dNTP (dATP, dTTP, dGTP or dCTP) as indicated (association phase) followed by dNTP incorporation (dissociation phase) in Reaction Buffer containing $CoCl_2$ (15 mM), NDPK, ADP (1 mM) and salmon sperm DNA (500 µg/mL). Biosensors were transferred to EDTA Wash Buffer followed by re-equilibration in Reaction Buffer without enzyme, nucleotide or divalent cation. Similarly, biosensors were transferred cyclically to solutions containing individual deoxyribonucleoside triphosphates (dATP, dGTP, dCTP or dTTP) as indicated. Duplicate cycles of binding and incorporation were repeated for each dNTP to assess sequencing.

Data Analysis.

Data were imported into Microsoft Excel and Prism software (GraphPad Software, San Diego, Calif.) for display.

Results.

Figure 15:
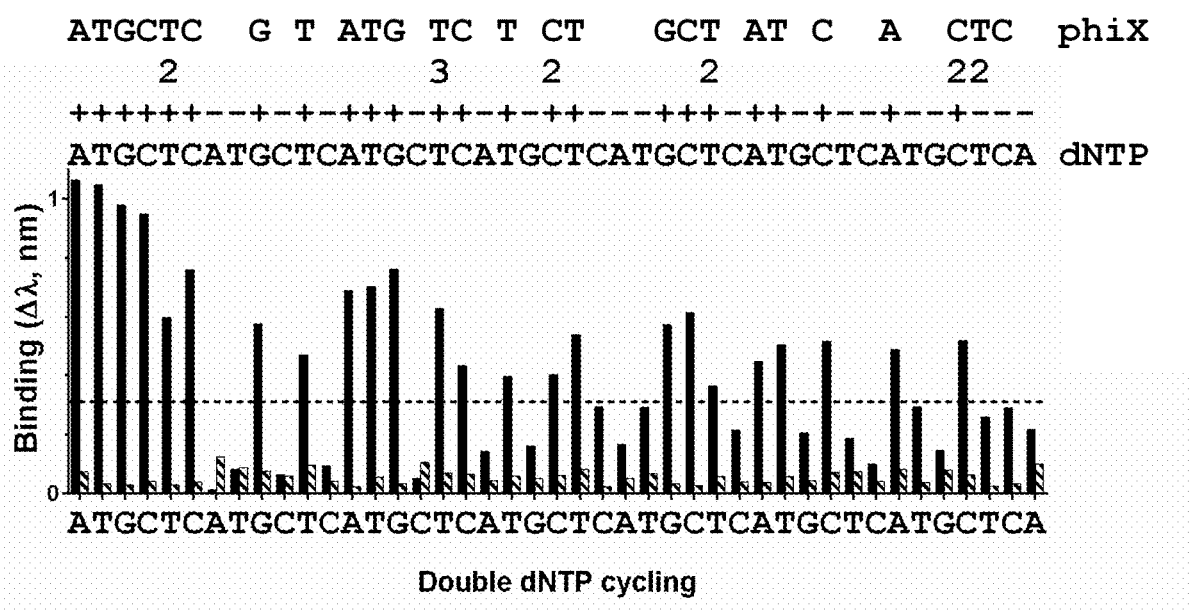
FIG. 15 is a graph of Klenow exo- sequencing of human ALK C4493A mutant in which binding is mediated by low concentration of $CoCl_2$, and incorporation is mediated by high concentration of $CoCl_2$.

In assays for binding to biosensor coated with ssDNA primer-template, Klenow (exo-) enzyme bound poorly to the biosensor in the absence of dNTP (FIG. 15, hatched bars). In the presence of the correct individual dNTPs, strong peaks were observed for the first 40 cycles (FIG. 15, black bars) that correspond to the 100% correct DNA sequence for the first 30 nucleotides, assuming that each homopolymer is compressed into a single peak. Thereafter, small peak heights were observed in cycles 41 onward that did not correspond to discernable sequence. These results demonstrate the ability to sequence double-stranded DNA using Klenow exo- fragment of DNA polymerase with the binding of enzyme-dNTP-primer/template ternary complex in examination phase mediated by low $Co^{2+}$ concentration followed by dNTP incorporation in the presence of high $Co^{2+}$ concentration.

Example 16. Long Read-Lengths by Sequencing Single-Stranded DNA Using Nickel-Enhanced Binding, Magnesium Exchange and Catalysis in Presence of Polymerase Trap and dNTP-Scavenging Enzyme DNA sequence of template oligonucleotide Btn-4460-4509S C4493A with 3' inverted dT:
(SEQ ID NO: 21)
Biotin-5'-GTGAGCCTGCAATCCCTGCCCCGGTTCATCCTGATGGAGC TCATGGCGGG-3'-(3'-dT-5')

DNA sequence of primer oligonucleotide 4496-4509AS:
(SEQ ID NO: 10)
5'-CCCGCCATGAGCTC-3'

Reagent Preparation.

Oligonucleotides were synthesized and analyzed (liquid chromatography-mass spectrometry (LC-MS) and electrospray ionization (ESI)) by Integrated DNA Technologies (Coralville, Iowa). Oligonucleotides were prepared in TE Buffer (10 mM Tris pH 8.0, 0.1 mM EDTA) to 100 µM. To prepare the ssDNA primer/template, oligonucleotides "Btn-4460-4509S C4493A" and "4496-4509AS" were combined (10 µM each strand) in a tube containing Annealing Buffer (10 mM Tris pH 8.0, 0.1 mM EDTA, 80 mM KCl). The tube containing oligonucleotide solutions was loaded onto a dry heat block (95° C. for 5 min), and the block was transferred to the bench top to anneal strands by gradual cooling to ambient temperature. Klenow (3'→5' exo-) fragment of E. coli DNA polymerase was purchased from Enzymatics (Beverly, Mass.; catalog no. P7010-LC-L). Ultra-pure bovine serum albumin (BSA) and UltraPure Salmon Sperm DNA Solution were purchased from Life Technologies (Foster City, Calif.). Saccharomyces cerevisiae nucleoside diphosphate kinase (NDPK) enzyme (catalog no. N0379), adenosine diphosphate (ADP) and nickel(II) sulfate hexahydrate (catalog no. 467901) were purchased from Sigma (St. Louis, Mo.). All reagents and solutions were molecular biology grade.

Experimental Conditions.

Primer-template duplex was diluted (100 nM) into Annealing Buffer. Wash buffer was 20 mM Tris, pH 8.0, 200 mM KCl, 200 mM potassium glutamate, 0.01% (v/v), Tween-20, 100 µg/mL bovine serum albumin, 1.0 mM dithiothreitol. Binding Buffer was Wash Buffer containing 2.0 mM $Ni(II)SO_4$. Reaction Buffer was Binding Buffer containing $MgCl_2$ (10 mM). EDTA Wash Buffer was Binding Buffer containing 1.0 mM EDTA. Buffer containing Primer-Template (PT), Binding buffer containing one dNTP and Reaction Buffer were loaded (200 µL/well) into a Greiner 96-well black microplate (Sigma-Aldrich, St. Louis, Mo.; catalog number M9685), and PCR-grade mineral oil (Sigma-Aldrich, St. Louis, Mo.; catalog no. M8662) was applied (75 µL/well). High-precision streptavidin biosensors (Pall ForteBio Corp., Menlo Park, Calif.; catalog number 18-5117) were re-hydrated in Annealing Buffer for approximately 10 minutes before use. The Octet QK biosensor system (Pall ForteBio Corp., Menlo Park, Calif.) was set for 30° C. operation and was programmed to coat the biosensors with Primer-Template and wash away unbound Primer-Template with Wash Buffer. Biosensors were transferred to Binding Buffer containing Klenow exo- (68 Unit/mL), $Ni(II)SO_4$ (2.0 mM) and 100 µM dNTP (dATP, dTTP, dGTP or dCTP) as indicated (association phase) followed by dNTP incorporation (dissociation phase) in Reaction Buffer containing MgCl$_2$ (10 mM), NDPK, ADP (1 mM) and salmon sperm DNA (500 µg/mL). Biosensors were transferred to EDTA Wash Buffer followed by re-equilibration in Reaction Buffer without enzyme, nucleotide or divalent cation. Similarly, biosensors were transferred cyclically to solutions containing individual deoxyribonucleoside triphosphates (dATP, dGTP, dCTP or dTTP) as indicated. Duplicate cycles of binding and incorporation were repeated for each dNTP to assess sequencing.

Data Analysis.

Data were imported into Microsoft Excel and Prism software (GraphPad Software, San Diego, Calif.) for display.

Results.

Figure 16:
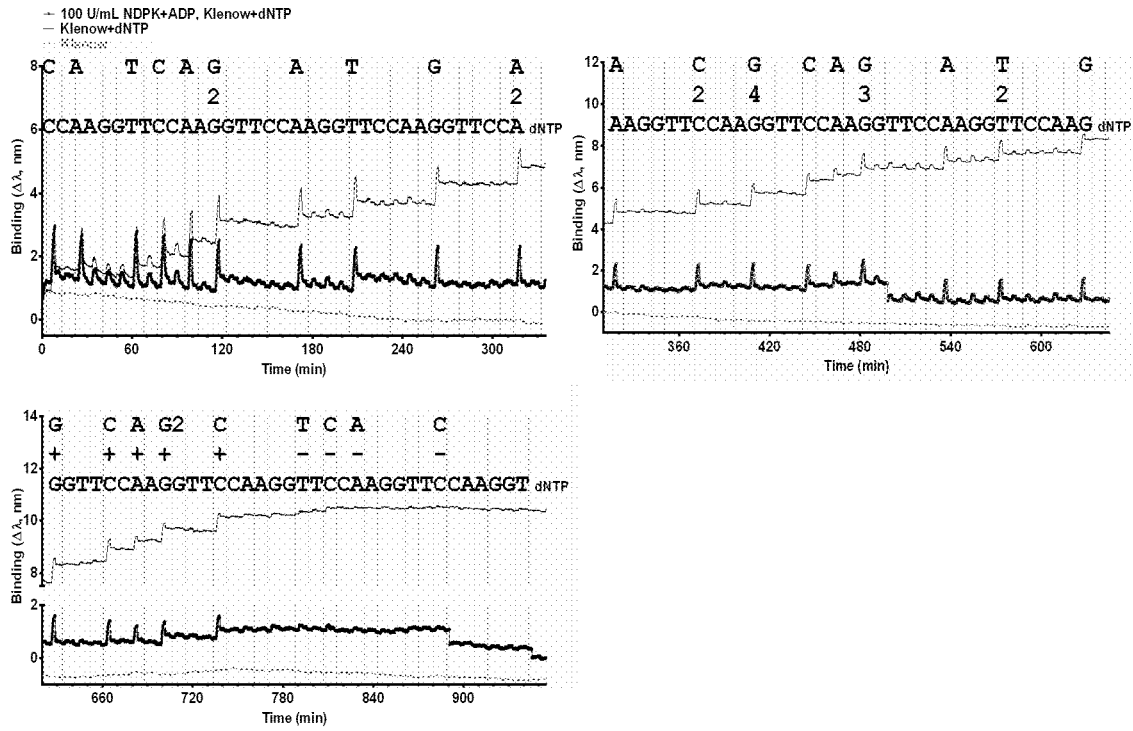
FIG. 16 is a graph of Klenow exo- sequencing of human ALK C4493A mutant in which binding is mediated by $Ni(II)SO_4$, and incorporation is effected by $MgCl_2$. Dissociation to baseline is observed only in the presence of nucleoside diphosphate kinase and ADP, which scavenge free dNTP thus prevent re-binding of dNTP into the complex of Klenow exo- and primer/template.

In assays for binding to biosensor coated with ssDNA primer-template, Klenow (exo-) enzyme bound poorly to the biosensor in the absence of dNTP (FIG. 16, "Klenow"). In the presence of the correct individual dNTPs, strong peaks were observed (FIG. 16, "Klenow+dNTP") that correspond to the 100% correct DNA sequence for the first 32 nucleotides (CATCAGGATGAACCGGGGCAGGGATTGCAGGC (SEQ ID NO:23)), assuming that each homopolymer is compressed into a single peak. After 750 min, signal was minimal and did not yield discernable sequence for the final four nucleotides (TCAC).

Homopolymer compression could result from polymerase incorporating more than one dNTP in the reaction buffer. Two methods were employed to prevent homopolymer compression by conditions intended to support single-turnover incorporation. First, to block free Klenow from re-binding to the primer/template and incorporating a second dNTP, some Reaction Buffers contained an excess of salmon sperm DNA as a polymerase trap. Second, to prevent free dNTP in the Reaction Buffer from re-binding the Klenow-primer/template complex and being enzymatically incorporated into the nascent chain, Reaction Buffers containing NDPK and ADP were intended to convert free dNTP to dNDP and ATP so that the dNDP cannot be incorporated by polymerase. The ternary complex was formed in the (association phase), which was followed by dissociation in Reaction Buffers. Reaction buffers containing the polymerase trap demonstrated an accumulation on the biosensor tip as evidenced by the binding amplitude exceeding the dissociation amplitude (FIG. 16, "Klenow+dNTP"). By contrast, Reaction Buffers containing NDPK and ADP produced baseline resolution following dissociation, suggesting that dissociation phase was complete (FIG. 16, "NDPK+ADP+Klenow+dNTP"). These results suggest a role for dNTP in re-binding to the polymerase-primer/template complex that can result in capped, non-productive termination of sequencing. Reaction Buffers containing NDPK and ADP appear to prevent these non-productive capped products by depleting the pool of free dNTP during catalysis. Single-turnover incorporation was not achieved, since homopolymer compression was observed even in the presence of salmon sperm DNA, NDPK and ADP; the expected sequence (CATCAG$_2$ATGA$_2$C$_2$G$_4$CAG$_3$AT$_2$GCAG$_2$CTCAC (SEQ ID NO:24)) was detected as CATCAGATGACGCAGATGCAGC (SEQ ID NO:25) without sequential dinucleotides (GG, AA, CC or TT), trinucleotide (GGG) or tetranucleotide (GGGG) as shown in FIG. 16.

Taken together, these results demonstrate the ability to sequence single-stranded DNA using Klenow exo- fragment of DNA polymerase with the binding of enzyme-dNTP-primer/template ternary complex in examination phase mediated by Ni$^{2+}$ ion followed by dNTP incorporation via exchange of divalent cation into MgCl$_2$ resulting in catalytic incorporation of nucleotide into the primer-template.

Example 17. Homopolymer Resolution by Sequencing Single-Stranded DNA Using Nickel(II)-Enhanced Binding, Magnesium Exchange and Catalysis in Presence of Polymerase Trap and 2'-Deoxyribonucleoside Diphosphate DNA sequence of template oligonucleotide Btn-4460-4509S C4493A with 3' inverted dT:

(SEQ ID NO: 21)
Biotin-5'-GTGAGCCTGCAATCCCTGCCCCGGTTCATCCTGATGGAGC

TCATGGCGGG-3'-(3'-dT-5')

DNA sequence of primer oligonucleotide 4496-4509AS:

(SEQ ID NO: 10)
5'-CCCGCCATGAGCTC-3'

Reagent Preparation.

Oligonucleotides were synthesized and analyzed (liquid chromatography-mass spectrometry (LC-MS) and electrospray ionization (ESI)) by Integrated DNA Technologies (Coralville, Iowa). Oligonucleotides were prepared in TE Buffer (10 mM Tris pH 8.0, 0.1 mM EDTA) to 100 µM. To prepare the ssDNA primer/template, oligonucleotides "Btn-4460-4509S C4493A" and "4496-4509AS" were combined (10 µM each strand) in a tube containing Annealing Buffer (10 mM Tris pH 8.0, 0.1 mM EDTA, 80 mM KCl). The tube containing oligonucleotide solutions was loaded onto a dry heat block (95° C. for 5 min), and the block was transferred to the bench top to anneal strands by gradual cooling to ambient temperature. Bsu DNA polymerase I (large fragment) from *Bacillus subtilis* lacking exonuclease activity was purchased from New England Biolabs (Ipswich, Mass.; catalog no. M0330L). Ultra-pure bovine serum albumin (BSA) and UltraPure Salmon Sperm DNA Solution were purchased from Life Technologies (Foster City, Calif.). Nickel(II) sulfate hexahydrate (catalog no. 467901), dCDP, dGDP and dTDP were purchased from Sigma (St. Louis, Mo.). All reagents and solutions were molecular biology grade.

Experimental Conditions.

Primer-template duplex was diluted (100 nM) into Annealing Buffer. Wash buffer was 20 mM Tris, pH 8.0, 200 mM KCl, 200 mM potassium glutamate, 0.01% (v/v), Tween-20, 100 µg/mL bovine serum albumin, 1.0 mM dithiothreitol. Binding Buffer was Wash Buffer containing 2.0 mM Ni(II)SO$_4$. Reaction Buffer was 20 mM Tris, pH 8.0, 50 mM KCl, MgCl$_2$ (10 mM), 0.01% (v/v) Tween-20, 100 µg/mL bovine serum albumin, 1.0 mM dithiothreitol. EDTA Wash Buffer was Binding Buffer containing 1.0 mM EDTA. Buffer containing Primer-Template (PT), Binding buffer containing one dNTP and Reaction Buffer were loaded (200 µL/well) into a Greiner 96-well black microplate (Sigma-Aldrich, St. Louis, Mo.; catalog number M9685), and PCR-grade mineral oil (Sigma-Aldrich, St. Louis, Mo.; catalog no. M8662) was applied (75 µL/well). High-precision streptavidin biosensors (Pall ForteBio Corp., Menlo Park, Calif.; catalog number 18-5117) were rehydrated in Annealing Buffer for approximately 10 minutes before use. The Octet QK biosensor system (Pall ForteBio Corp., Menlo Park, Calif.) was set for 30° C. operation and was programmed to coat the biosensors with Primer-Template and wash away unbound Primer-Template with Wash Buffer. Biosensors were transferred to Binding Buffer containing Bsu Pol I (68 Unit/mL), Ni(II)SO$_4$ (1.0 mM) and 100 μM dNTP (dATP, dTTP, dGTP or dCTP) as indicated (association phase) followed by dNTP incorporation (dissociation phase) in Reaction Buffer containing MgCl$_2$ (10 mM), salmon sperm DNA (500 μg/mL) and the corresponding dNDP (except for dADP which was not used). Biosensors were transferred to EDTA Wash Buffer followed by re-equilibration in Reaction Buffer without enzyme, nucleotide or divalent cation. Similarly, biosensors were transferred cyclically to solutions containing individual deoxyribonucleoside triphosphates (dATP, dGTP, dCTP or dTTP) as indicated. Cycles of binding and incorporation were repeated for each dNTP to assess sequencing.

Data Analysis.

Data were imported into Microsoft Excel and Prism software (GraphPad Software, San Diego, Calif.) for display.

Results.

Figure 17A:
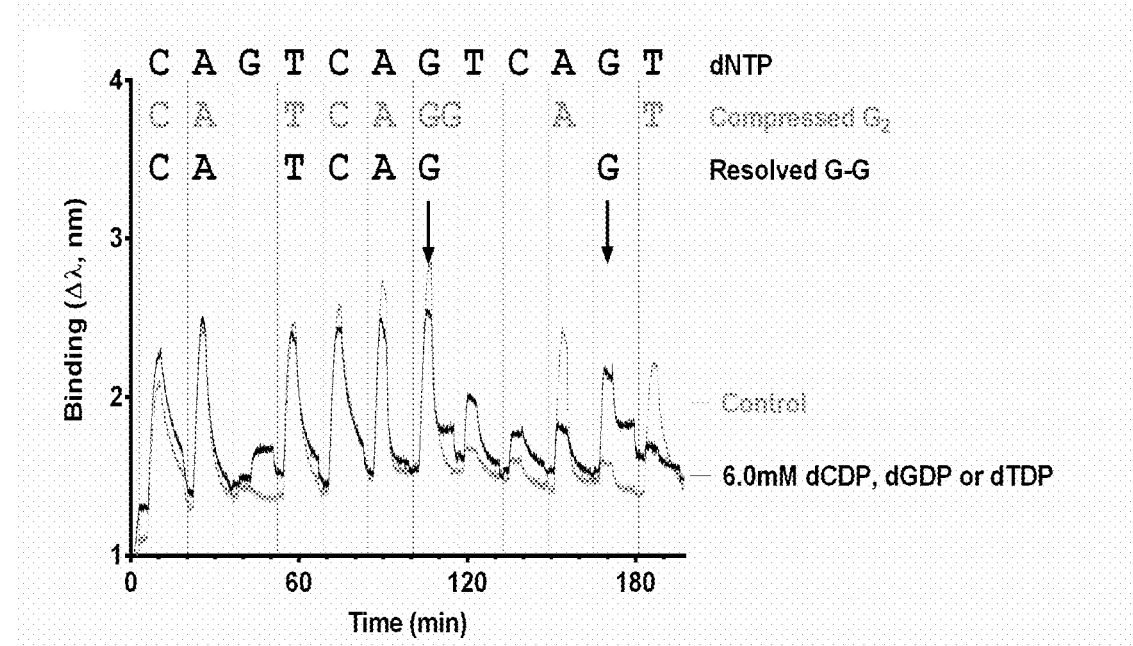
FIGS. 17A and 17B are graphs showing homopolymer resolution during Bsu Pol I (large fragment) sequencing of human ALK C4493A mutant. Binding is mediated by $Ni(II)SO_4$, incorporation by $MgCl_2$, and dissociation in the presence or absence of dNDP.

In assays for binding to biosensor coated with ssDNA primer-template, Bsu Pol I enzyme bound strongly to the biosensor in the presence of correct dNTP (FIG. 17A). Signal peaks in which the Reaction Buffer contains excess dNDP (3.0 mM) correspond to correct DNA sequence of CATCAGG with the two GG of the homopolymer are resolved with detection of two distinct peaks (FIG. 17A, arrows). In contrast, failure to resolve homopolymer was observed in signal peaks for control lacking dNDP in Reaction Buffer, which correspond to correct DNA sequence of CATCAGGAT assuming that the GG homopolymer is compressed into a single G peak (FIG. 17A, "Control"). The effect of dNDP on homopolymer resolution is validated by two means: (1.) the height of the second G peak of the GG dinucleotide is dependent upon the concentration of dNDP in the Reaction Buffer (FIG. 17A, second arrow), and (2.) the next nucleotides (A and T) following the GG homopolymer are inversely related to the dNDP concentration in Reaction Buffer.

Figure 17B:
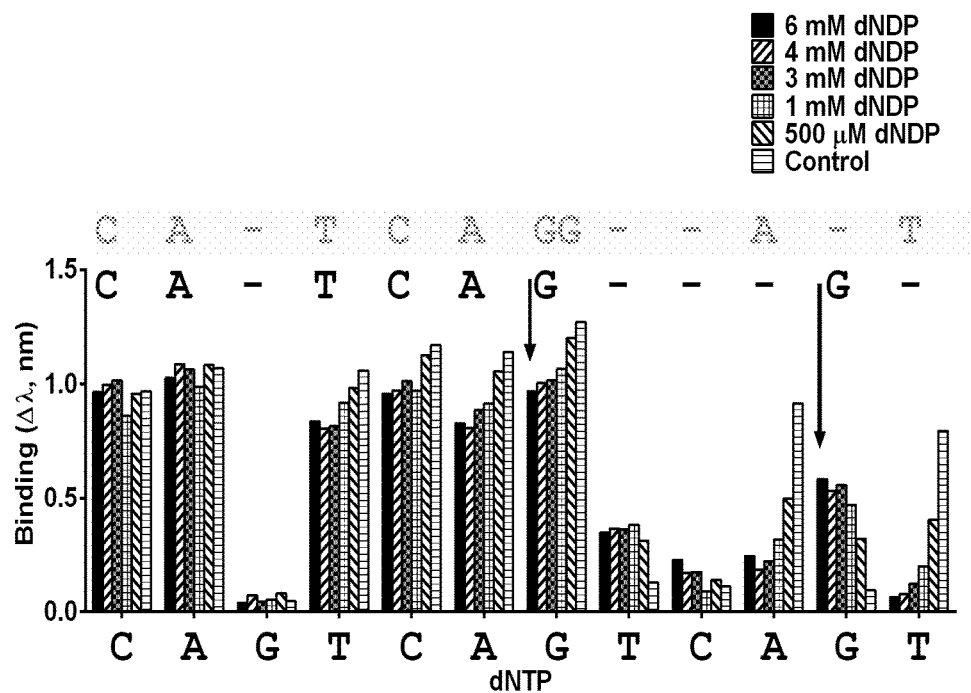

Homopolymer compression could result from polymerase incorporating more than one dNTP in the reaction buffer. Two methods were employed to prevent homopolymer compression by conditions intended to support single-turnover incorporation. First, to block free Bsu Pol I from re-binding to the primer/template and incorporating a second dNTP, the Reaction Buffers contained an excess of salmon sperm DNA as a polymerase trap. Second, to prevent free dNTP in the Reaction Buffer from re-binding the Bsu Pol-primer/template complex and being enzymatically incorporated into the nascent chain, Reaction Buffers containing dNDP to compete for polymerase binding by free dNTP are expected to bind Bsu Pol-primer/template complex and block further incorporation, hence blocking homopolymer compression. The goal of single-turnover incorporation is close to being achieved, since the second peak of the GG homopolymer was 60.1% the size of the first G peak (FIG. 17B), and binding for the next two nucleotides (A and T) by homopolymer compression was diminished by 73.4% and 92.0%, respectively (FIG. 17B).

These results demonstrate the ability to sequence single-stranded DNA using Bsu Pol I (large fragment) with the binding of enzyme-dNTP-primer/template ternary complex in examination phase mediated by Ni$^{2+}$ ion followed by dNTP incorporation via exchange of divalent cation into MgCl$_2$ resulting in catalytic incorporation of nucleotide into the primer-template while improving homopolymer resolution using competing dNDP in Reaction Buffers.

Example 18. Kinetic Method for Homopolymer Resolution by Sequencing Single-Stranded DNA Using Nickel(II)-Enhanced Binding, Magnesium Exchange and Catalysis in Presence of 2'-Deoxyribonucleoside Diphosphate and Competing Substrate

```
DNA sequence of wild-type ALK template oligonuc-
leotide Btn-4460-4509S with 3' inverted dT:
                                       (SEQ ID NO: 7)
Biotin-5'-GTGAGCCTGCAATCCCTGCCCCGGTTCATCCTGCTGGAGC TCATGGCGGG-3'-(3'-dT-5')

DNA sequence of ALK-G1 primer oligonucleotide
4494-4509AS:
                                      (SEQ ID NO: 26)
5'-CCCGCCATGAGCTCCA-3'

DNA sequence of ALK-G2 primer oligonucleotide
4491-4509AS:
                                      (SEQ ID NO: 27)
5'-CCCGCCATGAGCTCCAGCA-3'

DNA sequence of ALK-G3 primer oligonucleotide
4476-4509AS:
                                      (SEQ ID NO: 28)
5'-CCCGCCATGAGCTCCAGCAGGATGAACC/ideoxyI/GGGCA-3', where "/ideoxyI/" is a 2'-deoxyinosine residue.

DNA sequence of ALK-G4 primer oligonucleotide
4482-4509AS:
                                      (SEQ ID NO: 29)
5'-CCCGCCATGAGCTCCAGCAGGATGAACC-3'
```

Reagent Preparation.

Oligonucleotides were synthesized and analyzed (liquid chromatography-mass spectrometry (LC-MS) and electrospray ionization (ESI)) by Integrated DNA Technologies (Coralville, Iowa). Oligonucleotides were prepared in TE Buffer (10 mM Tris pH 8.0, 0.1 mM EDTA) to 100 μM. To prepare the ssDNA primer/template, oligonucleotide "Btn-4460-4509S" and either "4494-4509AS," "4491-4509AS," "4476-4509AS," or "4482-4509AS" (ALK-G1, ALK-G2, ALK-G3 or ALK-G4 duplexes, respectively) were combined (10 μM each strand) in tubes containing Annealing Buffer (10 mM Tris pH 8.0, 0.1 mM EDTA, 80 mM KCl). The tubes containing oligonucleotide solutions were loaded onto a dry heat block (95° C. for 5 min), and the block was transferred to the bench top to anneal strands by gradual cooling to ambient temperature. Bsu DNA polymerase I (large fragment) from *Bacillus subtilis* lacking exonuclease activity was purchased from New England Biolabs (Ipswich, Mass.; catalog no. M0330L). Ultra-pure bovine serum albumin (BSA) and UltraPure Salmon Sperm DNA Solution were purchased from Life Technologies (Foster City, Calif.). The substrate analogs 2'-deoxyadenosine-5'-O-(1-thiotriphosphate) ("α-S-dATP"), 2'-deoxycytidine-5'-O-(1-thiotriphosphate) ("α-S-dCTP"), 2'-deoxyguanosine-5'-O-(1-thiotriphosphate) ("α-S-dGTP") and 2'-deoxythymidine-5'-O-(1-thiotriphosphate) ("α-S-dTTP") were purchased from TriLink Biotechnologies, Inc. (San Diego, Calif.). Nickel(II) sulfate hexahydrate (catalog no. 467901) was purchased from Sigma (St. Louis, Mo.). All reagents and solutions were molecular biology grade.

Experimental Conditions.

Primer-template duplex was diluted (100 nM) into Annealing Buffer. Wash buffer was 30 mM Tris, pH 8.0, 160 mM KCl, 160 mM potassium glutamate, 0.01% (v/v), Tween-20, 100 µg/mL bovine serum albumin, 1.0 mM dithiothreitol. Binding Buffer was Wash Buffer containing Bsu Pol I (68 Unit/mL) 100 µM dGTP+1.0 mM Ni(II)SO$_4$. Reaction Buffer was Wash Buffer containing Bsu (1 U/mL), MgCl$_2$ (80 dGTP (28.1 µM), α-S-dGTP (162 µM). EDTA Wash Buffer was Wash Buffer without Ni(II)SO$_4$ but containing 1.0 mM EDTA. Buffer containing Primer-Template (PT), Binding Buffer and Reaction Buffer containing were loaded (200 µL/well) into a Greiner 96-well black microplate (Sigma-Aldrich, St. Louis, Mo.; catalog number M9685), and PCR-grade mineral oil (Sigma-Aldrich, St. Louis, Mo.; catalog no. M8662) was applied (75 µL/well). High-precision streptavidin biosensors (Pall ForteBio Corp., Menlo Park, Calif.; catalog number 18-5117) were rehydrated in Annealing Buffer for approximately 10 minutes before use. The Octet QK biosensor system (Pall ForteBio Corp., Menlo Park, Calif.) was set for 30° C. operation and was programmed to coat the biosensors with Primer-Template and wash away unbound Primer-Template with Wash Buffer. Biosensors were transferred to Binding Buffer (association phase) followed by dNTP incorporation (dissociation phase) in Reaction Buffer. Biosensors were transferred to EDTA Wash Buffer followed by re-equilibration in Reaction Buffer without enzyme, nucleotide or MgCl$_2$.

Data Analysis.

Data were imported into Microsoft Excel and Prism software (GraphPad Software, San Diego, Calif.) for display. The association phase time series were fitted to a single exponential association equation using Prism software. Association phase kinetic parameters ($k_{obs}$ and amplitude) were analyzed by InStat statistical software (GraphPad Software, San Diego, Calif.) using the Dunnett test with single incorporation of G as the control condition. The dissociation phase time series were fitted to a double exponential dissociation equation using Prism software.

Results.

Figures 18A, 18B:
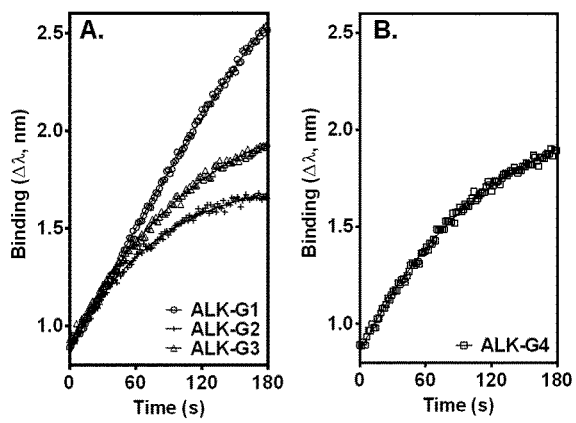

In assays for binding to biosensor coated with ssDNA primer-template, Bsu Pol I enzyme bound strongly to the primer/template-coated biosensor in the presence of correct dGTP (FIGS. 18A and 18B). Signals for binding to ALK-G1 (FIG. 18A) were higher than binding to ALK-G2, ALK-G3 and ALK-G4 (FIGS. 18A and 18B). After biosensor coated with ternary complexes was transferred to incorporation buffer containing polymerase, dGTP and α-S-dGTP, Ni$^{2+}$ and Mg$^{2+}$, distinct dissociation time courses were observed depending on the ALK template (FIG. 18C). The association phase for formation of the ternary complex was analyzed for how the association kinetic parameters may be affected by the number of nucleotides for incorporation into the homopolymer of the primer/template. Primer/templates with multiple (2-4) nucleotides for incorporation into the homopolymer had lower amplitude for association than the control single incorporation (FIG. 18D), which was statistically significant (p<0.01) by the Dunnett test. Similarly, primer/templates with multiple (2-4) nucleotides for incorporation into the homopolymer had higher apparent kinetic constant for association ($k_{obs}$) than the control single incorporation (FIG. 18D), which was statistically significant (p<0.01) by the Dunnett test. This finding indicates that single incorporation is kinetically distinguishable from multiple incorporation in a homopolymer template. Finally, the observed dissociation rate (0-8 s following transfer into Reaction Buffer) increases with increasing numbers of nucleotides for incorporation in the rank order of ALK-G2<ALK-G3<ALK-G4 ALK-G1, where Bsu polymerase concentrations are between 0.13-1 U/mL (FIG. 18E).

These results demonstrate the ability to quantitatively detect single and multiple incorporation into a homopolymer template in a two-step method. First, the kinetic parameters for association of the ternary complex differ for single incorporation (ALK-G1) compared to multiple incorporation (ALK-G2, ALK-G3, ALK-G4). Second, after transfer of the ternary complex-coated biosensor tip to the Reaction Buffer, the initial rate of dissociation (0-8 s) allows incorporation of two, three or four nucleotides in a homopolymer template (ALK-G2, ALK-G3, ALK-G4) to be discerned quantitatively.

What is claimed is:

1. A method of identifying a base in a primed template nucleic acid, comprising
   I. performing an examination step comprising:
   (a) providing a primed template nucleic acid comprising a primer, wherein the primer comprises a reversible terminator moiety at the 3' end;
   (b) contacting the primed template nucleic acid with a polymerase and a test nucleotide, under conditions that:
      (i) stabilize ternary complex formed between the polymerase, primed template nucleic acid and test nucleotide when the test nucleotide is complementary to the next base of the primed template nucleic acid while precluding incorporation of the test nucleotide into the primer, and
      (ii) destabilize binary complex formed between the primed template nucleic acid and the polymerase when the test nucleotide is not complementary to the next base of the primed template nucleic acid;
   (c) washing to remove any unbound polymerase and unbound nucleotides, wherein the washing occurs under conditions that stabilize the ternary complex;
   (d) detecting the ternary complex while precluding incorporation of the test nucleotide into the primer;
   (e) identifying the next base of the primed template nucleic acid from the detected ternary complex.

2. The method of claim 1, wherein the washing comprises contacting the ternary complex with a ternary complex stabilizing agent.

3. The method of claim 1, further comprising a reloading step, the reloading step comprising contacting the primed template nucleic acid with a polymerase and a nucleotide that is complementary to the next base.

4. The method of claim 3, further comprising an incorporation step following the reloading step, the incorporation step comprising incorporating into the primer a nucleotide that is complementary to the next base.

5. The method of claim 1, further comprising an incorporation step, the incorporation step comprising incorporating into the primer a nucleotide that is complementary to the next base.

6. The method of claim 5, wherein step I. is repeated at least once using a different type of test nucleotide prior to the incorporation step.

7. The method of claim 5, wherein the nucleotide that is incorporated comprises a reversible terminator moiety.

8. The method of claim 7, wherein the nucleotide that is incorporated is unlabeled.

9. The method of claim 5, wherein the incorporation step further comprises replacing the polymerase with a different type of polymerase that catalyzes the incorporation.

10. The method of claim 1, further comprising an incorporation step, the incorporation step comprising replacing the test nucleotide with a second nucleotide and incorporating the second nucleotide into the primer.

11. The method of claim 10, wherein the second nucleotide comprises a reversible terminator moiety.

12. The method of claim 11, wherein the second nucleotide is unlabeled.

13. The method of claim 10, wherein the incorporation step further comprises replacing the polymerase with a different type of polymerase that catalyzes the incorporation.

14. The method of claim 1, wherein the conditions comprise presence of a polymerase inhibitor that precludes incorporation of the test nucleotide into the primer.

15. The method of claim 1, wherein the conditions comprise an amino acid mutation in the polymerase that precludes incorporation of the test nucleotide into the primer.

16. The method of claim 1, wherein the conditions comprise presence of a reversible terminator on the 3' end of the primer that precludes incorporation of the test nucleotide into the primer.

17. The method of claim 1, wherein the test nucleotide comprises a label moiety.

18. The method of claim 1, further comprising repeating step I. at least once using a second test nucleotide that is different from the test nucleotide.

19. The method of claim 1, wherein the primed template nucleic acid is attached to a surface.

20. The method of claim 19, wherein the surface is attached to a clonally amplified population of the primed template nucleic acid.

21. The method of claim 19, wherein the surface comprises a plurality of different template nucleic acids.

22. The method of claim 1, wherein the conditions of step (b) comprise presence of a non-catalytic metal ion.

23. The method of claim 1, wherein the conditions of step (b) comprise presence of salt at a concentration in the range of 50 to 1500 mM.

24. The method of claim 1, wherein the detecting comprises detecting a change in refractive index, a light scattering signal or a detectable tag.

* * * * *